(12) United States Patent
Bhaskara

(10) Patent No.: US 11,154,551 B2
(45) Date of Patent: Oct. 26, 2021

(54) HDAC1,2 INHIBITORS AND METHODS OF USING THE SAME

(71) Applicant: UNIVERSITY OF UTAH RESEARCH FOUNDATION, Salt Lake City, UT (US)

(72) Inventor: Srividya Bhaskara, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 16/265,721

(22) Filed: Feb. 1, 2019

(65) Prior Publication Data

US 2019/0160056 A1    May 30, 2019

Related U.S. Application Data

(63) Continuation of application No. 15/541,012, filed as application No. PCT/US2015/067883 on Dec. 29, 2015, now abandoned.

(60) Provisional application No. 62/097,727, filed on Dec. 30, 2014.

(51) Int. Cl.
| | |
|---|---|
| *G01N 33/574* | (2006.01) |
| *A61K 45/06* | (2006.01) |
| *A61K 31/496* | (2006.01) |
| *A61K 31/704* | (2006.01) |
| *A61K 31/5377* | (2006.01) |

(52) U.S. Cl.
CPC ........ *A61K 31/496* (2013.01); *A61K 31/5377* (2013.01); *A61K 31/704* (2013.01); *A61K 45/06* (2013.01); *G01N 33/5748* (2013.01); *G01N 33/57426* (2013.01); *G01N 33/57484* (2013.01); *G01N 2333/47* (2013.01); *G01N 2800/52* (2013.01)

(58) Field of Classification Search
CPC .............. A61K 31/496; A61K 31/5377; A61K 31/704; A61K 45/06; G01N 2333/47; G01N 2800/52; G01N 33/57426; G01N 33/5748; G01N 33/57484
See application file for complete search history.

(56) References Cited

U.S. PATENT DOCUMENTS

| | | |
|---|---|---|
| 9,145,412 B2 | 9/2015 | Van Duzer et al. |
| 2008/0248506 A1 | 10/2008 | Bass et al. |
| 2008/0255149 A1 | 10/2008 | Dobler et al. |
| 2010/0216796 A1 | 8/2010 | Kattar et al. |
| 2012/0071341 A1 | 3/2012 | Weaver et al. |
| 2013/0316341 A1 | 11/2013 | Sanders et al. |
| 2013/0323247 A1 | 12/2013 | Zugmaier et al. |
| 2014/0051680 A1 | 2/2014 | Jacques et al. |
| 2014/0128391 A1 | 5/2014 | Van Duzer et al. |
| 2014/0128410 A1 | 5/2014 | Cai et al. |
| 2014/0378470 A1 | 12/2014 | Creasy et al. |

FOREIGN PATENT DOCUMENTS

| | | | |
|---|---|---|---|
| WO | WO-2013052800 A2 * | 4/2013 | ............... C12Q 1/25 |
| WO | WO 2016/109549 A1 | 7/2016 | |

OTHER PUBLICATIONS

Graf Einsiedel et. al., Leukemia, 2006, Nature Publishing Group, vol. 20, pp. 1435-1436 (Year: 2006).*
Martelli et. al., Critical Rev. Oncology/Hematology, vol. 87, pp. 146-171, publ. 2013 (Year: 2013).*
Cobaleda et. al., BioEssays, vol. 31, pp. 600-609, publ. 2009 (Year: 2009).*
Bhaskara, "Histone deacetylases 1 and 2 regulate DNA replication and DNA repair: potential targets for genome stability-mechanism-based therapeutics for a subset of cancers," Cell Cycle, 2015, 14(12):1779-1785.
Bowers et al., "Synthesis and HDAC Inhibitory Activity of Larazole Analogs: Alteration of the Zinc-Binding Domain and Macrocyclic Scaffold," Organic Letters, 2009, vol. 11 (6), pp. 1301-1304.
Johnson et al., "HDAC1,2 inhibition impairs EZH2- and BBAP-mediated DNA repair to overcome chemoresistance in EZH2 gain-of-function mutant diffuse large B-cell lymphoma," Oncotarget, 2014, 6(7):4863-4887.
Li et al., "Gene silencing of MIR22 in acute lymphoblastic leukaemia involves histone modifications independent of promoter DNA methylation," British Journal of Haematology, 2009, vol. 148, pp. 69-79.
Marks et al., "Dimethyl sulfoxide to vorinostat: development of this histone deacetylase inhibitor as an anticancer drug," Nature Biotechnology, 2007, 25(1):84-90.
Nguyen et al., "HDAC Inhibitors Potentiate the Activity of the BCR/ABL Kinase Inhibitor KW-2449 in Imatinib-Sensitive or -Resistant BCR/ABL+ Leukemia Cells In Vitro and In Vivo," Clinical Cancer Research, 2011, 17(10): 3219-3232.
Sorich et al., "In vivo Response to Methotrexate Forecasts Outcome of Acute Lymphoblastic Leukemia and Has a Distinct Gene Expression Profile," PLoS Medicine, 2008, vol. 5(4), e83.
Tan et al., "Novel histone deacetylase inhibitors in clinical trials as anti-cancer agents," Journal of Hematology & Oncology, 2010, vol. 3, pp. 1-13.
Wistuba et al., "Methodological and practical challenges for personalized cancer therapies," Nature Reviews Clinical Oncology, 2011, vol. 8, pp. 135-141.

(Continued)

*Primary Examiner* — Sarah Pihonak
(74) *Attorney, Agent, or Firm* — Michael Best & Friedrich LLP

(57) ABSTRACT

Disclosed herein are methods for treating a cancer and a method for sensitizing a cancer to a chemotherapeutic agent. Each method administers an agent that selectively inhibits HDAC1 and HDAC2 to a subject in need thereof. Also disclosed herein are methods for determining if a cancer is sensitive to an agent that selectively inhibits HDAC1 and HDAC2 and methods for monitoring the efficacy of a treatment for a cancer that includes administration of an agent that selectively inhibits HDAC1 and HDAC2.

19 Claims, 46 Drawing Sheets

(56) References Cited

OTHER PUBLICATIONS

Yan et al., "The BBAP E3 Ligase Monoubiquitylates Histone H4 at Lysine 91 and Selectively Modulates the DNA Damage Response in Chemotherapy-Resistant Lymphomas," Blood, American Society of Hematology, 2009, 114(22): 1522.
International Search Report and Written Opinion for Application No. PCT/US2015/067883 dated Mar. 18, 2016 (14 pages).
European Patent Office Supplementary Search Report for Application No. 15876176.7 dated Jul. 24, 2018 (14 pages).
European Patent Office Extended Search Report for Application No. 15876176.7 dated Oct. 24, 2018 (11 pages).
European Patent Office Examination Report for Application No. 15876176.7 dated Feb. 23, 2021 (4 pages).

* cited by examiner

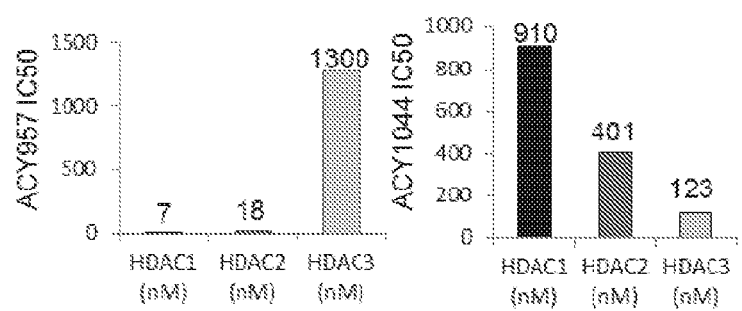
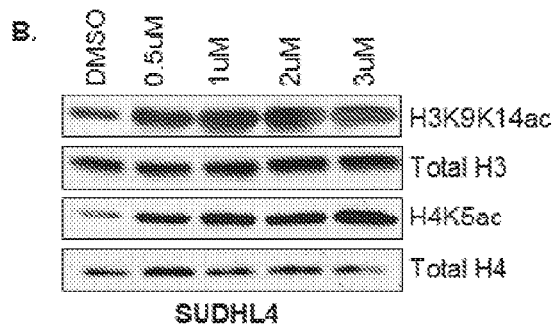
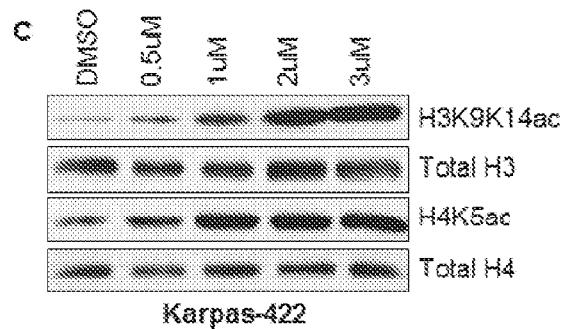
FIG. 2

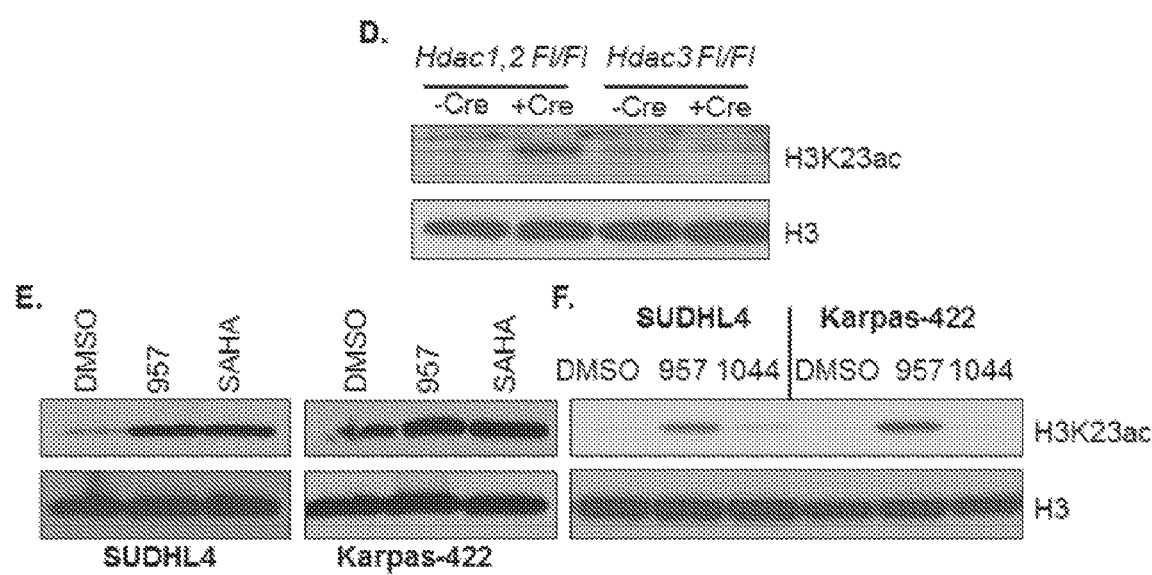
FIG. 2 (con't)

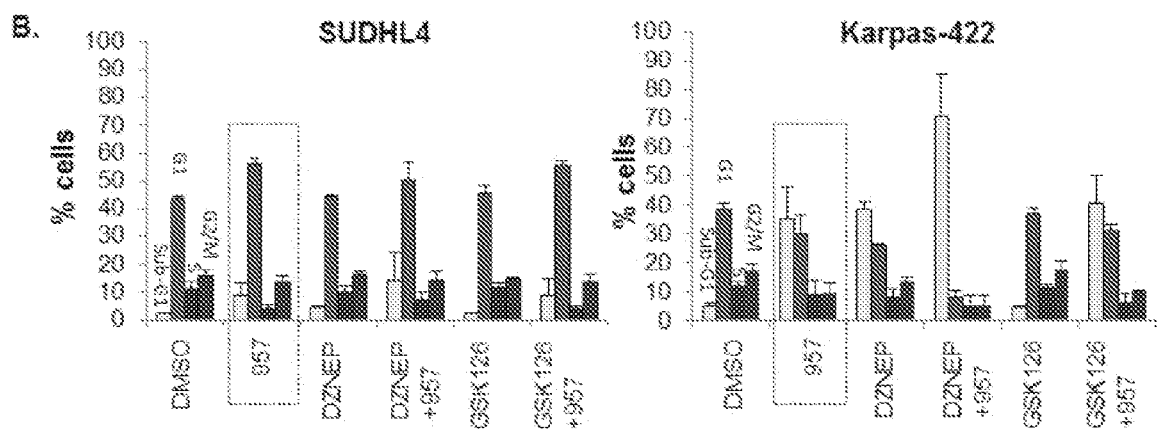
FIG. 3 (con't)

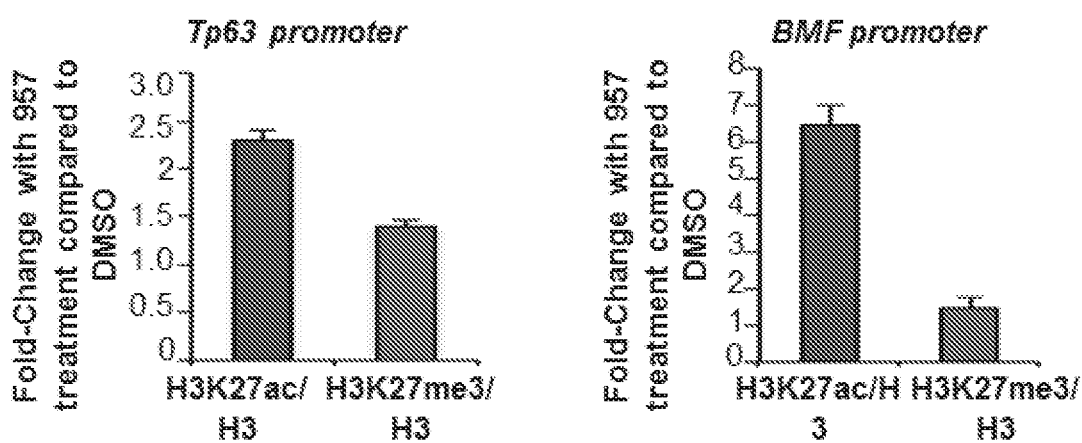
FIG. 5 (con't)

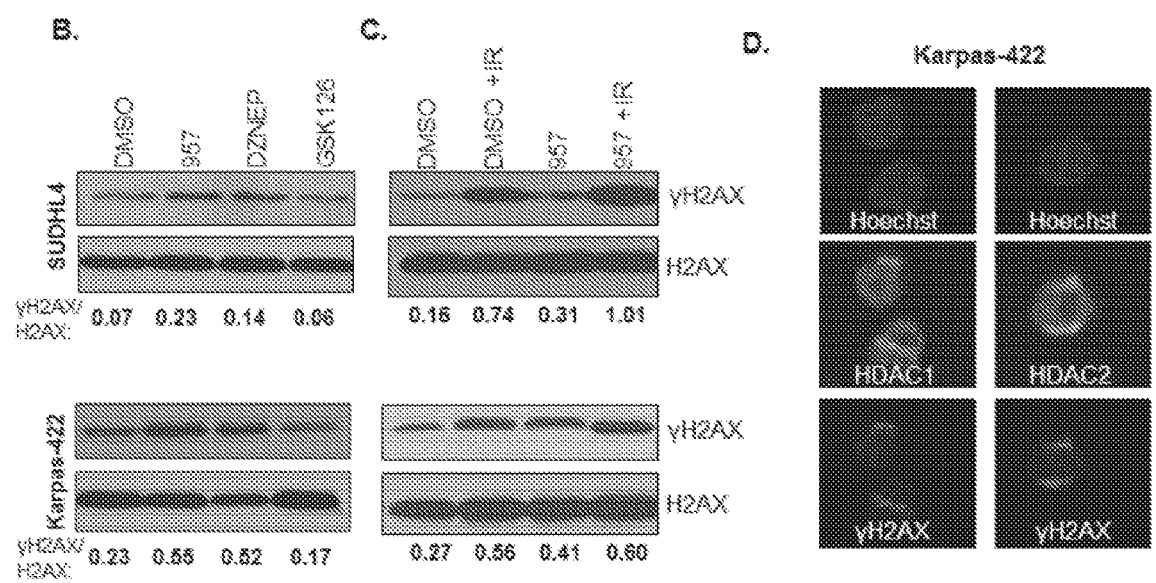
FIG. 6 (con't)

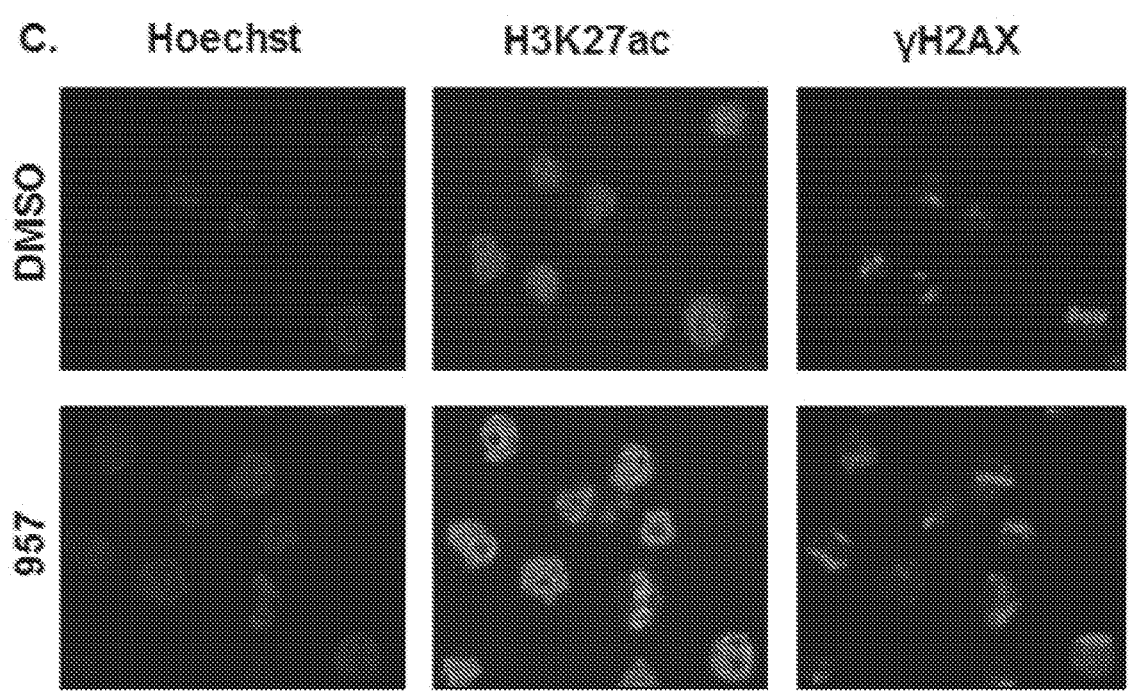
FIG. 7 (con't)

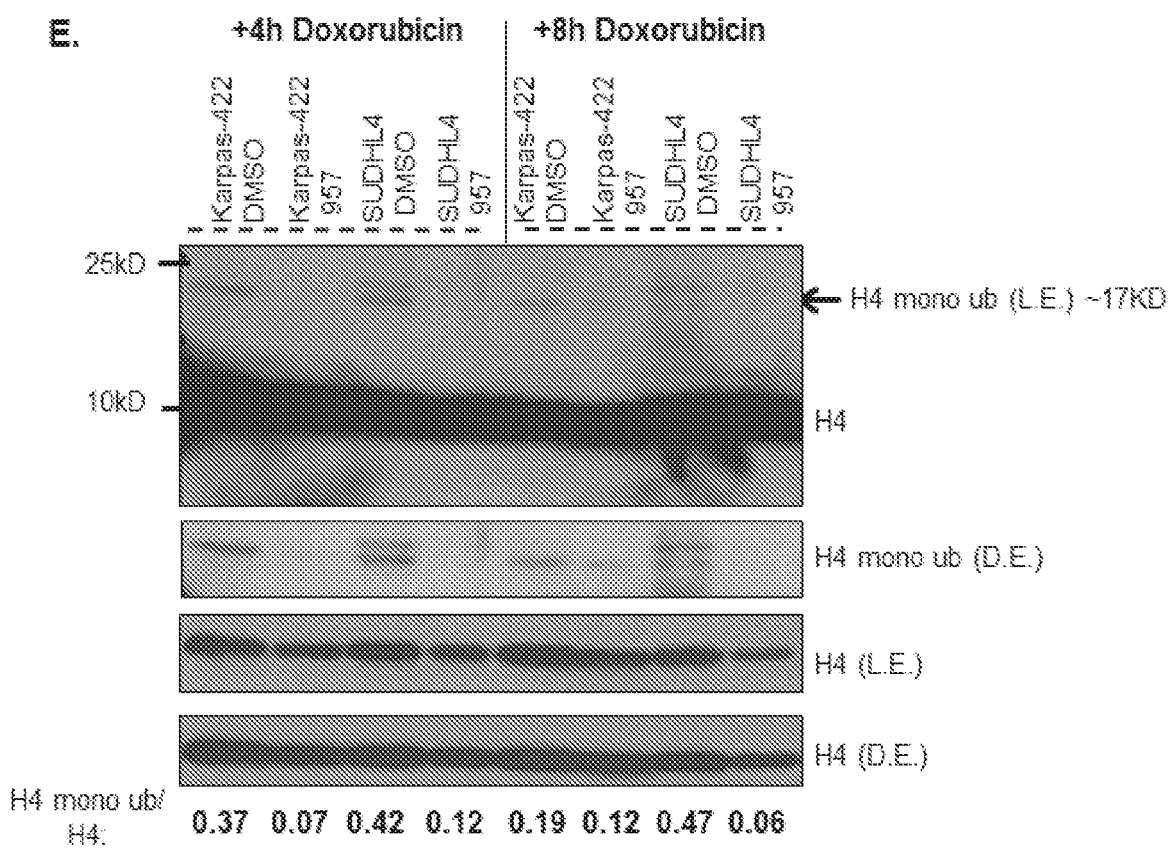
FIG. 8 (con't)

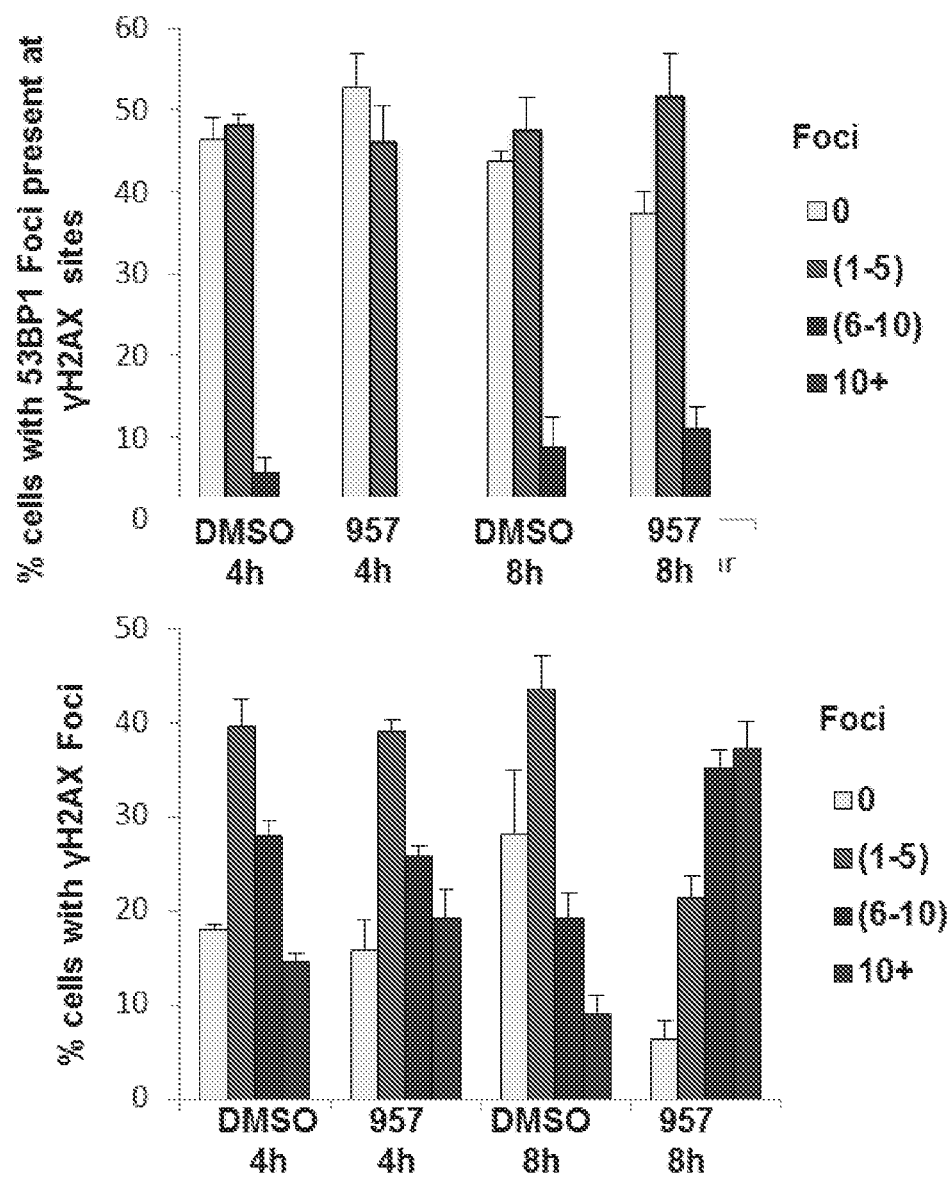
FIG. 9 (con't)

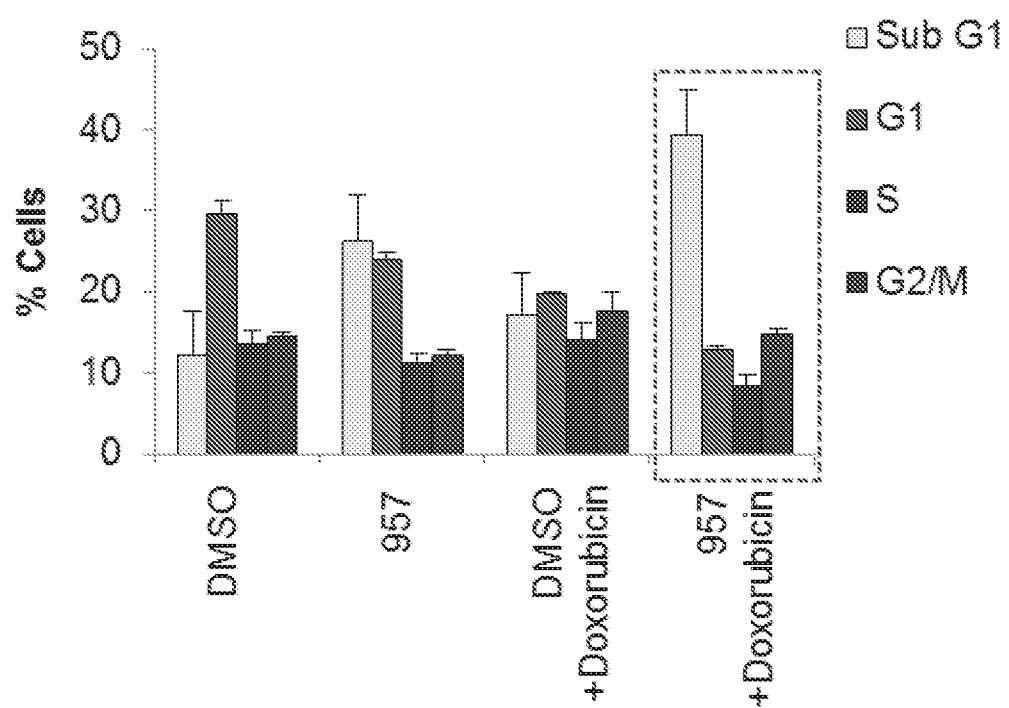
FIG. 10 (con't)

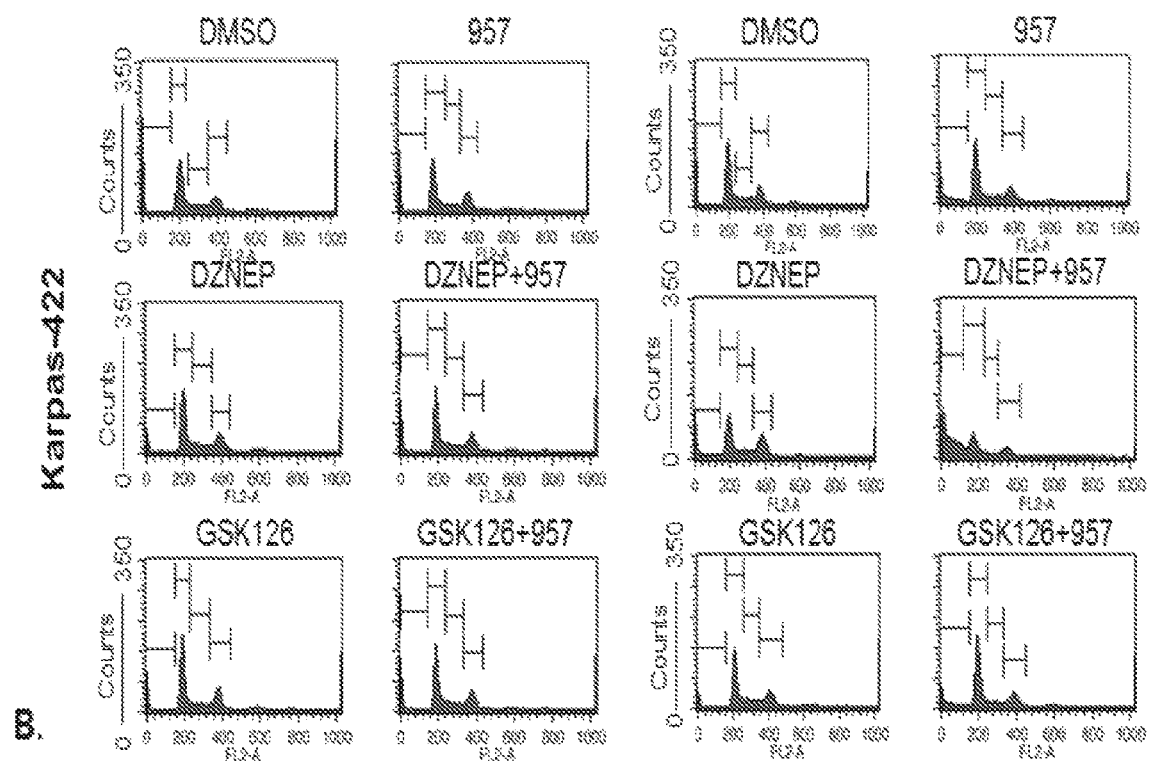
FIG. 13 (con't)

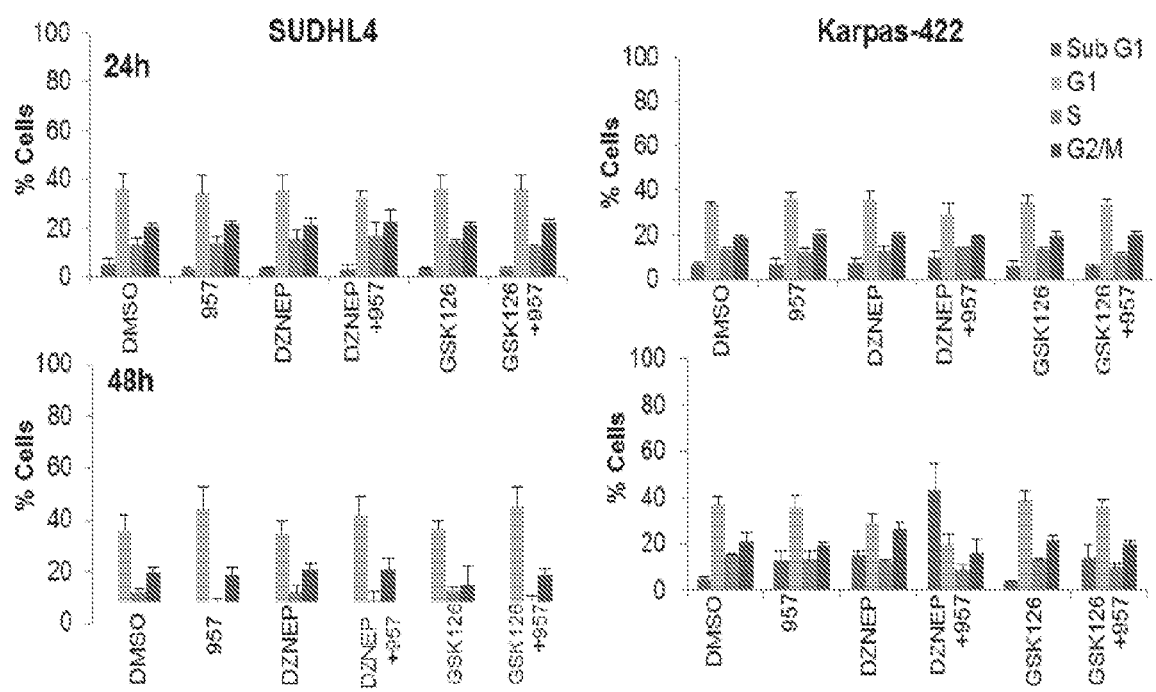
FIG. 13 (con't)

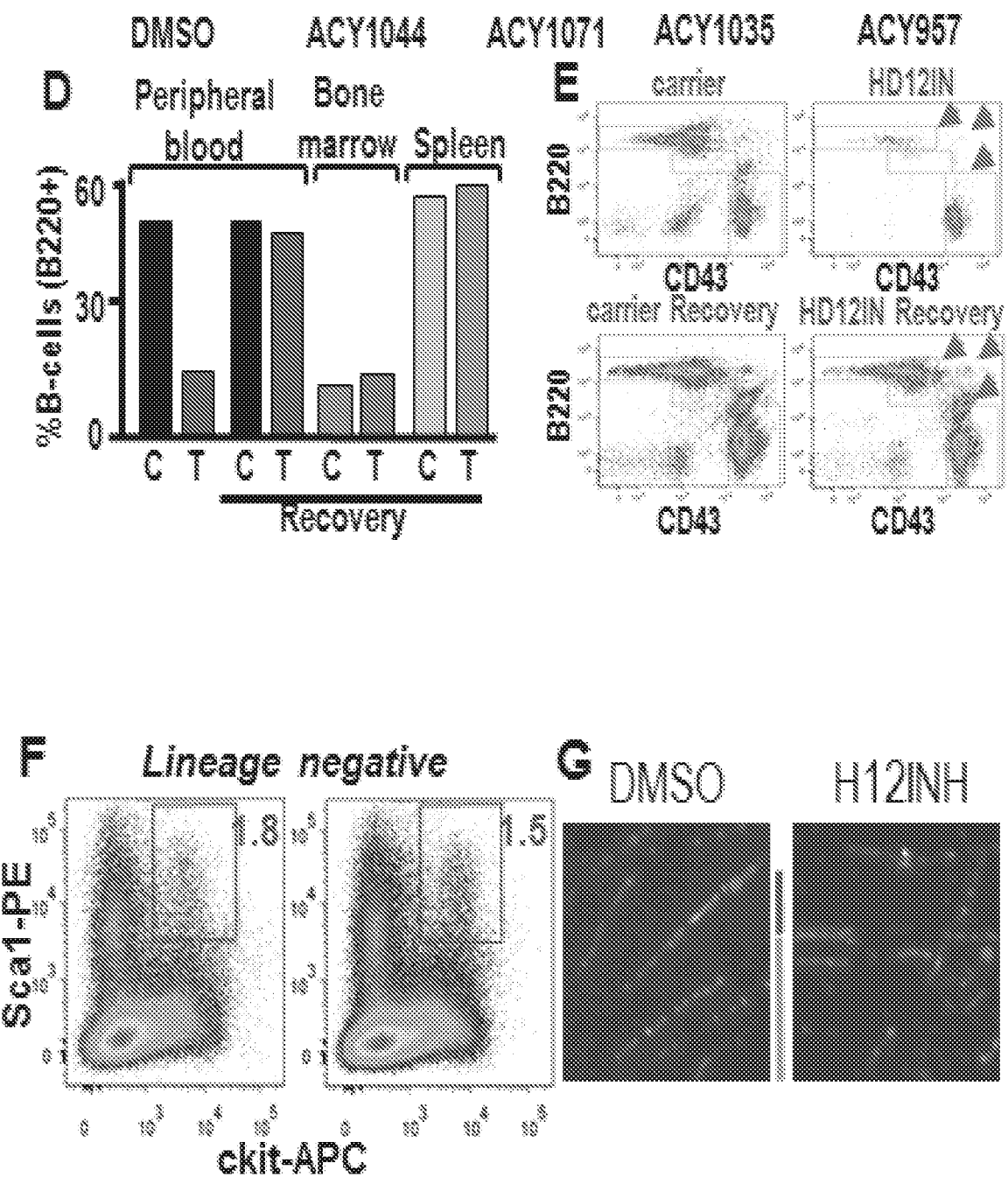
FIG. 20 (con't)

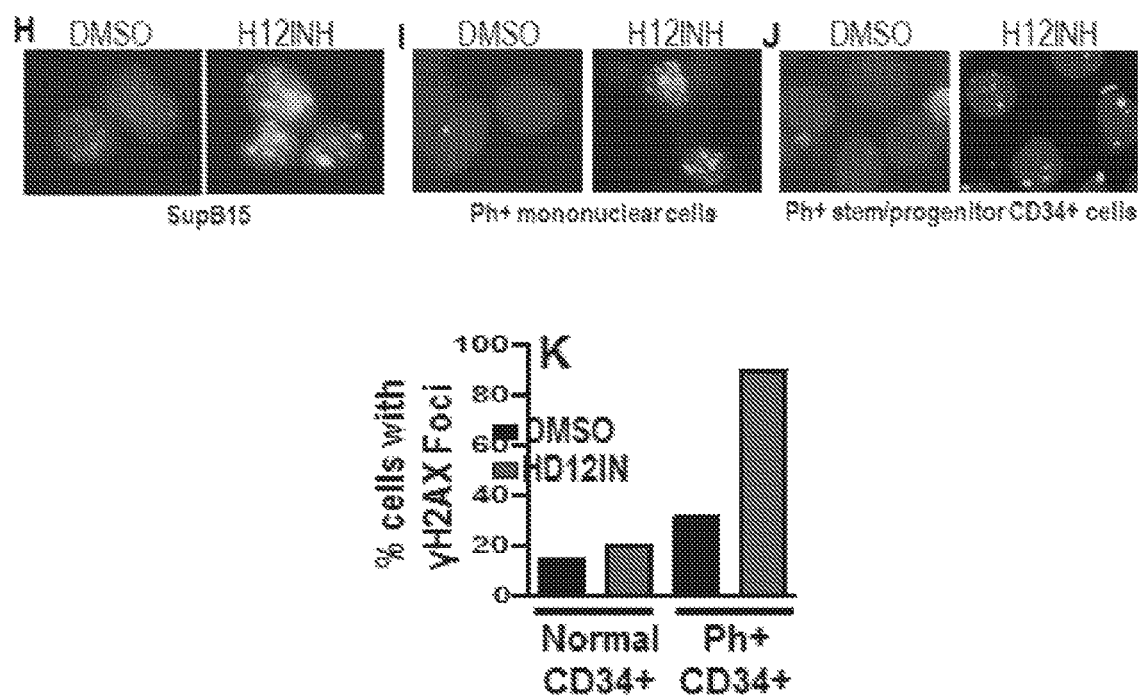
FIG. 20 (con't)

A.

| Primary Protein Name | Protein Description | Peptide Count | Dox vs DMSO | Treated versus DMSO | TDox versus Treated | TDox versus Dox | Error weighted ANOVA (w/FDR) all groups |
|---|---|---|---|---|---|---|---|
| WDHD1 | WD repeat and HMG-box DNA-binding protein 1 | 5 | -4.4 | 1 | -4.5 | -1 | 7.99E-14 |
| FA60A | Protein FAM60A | 2 | -2.7 | -1.4 | -4.3 | -2.3 | 7.50E-15 |
| RNH2A | Ribonuclease H2 subunit A | 3 | -2.5 | -1.2 | -4.3 | -2 | 1.56E-07 |
| PRI2 | DNA primase large subunit | 2 | -3 | 1.1 | -4 | -1.2 | 2.00E-03 |
| PAF15 | PCNA-associated factor | 6 | -2.4 | -1 | -3.6 | -1.5 | 7.50E-15 |
| DPOA2 | DNA polymerase alpha subunit B | 5 | -3.4 | 1.1 | -3.3 | 1.2 | 2.87E-07 |
| RNH2C | Ribonuclease H2 subunit A | 2 | -2.1 | 1 | -3.2 | -1.5 | 6.44E-07 |
| DNLI1 | DNA ligase 1 | 14 | -2.5 | -1.2 | -2.9 | 1.2 | 7.50E-15 |
| NOG2 | Nucleolar GTP-binding protein 2 | 9 | -2.2 | 1 | -2.8 | -1.5 | 7.50E-15 |
| BTF3 | Transcription factor BTF3 | 5 | -2 | 1.1 | -2.7 | -1.4 | 2.00E-03 |
| SUV91 | Histone-lysine N-methyltransferase SUV39H1 | 3 | -2.1 | -1.2 | -2.6 | -1.3 | 8.96E-10 |
| CDCA7 | Cell division cycle-associated protein 7 | 5 | -2.1 | -1 | -2.6 | -1.2 | 7.50E-15 |
| UHRF1 | E3 ubiquitin-protein ligase UHRF1 | 23 | -2.1 | -1.1 | -2.6 | -1.2 | 7.50E-15 |
| CA131 | Uncharacterized protein C1orf131 homolog | 3 | -2 | -1.2 | -1.2 | -1.5 | 2.36E-05 |
| PCNA | Proliferating cell nuclear antigen | 17 | -2.3 | -1.1 | -1.1 | -1.1 | 7.50E-15 |
| CC115 | Coiled-coil domain-containing protein 115 | 3 | -1.8 | -1.2 | -1.2 | -1.5 | 2.46E-04 |
| MCM2 | DNA replication licensing factor MCM2 | 20 | -2.6 | 1.1 | 1.1 | 1.3 | 2.69E-10 |
| MCM6 | DNA replication licensing factor MCM6 | 25 | -2.7 | 1.1 | 1.1 | 1.4 | 2.72E-13 |
| MTG16 | Protein CBFA2T3 | 9 | -1.8 | 1.2 | 1.2 | -1.2 | 7.50E-15 |
| UB2D3 | Ubiquitin-conjugating enzyme E2D3 | 3 | -1.8 | 1.1 | 1.1 | -1.1 | 1.80E-08 |
| HNRL1 | Heterogeneous nuclear ribonucleoprotein U-like protein 1 | 4 | -1.7 | 1.1 | 1.1 | -1.2 | 7.50E-15 |
| MCM7 | DNA replication licensing factor MCM7 | 24 | -2.5 | 1.1 | 1.1 | 1.3 | 5.70E-12 |
| MCM4 | DNA replication licensing factor MCM4 | 25 | -2.4 | 1.1 | 1.1 | 1.3 | 2.28E-13 |
| PINX1 | PIN2/TERF1-interacting telomerase inhibitor 1 | 2 | -2.1 | -1.3 | -1.3 | -1.3 | 2.94E-13 |
| UBP7 | Ubiquitin carboxyl-terminal hydrolase 7 | 12 | -2 | -1.1 | -1.1 | -1.1 | 7.50E-15 |
| PWP1 | Periodic tryptophan protein 1 homolog | 7 | -1.5 | 1 | 1 | -1.3 | 7.50E-15 |
| NACAM | Nascent polypeptide-associated complex subunit alpha | 4 | -1.6 | 1.3 | 1.3 | 1 | 5.20E-08 |
| MCM3 | DNA replication licensing factor MCM3 | 30 | -2.1 | 1.1 | 1.1 | 1.2 | 3.56E-12 |
| MCM5 | DNA replication licensing factor MCM5 | 20 | -2.2 | 1.1 | 1.1 | 1.3 | 7.50E-15 |
| S38A2 | Sodium-coupled neutral amino acid transporter 2 | 2 | -2 | 1.1 | 1.1 | 1.1 | 2.15E-05 |

B.

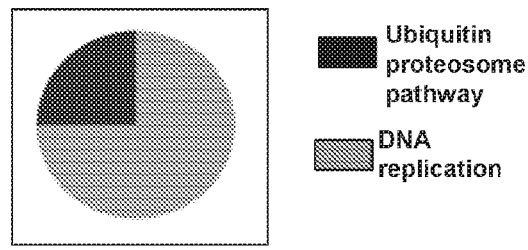

■ Ubiquitin proteosome pathway

▨ DNA replication

C.

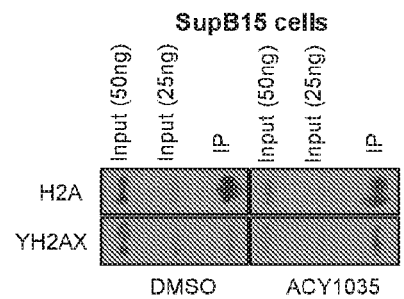

FIG. 29

# HDAC1,2 INHIBITORS AND METHODS OF USING THE SAME

CROSS-REFERENCE TO RELATED APPLICATIONS

This application is a continuation of U.S. patent application Ser. No. 15/541,012, filed on Jun. 29, 2017, which is a U.S. national stage entry of International Patent Application No. PCT/US2015/067883, filed on Dec. 29, 2015, which claims priority to U.S. Provisional Patent Application No. 62/097,727, filed on Dec. 30, 2014, the entire contents of each of which are fully incorporated herein by reference.

TECHNICAL FIELD

The present invention relates to an agent that selectively inhibits HDAC1 and HDAC2, a method of treating a cancer, a method of sensitizing a cancer to a chemotherapeutic agent, a method for determining if a cancer is sensitive to an agent that selectively inhibits HDAC1 and HDAC2, and a method for monitoring the efficacy of a treatment for a cancer.

BACKGROUND

Histone deacetylases (HDACs) remove acetyl groups from certain amino acid side chains of histone and non-histone proteins. The presence or absence of these acetyl groups often results in the regulation of the target protein and its cognate genetic or biochemical pathway. Aberrant activity or recruitment of HDACs to the target protein results in misregulation and in some instances, promotes the formation and/or growth of cancer.

SAHA and Depsipeptide are pan HDAC inhibitors that have been used in cancer treatment. However, given their lack of selectivity towards specific HDACs, SAHA and Depsipeptide inhibit multiple HDACs and thus, affect multiple cellular functions and thus, result in numerous side effects.

Accordingly, a need exists for the identification of selective HDAC inhibitors to facilitate treatment of cancer with less side effects and markers that identify cancers which are susceptible to such selective HDAC inhibitors to facilitate treatment decisions for the cancer patient.

SUMMARY

The present disclosure provides methods of treating cancer characterized by BCR-ABL expression or BBAP overexpression in a subject in need thereof comprising administering to the subject an agent that selectively inhibits HDAC1 and HDAC2.

The present disclosure also provides methods of sensitizing a cancer characterized by BCR-ABL expression or BBAP overexpression to a chemotherapeutic agent in a subject in need thereof, the method comprising administering an agent that selectively inhibits HDAC1 and HDAC2 to the subject. In some embodiments, the methods may further comprise administering doxorubicin to the subject.

The present disclosure further provides methods for determining if a cancer is sensitive to an agent that selectively inhibits HDAC1 and HDAC2 comprising: (a) obtaining a sample from a subject suffering from the cancer; (b) measuring a level of one or more markers in the sample, wherein the one or more markers are selected from the group consisting of BCR-ABL and BBAP; (c) comparing the measured level of the one or more markers in the sample to a level of the one or more markers in a control sample; and (d) determining that the cancer is sensitive to the agent when the measured level of the one or more markers in the sample is increased relative to the level of the one or more markers in the control sample.

The present disclosure further provides methods for monitoring the efficacy of a treatment for a cancer that includes administration of an agent that selectively inhibits HDAC1 and HDAC2, the method comprising: (a) obtaining a first sample from the subject before the treatment and a second sample from the subject during or after the treatment; (b) measuring a first level of one or more markers in the first sample and a second level of the one or more markers in the second sample, wherein the one or more markers are selected from the group consisting of 53BP1 and γH2AX; (c) comparing the first level of the one or more markers and the second level of the one or more markers; and (d) determining that the treatment is effective when the second level of the one or more markers is higher than the first level of the one or more markers.

BRIEF DESCRIPTION OF THE DRAWINGS

FIG. 2 shows characterization of selective HDAC1,2 inhibitor in EZH2 gain-of-function mutant DLBCL cells: (A): In vitro enzyme assays using recombinant HDAC proteins to determine the specificity of ACY-957 and ACY-1044 towards HDAC1, 2 and 3. Numbers in the table represented $IC_{50}$ values obtained for an inhibitor-enzyme combination in the in vitro HDAC assays at a 95% confidence level. Compounds were diluted in DMSO to 50 fold the final concentration and a ten point three fold dilution series was made. The compounds were diluted in assay buffer (50 mM HEPES, pH 7.4, 100 mM KCl, 0.001% Tween-20, 0.05% BSA, 20 µM tris(2-carboxyethyl)phosphine) to 6 fold their final concentration. The HDAC enzymes (purchased from BPS Biosciences) were diluted to 1.5 fold their final concentration in assay buffer. The tripeptide substrate (synthesized in house) and trypsin at 0.05 µM final concentration were diluted in assay buffer at 6 fold their final concentration. Five µl compounds and 20 µl of enzyme were added to wells of a black, opaque 384 well plate in duplicate. Enzyme and compound were incubated together at room temperature for 10 minutes. Five µl of substrate was added to each well, the plate was shaken for 60 seconds and placed into a Victor 2 microtiter plate reader. The development of fluorescence was monitored for 60 min and the linear rate of the reaction was calculated. The $IC_{50}$ was determined using Graph Pad Prism by a four parameter curve fit. SUDHL4 (B) and Karpas-422 (C) cells were treated with increasing amounts of ACY957 and whole cell lysates were prepared following a 24 hr treatment. Western blot analysis of H3K9K14ac and H4K5ac was done. Histone H3 and H4 were used as controls. (D): Western blot analysis of whole cell lysate prepared from HDAC1Fl/Fl, HDAC2Fl/Fl or HDAC3Fl/Fl fibrosarcoma cells following Ad-Cre infection. Lysates were prepared 72 h post Ad-Cre infection. (E): SUDHL4 and Karpas-422 cells were treated with DMSO, 2 µM ACY-957 or 2 µM SAHA for 24 hours and western blot analysis of whole cell lysate with anti-H3K23ac was done. Histone H3 served as the loading control. (F): SUDHL4 and Karpas-422 cells were treated with either DMSO, 2 μM ACY-957 or 2 μM ACY-1044 and western analysis with anti-H3K23ac was performed.

FIG. 29 shows (A) proteins that decreased on the chromatin following ACY1035+doxorubicin treatment when compared to ACY1035 treatment alone in mass spectrometry analysis; (B) Panther analysis demonstrating that the majority of proteins identified in mass spectrometry analysis that are affected upon doxorubicin treatment belong to DNA replication; and (C) increased DNA damage on nascent chromatin in SupB15 cells as identified by BrdU-ChIP-slot assay.

DETAILED DESCRIPTION

Figure 1:
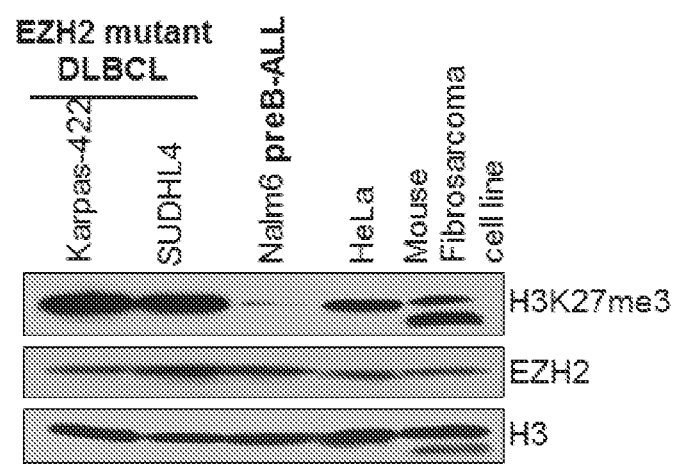
FIG. 1 shows the levels of histone H3K27me3 in EZH2 gain-of-function mutant DLBCL cells when compared to other cancer cell lines: Western blot analysis of whole cell lysates prepared from Karpas-422, SUDHL4, NALM6, HeLa and mouse fibrosarcoma cells was performed with anti-H3K27me3 and anti-EZH2 antibodies. Histone H3 served as a loading control.

The methods of the present disclosure generally include administration of an agent that selectively inhibits HDAC1 and HDAC2 (i.e., an HDAC1,2 inhibiting agent). This selective inhibition of HDAC1,2 was found to decrease double-stranded break (DSB) repair and to activate the DNA damage response in cancer cells. This caused damaged DNA to accumulate in the cancer cells, thereby causing cytotoxic or cytostatic effects in the cancer cells. This inhibition also was found to further sensitize the cancer cells to a chemotherapeutic agent.

Accordingly, the present disclosure provides methods of treating a cancer and methods of sensitizing a cancer to the chemotherapeutic agent, each comprising administering the agent that selectively inhibits HDAC1 and HDAC2 to a subject in need thereof.

The present disclosure further provides methods for determining if a cancer may be sensitive to an agent that selectively inhibits HDAC1 and HDAC2, as well as methods for monitoring the efficacy of a treatment for a cancer, where the treatment includes administering the agent, which selectively inhibits HDAC1 and HDAC2. These methods each include measuring a level of one or more markers in a sample(s) obtained from a subject suffering from the cancer.

The one or more markers may include BCR-ABL, BBAP, 53BP1, γH2AX, EZH2 gain-of-function mutation, or any combination thereof. Depending on the measured level of the one or more markers, it is determined if the cancer is susceptible to the HDAC1,2 agent and/or if the treatment with the HDAC1,2 is effective.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The number of carbon atoms in a hydrocarbyl substituent can be indicated by the prefix "$C_{x-y}$," where x is the minimum and y is the maximum number of carbon atoms in the substituent. Likewise, a $C_x$ chain means a hydrocarbyl chain containing x carbon atoms.

The term "alkyl," as used herein, refers to saturated, straight- or branched-chain hydrocarbon moieties containing, in certain embodiments, between one and six, or one and eight carbon atoms, respectively. Examples of $C_{1-6}$ alkyl moieties include, but are not limited to, methyl, ethyl, propyl, isopropyl, n-butyl, tert-butyl, neopentyl, n-hexyl moieties; and examples of $C_{1-8}$ alkyl moieties include, but are not limited to, methyl, ethyl, propyl, isopropyl, n-butyl, tert-butyl, neopentyl, n-hexyl, heptyl, and octyl moieties.

The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denotes a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, idenyl and the like. In some embodiments, aryl groups have 6 carbon atoms. In some embodiments, aryl groups have from six to ten carbon atoms. In some embodiments, aryl groups have from six to sixteen carbon atoms.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The term "cycloalkyl," as used herein, denotes a monovalent group derived from a monocyclic or polycyclic saturated or partially unsaturated carbocyclic ring compound. Examples of $C_{3-8}$-cycloalkyl include, but are not limited to, cyclopropyl, cyclobutyl, cyclopentyl, cyclohexyl, cyclopentyl and cyclooctyl; and examples of $C_{3-12}$-cycloalkyl include, but are not limited to, cyclopropyl, cyclobutyl, cyclopentyl, cyclohexyl, bicyclo[2.2.1]heptyl, and bicyclo[2.2.2]octyl. Also contemplated are monovalent groups derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like. In some embodiments, cycloalkyl groups have from three to six carbon atoms. In some embodiments, cycloalkyl groups have from three to eight carbon atoms.

The terms "halo" and "halogen," as used herein, refer to an atom selected from fluorine, chlorine, bromine and iodine.

The term "heteroaryl," as used herein, refers to a mono- or poly-cyclic (e.g., bi-, or tri-cyclic or more) fused or non-fused, moieties or ring system having at least one aromatic ring, having from five to ten ring atoms of which one ring atom is selected from oxygen, sulfur, and nitrogen; zero, one or two ring atoms are additional heteroatoms independently selected from oxygen, sulfur, and nitrogen; and the remaining ring atoms are carbon. In some embodiments, the heteroaryl group has from about one to six carbon atoms, and in further embodiments from one to fifteen carbon atoms. In some embodiments, the heteroaryl group contains five to sixteen ring atoms of which one ring atom is selected from oxygen, sulfur, and nitrogen; zero, one, two, or three ring atoms are additional heteroatoms independently selected from oxygen, sulfur, and nitrogen; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

Any of the aryls, substituted aryls, heteroaryls and substituted heteroaryls described herein, can be any aromatic group. Aromatic groups can be substituted or unsubstituted.

The term "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur, and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In an embodiment, the heterocycloalkyl group is a 4-7, e.g., 4-6, membered ring. The term "subject" or "patient" as used herein interchangeably, means any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc)) and a human. In some embodiments, the subject or patient may be a human or a non-human. The subject or patient may be undergoing other forms of treatment. In some embodiments, the subject or patient may be a human subject at risk for developing or already having cancer.

The term "sample," "test sample," "specimen," "biological sample," "sample from a subject," or "subject sample" as used herein interchangeably, means a sample or isolate of blood, tissue, urine, serum, plasma, amniotic fluid, cerebrospinal fluid, placental cells or tissue, endothelial cells, leukocytes, or monocytes, can be used directly as obtained from a subject or can be pre-treated, such as by filtration, distillation, extraction, concentration, centrifugation, inactivation of interfering components, addition of reagents, and the like, to modify the character of the sample in some manner as discussed herein or otherwise as is known in the art.

The term also means any biological material being tested for and/or suspected of containing an analyte of interest. The sample may be any tissue sample taken or derived from the subject. In some embodiments, the sample from the subject may comprise protein. In some embodiments, the sample from the subject may comprise nucleic acid. Any cell type, tissue, or bodily fluid may be utilized to obtain a sample. Such cell types, tissues, and fluid may include sections of tissues such as biopsy (such as muscle biopsy) and autopsy samples, frozen sections taken for histological purposes, blood (such as whole blood), plasma, serum, sputum, stool, tears, mucus, saliva, hair, skin, red blood cells, platelets, interstitial fluid, ocular lens fluid, cerebral spinal fluid, sweat, nasal fluid, synovial fluid, menses, amniotic fluid, semen, etc. Cell types and tissues may also include muscle tissue or fibres, lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose). Archival tissues, such as those having treatment or outcome history, may also be used. Protein or nucleotide isolation and/or purification may not be necessary.

Methods well-known in the art for collecting, handling and processing muscle tissue or fibre, urine, blood, serum and plasma, and other body fluids, are used in the practice of the present disclosure. The test sample can comprise further moieties in addition to the analyte of interest, such as antibodies, antigens, haptens, hormones, drugs, enzymes, receptors, proteins, peptides, polypeptides, oligonucleotides or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary (e.g., most urine samples, a pre-processed archived sample, etc.), pretreatment of the sample is an option that can be performed for mere convenience (e.g., as part of a protocol on a commercial platform). The sample may be used directly as obtained from the subject or following pretreatment to modify a characteristic of the sample. Pretreatment may include extraction, concentration, inactivation of interfering components, and/or the addition of reagents.

"Treat", "treating" or "treatment" are each used interchangeably herein to describe reversing, alleviating, or inhibiting the progress of a disease, or one or more symptoms of such disease, to which such term applies. A treatment may be either performed in an acute or chronic way. The term also refers to reducing the severity of a disease or symptoms associated with such disease after affliction with the disease. "Treatment" and "therapeutically," refer to the act of treating, as "treating" is defined above.

As described herein, the disclosed compounds may optionally be substituted with one or more substituents, such as are illustrated generally above, or as exemplified by particular classes, subclasses, and species. It will be appreciated that the phrase "optionally substituted" is used interchangeably with the phrase "substituted or unsubstituted." In general, the term "substituted," whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted" and any other optionally substituted group as used herein, refer to groups that are substituted or unsubstituted by independent replacement of one, two, or three or more of the hydrogen atoms thereon with substituents including, but not limited to:

alkyl, alkenyl, alkynyl, cycloalkyl, aryl, heterocycloalkyl, heteroaryl,

—F, —Cl, —Br, —I,

—OH,

—NO$_2$, —CN,

—NH$_2$, —NH—C$_{1\text{-}12}$-alkyl, —NH-aryl, -dialkylamino,

—O—C$_1$-C$_{12}$-alkyl, —O-aryl,

—O(O)—, —O(O)O—, —C(O)NH—, —OC(O)—, —OC(O)O—, —OC(O)NH—, —NHC(O)—, —NHC(O)O—,

—O(O)—C$_{1\text{-}12}$-alkyl, —O(O)—C$_{3\text{-}12}$-cycloalkyl, —C(O)-aryl, —C(O)-heteroaryl, —O(O)-heterocycloalkyl, —O(O)O—C$_{1\text{-}12}$-alkyl, —O(O)O—C$_{3\text{-}12}$-cycloalkyl, —O(O)O-aryl, —O(O)O-heteroaryl, C(O)O-heterocycloalkyl, —CONH$_2$, —CONH—C$_1$-C$_{12}$-alkyl, —CONH-aryl, —OCO$_2$—OCO$_2$-aryl, —OCONH$_2$, —OCONH—OCONH-aryl, —NHC(O)—C$_{1\text{-}12}$-alkyl, —NHC(O)-aryl, —NHCO$_2$—C$_{1\text{-}12}$-alkyl, —NHCO$_2$-aryl, —S(O)—C$_{1\text{-}12}$-alkyl, —S(O)-aryl, —SO$_2$NH—C$_{1\text{-}12}$-alkyl, —SO$_2$NH-aryl, —NHSO$_2$—C$_{1\text{-}12}$-alkyl, —NHSO$_2$-aryl, —SH, —S—C$_{1\text{-}12}$-alkyl, or —S-aryl.

In certain embodiments, the optionally substituted groups include the following: C$_{1\text{-}12}$-alkyl, C$_{2\text{-}12}$-alkenyl, C$_{2\text{-}12}$-alkynyl, C$_{3\text{-}12}$-cycloalkyl, C$_{3\text{-}12}$-aryl, C$_{3\text{-}12}$-heterocycloalkyl, or C$_{3\text{-}12}$-heteroaryl.

It is understood that the aryls, heteroaryls, alkyls, and the like can be further substituted.

2. HDAC1,2 Inhibiting Agent

This disclosure provides methods that comprise the use of one or more histone deacetylase (HDAC) 1,2 inhibiting agents, which include any compound or composition that selectively inhibits the deacetylase activity of HDAC1, HDAC2, or both HDAC1 and HDAC2. This selective inhibition of HDAC1 and HDAC2 may kill cancer cells, or may inhibit or prevent growth of cancer cells, as described in more detail below. The HDAC1,2 agent also may sensitize cancer cells to a chemotherapeutic agent.

HDAC1,2 inhibiting agents that may be used for the methods of the present disclosure may include, but are not limited to, those disclosed in U.S. Patent Application Publication No. 2014/0128391 and U.S. Pat. No. 9,145,412, the complete disclosures of which are hereby incorporated by reference for all purposes. Specific examples of HDAC1,2 inhibiting agents may include, but are not limited to, ACY-957, ACY-1035, ACY-1071, pharmaceutically acceptable salts thereof, and combinations thereof. Each of these compounds is described in more detail below.

a. HDAC1 and HDAC2 Activity

As described above, the HDAC1,2 inhibiting agent selectively inhibits HDAC1 and HDAC2. HDAC1 and HDAC2 each belong to the class I HDAC family and interact with the polycomb repression complex (PRC), which contains EZH2 as the catalytic subunit. Aberrant HDAC1 and HDAC2 activity and/or recruitment to genomic loci or target proteins may contribute to misregulated gene expression, and thus, cancer.

As demonstrated herein, selective inhibition with HDAC1,2 inhibiting agents caused cytotoxic or cytostatic effects in DLBCL cells that had a gain-of-function mutation in EZH2 ($EZH2^{GOF}$). Blocking the activities of HDAC1,2 increased global H3K27ac without causing a concomitant global decrease in H3K27me3 levels. As also demonstrated herein, inhibition with HDAC1,2 inhibiting agents was sufficient to decrease H3K27me3 present at double-stranded breaks (DSBs), decrease DSB repair and activate the DNA damage response in these DLBCL cells. As also demonstrated herein, selective inhibition with HDAC1,2 inhibiting agents in B-cell malignant cells led to increased numbers of foci containing γH2AX; such foci mark DNA damage.

As further demonstrated herein, selective inhibition with HDAC1,2 inhibiting agents increased H4K91ac, decreased BBAP-mediated H4K91 monoubiquitination, impaired BBAP-dependent double strand break (DSB) repair and sensitized the refractory $EZH2^{GOF}$ DLBCL cells to treatment with the chemotherapeutic agent (e.g., doxorubicin). Hence, selective Hdacs1,2 inhibition provided a DNA repair mechanism-based therapeutic approach as it overcame both EZH2- and BBAP-mediated DSB repair in the $EZH2^{GOF}$ DLBCL cells.

Figure 15:
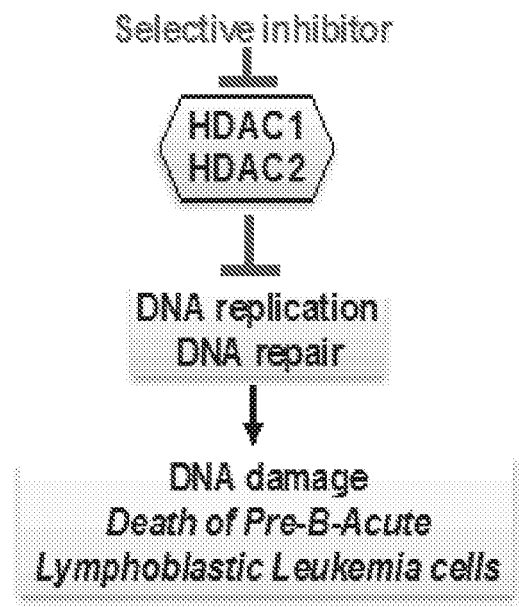
FIG. 15 shows a model for the mode-of-action of the HDAC1,2 agent in Pre-B-ALL leukemic cells.
Figure 16:
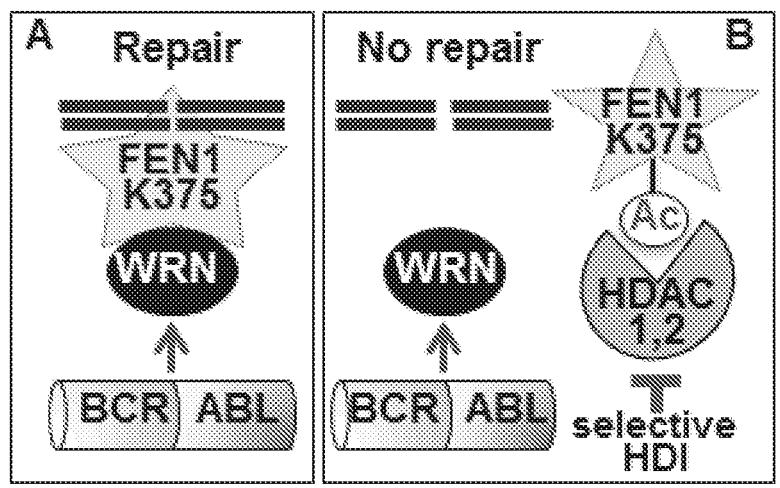
FIG. 16 shows a model for HDAC1,2 selective inhibitor action in Pre-B-ALL cells. (A). WRN interacted with FEN1 via lysine (K) 375 residue. BCR-ABL stimulated WRN and FEN1 activities for hyperactive DNA repair and protected leukemic cells. (B). HDAC1,2 inhibition increased FEN1-K375 acetylation and disrupted FEN1 interaction with WRN. This overrided BCR-ABL-mediated stimulation resulting in DNA breaks and cell death.

As also demonstrated herein, acetylation of FEN1 was increased upon selective inhibition of HDAC1,2, which in turn, prevented DNA repair that was mediated by BCR-ABL and WRN (FIG. 16). This inhibition of DNA repair caused DNA damage to accumulate and death of Pre-B-acute-lymphoblastic leukemia (Pre-B-ALL) cells (FIG. 15).

b. HDAC1, 2 Inhibiting Agents

In some embodiments, a compounds according to the following Formula I, or a pharmaceutically acceptable salt thereof, may be used as an HDAC1, 2 inhibiting agent:

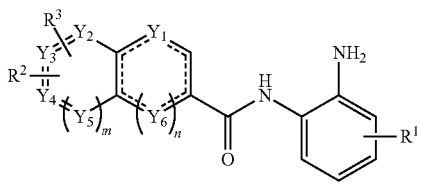

wherein $Y_1$ is $CR^7$ or $NR^7$;
$Y_2$, $Y_3$, $Y_4$, $Y_5$, and $Y_6$ are each independently CH, $CH_2$, N, or C(O), wherein at least one of $Y_2$, $Y_3$, $Y_4$, and $Y_5$ are CH;
$R^1$ is mono-, bi-, or tri-cyclic aryl or heteroaryl, wherein the mono-, bi-, or tri-cyclic aryl or heteroaryl is optionally substituted;
$R^2$ and $R^3$ are each independently selected from $C_{2-6}$-alkenyl, $C_{2-6}$-alkynyl, $C_{3-6}$-cycloalkyl, $C_{1-6}$-alkyl-$C_{3-6}$-cycloalkyl, heterocyclo alkyl, $C_{1-6}$-alkyl-heterocycloalkyl, $NR^4R^5$, O—$C_{1-6}$-alkyl-$OR^6$, $C_{1-6}$-alkyl-$OR^6$, aryl, heteroaryl, C(O)N(H)-heteroaryl, C(O-heteroaryl, C(O-heterocycloalkyl, C(O-aryl, C(O)—$C_{1-6}$-alkyl, $CO_2$—$C_{1-6}$-alkyl, or C(O)—$C_{1-6}$-alkyl-heterocycloalkyl, wherein the cycloalkyl, heterocycloalkyl, aryl, or heteroaryl is optionally substituted;
$R^4$ is H, $C_{1-6}$-alkyl, or $C_{1-6}$-alkyl-$OR^6$;
$R^5$ is $CO_2R^6$, $C_1$-$C_6$-alkyl-aryl, or $C_{1-6}$-alkyl-$OR^6$;
$R^6$ is H or $C_{1-6}$-alkyl;
$R^7$ is null, H, $C_{1-6}$-alkyl, $C_{3-6}$-cycloalkyl, $C_{1-6}$-alkyl-$C_{3-6}$-cycloalkyl, heterocycloalkyl, or $C_{1-6}$-alkyl-heterocycloalkyl;
a $=$ line denotes an optionally double bond;
m is 0 or 1; and
n is 0 or 1, provided at least one of m or n is 1.

In some embodiments, a compounds according to the following Formula II, or a pharmaceutically acceptable salt thereof, may be used as an HDAC1, 2 inhibiting agent:

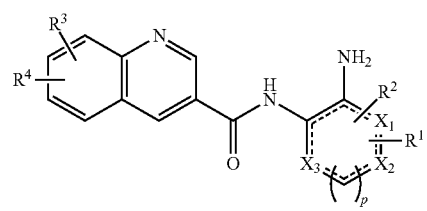

$R^1$ and $R^2$ are independently H, mono-, bi-, or tri-cyclic aryl or heteroaryl, wherein the mono-, bi-, or tri-cyclic aryl or heteroaryl is optionally substituted;
or $R^1$ and $R^2$ are linked together to form a group as shown below:

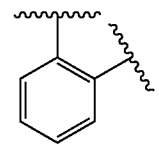 [SMILES: *c1ccccc1*]

$R^3$ and $R^4$ are independently selected from H, $C_{1-6}$-alkyl, $C_{2-6}$-alkenyl, $C_{2-6}$-alkynyl, $C_{3-6}$-cycloalkyl, $C_{1-6}$-alkyl-$C_{3-6}$-cycloalkyl, heterocyclo alkyl, $C_{1-6}$-alkyl-heterocycloalkyl, $NR^5R^6$, O—$C_{1-6}$-alkyl-$OR^7$, aryl, heteroaryl, C(O)N(H)-heteroaryl, C(O-heteroaryl, C(O-heterocycloalkyl, C(O)-aryl, C(O)—$C_{1-6}$-alkyl, CO.sub.2-$C_{1-6}$-alkyl, or C(O)—$C_{1-6}$-alkyl-heterocycloalkyl, wherein the cycloalkyl, heterocycloalkyl, aryl, or heteroaryl is optionally substituted;
$R^5$ is H, $C_{1-6}$-alkyl, $CO_2R^7$ or $C_{1-6}$-alkyl-$OR^7$;
$R^6$ is H, $C_{1-6}$-alkyl, $CO_2R^7$ or $C_{1-6}$-alkyl-$OR^7$;
$R^7$ is H or $C_{1-6}$-alkyl;
$X_1$, $X_2$, and $X_3$ are each independently CH, N, or S, wherein at least one of $X_1$ or $X_2$ is N or S;

a ⸺ line denotes an optionally double bond; and
p is 0 or 1.

c. ACY-957

ACY-957, or a pharmaceutically acceptable salt thereof, is an exemplary HDAC1,2 inhibiting agent that may be used in connection with the methods disclosed herein. ACY-957 also may be known herein as N-(2-amino-5-(thiophen-2-yl)phenyl)-2-(piperazin-1-yl)quinoline-6-carboxamide and have the following chemical structure:

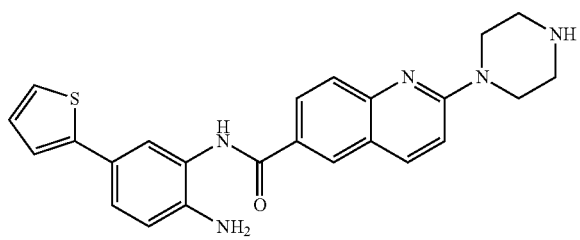 [SMILES: Nc1ccc(-c2cccs2)cc1NC(=O)c1ccc2nc(N3CCNCC3)ccc2c1]

d. ACY-1035

ACY-1035, or a pharmaceutically acceptable salt thereof, is another exemplary HDAC1,2 inhibiting agent that also may be used in connection with the methods disclosed herein. ACY-1035 may also be known herein as of N-(2-amino-5-(thiophen-2-yl)phenyl)-2-cyclopropyl-1-(2-morpholinoethyl)-1H-indole-5-carboxamide and have the following chemical structure:

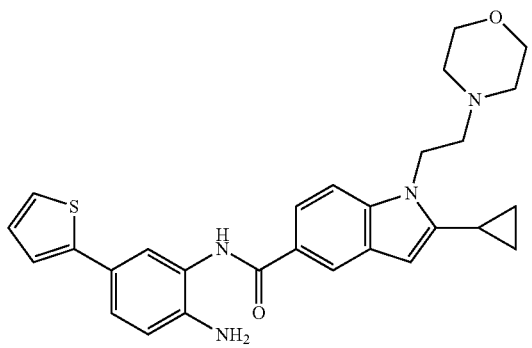 [SMILES: Nc1ccc(-c2cccs2)cc1NC(=O)c1ccc2c(c1)cc(C1CC1)n2CCN1CCOCC1]

e. ACY-1071

ACY-1071, or a pharmaceutically acceptable salt thereof, is another exemplary HDAC1,2 inhibiting agent that also may be used in connection with the methods disclosed herein. ACY-1071 may also be known herein as N-(2-amino-5-(pyridin-4-yl)phenyl)-2-cyclopropyl-1-(2-morpholinoethyl)-1H-indole-5-carboxamide and have the following chemical structure:

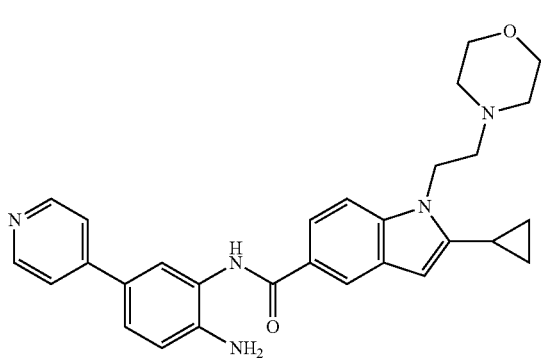 [SMILES: Nc1ccc(-c2ccncc2)cc1NC(=O)c1ccc2c(c1)cc(C1CC1)n2CCN1CCOCC1]

f. Pharmaceutical Compositions

The HDAC1,2 inhibiting agent may be incorporated into pharmaceutical compositions suitable for administration to a subject (such as a patient, which may be a human or non-human).

The pharmaceutical compositions may include a "therapeutically effective amount" or a "prophylactically effective amount" of the HDAC1,2 agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of the agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The pharmaceutical composition may include one or more pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

3. Methods of Treatment

This disclosure provides methods of treating cancer, that include administering one or more HDAC1,2 inhibiting agents to the subject. As described above, HDAC1,2 inhibiting agents may selectively inhibit HDAC1 and HDAC2, thereby killing a cancer cell, or inhibiting or preventing the growth of the cancer. The cancer may characterized by BCR-ABL expression, BBAP overexpression, by a gain-of-function mutation in Enhancer of Zeste Homologue 2 (EZH2), as being dependent upon a double-stranded break repair pathway, increased H3K27me3, or any combination thereof. The double-stranded break repair pathway may include FEN1.

In other embodiments, the cancer may be a B cell malignancy. The B cell malignancy may be characterized by BCR-ABL expression, BBAP overexpression, dependency upon the double-stranded break repair pathway, increased H3K27me3, or any combination thereof. The B cell malignancy may be diffuse large B cell lymphoma (DLBCL) or pre-B cell derived acute lymphoblastic leukemia (Pre-B-ALL). The DLBCL may contain a gain-of-function mutation in Enhancer of Zeste Homologue 2 (EZH2), a gain-of-function mutation in a histone H3K27 methyltransferase, a loss-of-function mutation in a H3K27 demethylase, or any combination thereof. The Pre-B-ALL may contain a chromosomal translocation, for example, but not limited to, t(9;22); such a Pre-B-ALL may also be referred to as Ph+Pre-B-ALL. The chromosomal translocation t(9;22) may encode the oncogenic protein BCR-ABL.

In some embodiments, the method of treating may apply the method for determining if the cancer is sensitive to the HDAC1,2 agent, which is described below in more detail. Accordingly, the method of treating may include detecting a level of BCR-ABL and a level of BBAP in a sample obtained from the subject. The method of treating may also include comparing the detected levels of BCR-ABL and BBAP to levels of BCR-ABL and BBAP in a control sample. If the detected level of BCR-ABL is increased relative to the control level of BCR-ABL, then the cancer may be characterized by BCR-ABL expression. If the detected level of BCR-ABL is not increased relative to the control level of BCR-ABL, then the cancer may not be characterized by BCR-ABL expression. If the detected level of BBAP is increased relative to the control level of BBAP, then the cancer may be characterized by BBAP overexpression. If the detected level of BBAP is not increased relative to the control level of BBAP, then the cancer may not be characterized by BBAP overexpression.

4. Methods of Sensitizing the Cancer to the Chemotherapeutic Agent

Also provided herein are methods of sensitizing a cancer to a chemotherapeutic agent. The chemotherapeutic agent may be doxorubicin or other components of the CHOP chemotherapy regimen (cyclophosphamide, vincistrine, Prednisone).

The method may include administering the HDAC1,2 inhibiting agent to the subject. HDAC1,2 inhibiting agent and the types of cancer that may be treated with are described above in more detail. The method may also include administering the chemotherapeutic agent to the subject.

The HDAC1,2 inhibiting agent and chemotherapeutic agent may be administered together to the subject. In some embodiments, the HDAC1,2 inhibiting agent may be administered to the subject before the chemotherapeutic agent is administered to the subject. The HDAC1,2 inhibiting agent may be administered at least about 1 minute, 5 minutes, 10 minutes, 15 minutes, 20 minutes, 25 minutes, 30 minutes, 35 minutes, 40 minutes, 45 minutes, 50 minutes, 55 minutes, 60 minutes, 90 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 1 day, 2 days, 3 days, 4 days, 5 days, 6 days, 7 days, 8 days, 9 days, 10 days, 11 days, 12 days, 13 days, 14 days, 1 week, 2 weeks, 3 weeks, 4 weeks, 5 weeks, 6 weeks, 1 month, 2 months, or 3 months before the chemotherapeutic agent is administered to the subject.

In some embodiments, the method of sensitizing may apply the method for determining if the cancer is sensitive to the HDAC1,2 agent, which is described below in more detail. Accordingly, the method of treating may include detecting a level of BCR-ABL and a level of BBAP in a sample obtained from the subject. The method of treating may also include comparing the detected levels of BCR-ABL and BBAP to levels of BCR-ABL and BBAP in a control sample. If the detected level of BCR-ABL is increased relative to the control level of BCR-ABL, then the cancer may be characterized by BCR-ABL expression. If the detected level of BCR-ABL is not increased relative to the control level of BCR-ABL, then the cancer may not be characterized by BCR-ABL expression. If the detected level of BBAP is increased relative to the control level of BBAP, then the cancer may be characterized by BBAP overexpression. If the detected level of BBAP is not increased relative to the control level of BBAP, then the cancer may not be characterized by BBAP overexpression.

5. Methods for Determining if the Cancer is Sensitive to the HDAC1,2 Agent

Also provided herein are methods for determining if a cancer is sensitive to the HDAC1,2 inhibiting agent. The cancer and HDAC1,2 inhibiting agent are described above in more detail. The methods may include obtaining a sample from the subject suffering from the cancer and measuring a level of one or more markers in the subject. The one or more markers may be BCR-ABL or BBAP or EZH2 mutation. Measuring the level of the one or more markers may include an immunoassay, fluorescence in situ hybridization (FISH), or polymerase chain reaction (PCR).

The method may also include comparing the measured level of the one or more markers to a level of the one or more markers in a control sample. The method may further include determining the cancer is sensitive to the HDAC1,2 inhibiting agent when the measured level of the one or more markers is increased relative to the level of the one or more markers in the control sample.

Accordingly, when the cancer is determined to be sensitive to the HDAC1,2 agent, the method may further include administering the HDAC1,2 agent to the subject.

6. Methods for Monitoring the Efficacy of a Treatment for the Cancer

Also provided herein are methods for monitoring the efficacy of a treatment for the cancer. The treatment may include administering the HDAC1,2 inhibiting agent. The HDAC1,2 inhibiting agent and the cancer are described above in more detail. The method may include obtaining a first sample from the subject before the treatment and a second sample from the subject during or after the treatment. The method may also include measuring a first level of one or more markers in the first sample and a second level of the one or more markers in the second sample. The one or more markers may be 53BP1 or γH2AX. Measuring the first and second levels of the one or more markers may include measuring foci formation of the one or more markers.

The method may further include comparing the first level of the one or more markers and the second level of the one or more markers, and determining that the treatment is effective when the second level of the one or more markers is higher than the first level of the one or more markers.

Accordingly, when the treatment is determined to be effective, the method may include continuing to administer the treatment to the subject, administering the chemotherapeutic agent to the subject, or a combination thereof.

7. Kits

Also provided herein are kits for use with the methods disclosed herein. The kits may include reagents for detecting the one or more markers, which are described above in more detail. The reagents may be any of those reagents known in the art for immunoassays (e.g., ELISA, western blotting, immunoprecipitation (IP), immunohistochemistry, etc.) to detect the one or more markers. The reagents may also be any of those reagents known in the art for detecting nucleic acids, for example, polymerase chain reaction (PCR), reverse transcriptase-PCR (RT-PCR), quantitative RT-PCR (qRT-PCR), and so forth.

The kit may include one or more positive controls and/or one or more negative controls. The kit may further include other material(s), which may be desirable from a user standpoint, such as a buffer(s), a diluent(s), a standard(s), and/or other material useful in sample processing, washing, or conducting any other step of the methods described herein.

The kit according to the present disclosure may include instructions for carrying out the methods of the invention. Instructions included in the kit of the present disclosure may be affixed to packaging material or may be included as a package insert. While instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, and chips), optical media (e.g., CD ROM), and the like. As used herein, the term "instructions" may include the address of an internet site which provides instructions.

The present invention has multiple aspects, illustrated by the following non-limiting examples.

EXAMPLES

Example 1

Materials and Methods

Cell Culture and Chemicals. HeLa cells were cultured in DMEM containing 10% fetal bovine serum (Hyclone, Logan, Utah, USA), 1% penicillin-streptomycin and 1% glutamine. Karpas, SUDHL4 and SUDHL8 cells were cultured in RPMI supplemented with 20% heat inactivated fetal bovine serum (Hyclone, Logan, Utah, USA), 1% penicillin-streptomycin, 1% L-glutamine, 0.002% HEPES, 0.1% amphotericin B. NIH3T3 cells were cultured in DMEM (Cellgro™, Tewksbury, Mass., USA) containing 10% fetal calf serum, 1% penicillin-streptomycin and 1% glutamine. HDAC1,2 and HDAC3 conditional knockout fibrosarcoma cells were cultured and infected with Ad-Cre. DZnep was purchased from Cayman Chemicals, and GSK126 was purchased from Xcess Bio.

Antibodies. The following antibodies were purchased from Abcam: H4, H4K5ac, H4K91ac, BBAP, γH2AX (for western), H4K16ac. H3K23ac, H4K16ac, H2AX and H3K27ac antibodies were purchased form Active Motif. 53BP1 antibody was purchased from Bethyl Laboratories. Anti-H3K27me3 and EZH2 were purchased from Cell Signaling. γH2AX (for immunofluorescence), H3K9K14ac and H3 antibodies were purchased from Millipore.

Laser Micro-irradiation Repair Assay in HeLa Cells. HeLa cells were seeded in 8-well LabTek II chamber dishes. After three hours, the media was removed and replaced with fresh media containing HDAC inhibitors in the described concentrations. After 24 hours of drug treatment, cells were pre-sensitized with 1 μg/ml Hoechst 33342 for ten minutes. Laser micro-irradiation was performed on an inverted confocal microscope (A1 Confocal System, Nikon), using a 405 nm laser focused through a 60× oil objective. Laser output was set to 100%, with twelve regions of interest (ROIs) at a scan speed of 1/16 and pixel dwell of 56.7, which was sufficient to produce detectable damage without noticeable cytotoxicity. Micro-irradiation was performed along parallel lines (ROIs) that spanned each field of view. Cells were allowed to recover for 15 minutes, at which time they were washed once with PBS and fixed for ten minutes in 10% formalin, followed by immunofluorescence staining after permeabilization with 0.5% Triton-X for 4 minutes.

Optimization of Laser Irradiation Repair Assay in Suspension Cells. To perform the laser irradiation protocol in B cells, the utilization of Cell-Tak (Corning Inc.) reagent was optimized to allow cell adherence. One hour before microirradiation, the 8-well LabTek II chamber dish was treated with the Cell-Tak solution for 30 minutes. Cell-Tak, 0.1 M, pH 8.0 sodium bicarbonate, and 1M sodium hydroxide were combined to a volume of 100 μl/cm$^2$ per well (2.5 μl Cell-Tak, 1.25 μl sodium hydroxide and 96.25 μl sodium bicarbonate). After 30 minutes, the solution was removed and the wells were washed with filter-sterilized water. HDAC inhibitor treated cells were then added to wells and allowed to settle for 30 minutes, with Hoechst 33342 being added 20 minutes into this incubation. DLBCL cells used in these experiments were treated with HDAC inhibitor for 24 hours prior in 6-well dishes. Laser output was set to 100%, with twenty-four ROIs, a scan speed of 1/24 and pixel dwell of 86.3. The autofocus ability (Perfect Focus System) of the microscope was also utilized in order to keep the smaller Karpas-422 cells in focus for the laser. A special stage was created to hold the 8-well chamber dishes and to keep the cells in focus. Recovery and fixation were the same as in HeLa cells, but permeabilization during immunofluorescence staining was modified. Permeabilization with either 0.1% Triton-X for 4 minutes or with ice-cold acetone for 10 minutes at −20° C. was used for DLBCL cells.

Histone Extraction by Trichloroacetic Acid. DLBCL cells were treated with ACY957 in 25 cm$^2$ flasks. Following treatment, cells were pelleted, washed with PBS and the pellet was re-suspended in 400 μl of lysis buffer with protease inhibitors (200 μl 0.5M HEPES.KOH, pH 7.9, 15 μl 1M MgCl2, 50 μl 2M KCl, 50 μl 0.1M DTT, 100 μl 0.4M NEM, 10 μl 1000× Aprotinin/Leupeptin, 10 μl 1000× Pepstatin A, and water to a total volume of 10 m L plus Roche protease inhibitor cocktail). To the cell suspension, a final concentration of 0.2M sulfuric acid was added and samples were sonicated twice using the Fisher FB120 sonicator at amplitude of 50% and with 5 pulses. After sonication, proteins were extracted for 30 minutes at 4° C. with end over end rotation. Samples were then centrifuged at 13,000 rpm for 10 minutes at 4° C. and histones were precipitated with a 20% final concentration of trichloroacetic acid and incubated on ice for 30 minutes or moved directly to −80° C. overnight. Following precipitation, samples were centrifuged again for 10 minutes and the resulting pellet was washed with cold acidified acetone (acetone+0.05N HCl). The histone pellets were centrifuged at the same settings but for 5 minutes then washed again with cold acetone. After this wash the pellets were centrifuged for another 5 minutes and the acetone was discarded. Pellets were dried in an incubator at 37° C. for 5 minutes then re-suspended in 50 µl 2×SDS sample buffer+β-mercaptoethanol and 8 µl 1M Tris HCl pH 8 to neutralize. The samples were then boiled for 8 minutes at 95° C. and if there was still visible pellet they were either boiled longer, sonicated, had more sample buffer added or a combination thereof.

Protein Preparation and Western Blot Analysis. Nuclear and chromatin cell extracts were prepared according to methods known in the art, for example, as described in Bhaskara, S. et al. Epigenetics and Chromatin (2013), 6:27, the complete disclosure of which is hereby incorporated by reference for all purposes.

Chromatin Immunoprecipitation Assay. ChIP assays were performed according to methods known in the art, for example, as described in Bhaskara, S. et al. Molecular Cell (2008) 30(1):61-72, the complete disclosure of which is hereby incorporated by reference for all purposes.

RNA-Seq Analysis. Total RNA was isolated from Karpas cells that were treated with DMSO or 2 µM ACY-957 for 24 h using the Versagene RNA isolation kit (5 Prime). The treatments were done in triplicate and sequenced using the Illumina Hiseq2000 sequencer. Illumina TruSeq Stranded sequencing following RiboZero treatment was performed.

Immunofluorescence. Cells were fixed in either 10% formalin or methanol-acetone (1:1) for 10 min at −20*C. The cells were then permeabilized with 0.5% Triton-X-100 in PBS for 5 min at room temperature (RT), blocked in 10% normal goat serum (Sigma) for 30 min and stained with primary antibody for 1 h at RT. Cells were incubated with secondary antibody (anti-mouse or anti-rabbit IgG, Alexa Fluor 488/546) at a 1:600 dilution for 45 min at RT, and counterstained with Hoechst 33342 (Sigma) at 1:1000 dilution to visualize the nuclei. Images were captured using Zeiss Axioskop mot plus microscope with a 40× lens and analyzed using the AxioVision software.

Propidium-iodide Cell Cycle Analysis. Propidium-iodide cell cycle analysis was performed according to methods known in the art, for example, as described in Bhaskara, S. et al. Molecular Cell (2008) 30(1):61-72, the complete disclosure of which is hereby incorporated by reference for all purposes.

Example 2

H3K27Me3 is Increased in DLBCL Cells Expressing Gain-of-Function Mutation of EZH2 Compared to Other Cancer Cells The Karpas-422 line was established from the pleural effusion of a patient with chemotherapy-resistant non-Hodgkin's lymphoma (NHL) and the SUDHL4 line was derived from the peritoneal effusion of a 38-year male NHL patient. Karpas-422 and SUDHL4 lines expressed mutant EZH2 with an amino acid substitution in the catalytic SET domain: the Karpas-422 line contained the Y641N mutation and the SUDHL4 line expressed the Y641S mutation. These changes in EZH2 were gain-of-function mutations resulting in a hyperactive enzyme. Whether EZH2 catalyzed H3K27 trimethylation (H3K27me3) is augmented in Karpas-422 and SUDHL4 lines compared to other cancer cell lines was examined. Extracts were prepared for western analysis from Karpas-422, SUDHL4, NALM6 (a pre B-acute lymphoblastic leukemia line), HeLa (a cervical adenocarcinoma line) and Rosa26 (a mouse fibrosarcoma line). Protein levels of EZH2 in Karpas-422 and SUDHL4 lines were similar to that present in other cancer cell lines (FIG. 1). However, increased H3K27me3 levels were observed in the Karpas-422 and SUDHL4 lines compared to NALM6, HeLa and mouse fibrosarcoma lines (FIG. 1). Therefore, the Y641N or Y641S mutations in the EZH2 SET domain did not affect EZH2 protein levels, but resulted in a hyperactive enzyme causing aberrantly increased H3K27me3 in the EZH2$^{GOF}$ DLBCL cells compared to other cancer cell lines.

Example 3

ACY-957 is a Selective Small Molecule Inhibitor of HDAC1 and HDAC2 Enzymatic Activities H3K27me3 is linked to transcriptional repression and it is enriched at the transcription start sites of inactive genes. H3K27me3 contributes to the proliferation and chemoresistance in a subset of DLBCL cells. In addition to methylation, the H3K27 residue also undergoes acetylation, which is dynamically regulated by the action of histone acetyltransferases (HATs) and deacetylases (HDACs). HDAC1,2 interacts with the EZH2-containing PRC2 complex and may function to remove the acetyl group from the lysine residue in order for EZH2 catalyzed methylation to occur. Therefore, inhibition of HDAC1,2 activities alone or in combination with inhibition of EZH2 activity could be a strategy to overcome lymphomagenesis in DLBCL cells by blocking the gain-of-function mutant EZH2 mediated H3K27 hypertrimethylation via increased histone acetylation.

To test this possibility, we chose to inhibit HDAC1,2 activities in DLBCL cells using a novel small molecule, ACY-957. Among class I HDACs, Hdac1,2 share a 50% sequence homology with Hdac3. Therefore, we first determined the selectivity of ACY-957 towards HDAC1 and HDAC2 in in vitro enzyme assays using recombinant enzymes. We also included ACY-1044, a selective small molecule inhibitor of HDAC3, as a control in our characterization studies. The biochemical IC$_{50}$ values obtained using in vitro HDAC assays showed that a 7.4-fold and 3.3-fold higher concentration of ACY-1044 (the HDAC3-selective inhibitor) was required to inhibit HDAC1 and HDAC2, respectively, when compared to HDAC3 (FIG. 2A). In contrast, ACY-957 was 185-fold selective for HDAC1 and 72-fold more selective for HDAC2 when compared to HDAC3 (FIG. 2A).

Figure 12:
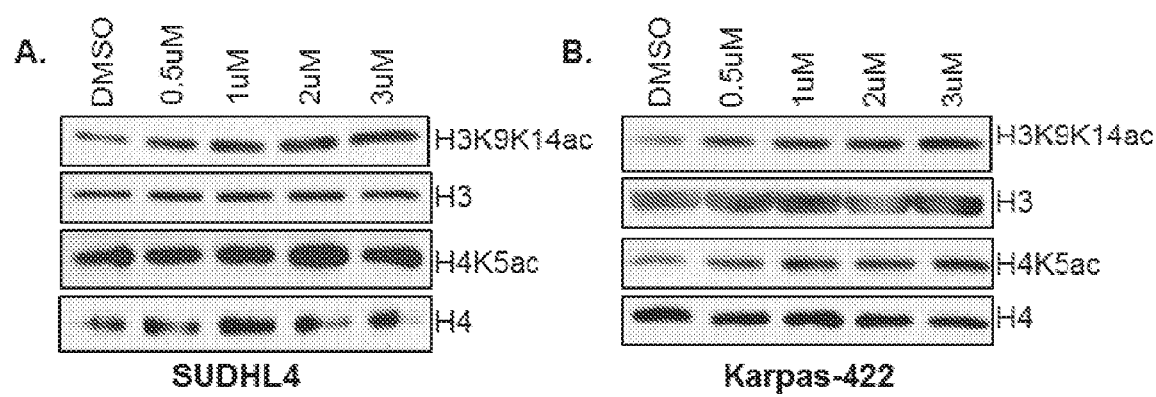
FIG. 12 shows SUDHL4 (A) and Karpas-422 (B) cells were treated with increasing concentrations of ACY1044 and whole cell lysates were prepared following a 24 hr treatment. Western blot analysis of H3K9K14ac and H4K5ac was performed. Histone H3 and H4 were used as controls.

Next, we tested the ability of these small molecules to inhibit HDAC1,2 or HDAC3 activities in vivo in EZH2 gain-of-function mutant (EZH2GOF) DLBCL cell lines. We treated Karpas-422 and SUDHL4 cells with increasing amounts of ACY-957 for 24 hr and examined changes in histone acetylation marks; specifically, acetylation at histone H3 K9 and K14 residues (H3K9,K14ac) and at histone H4 K5 residue (H4K5ac), which are increased in Hdacs1,2$^{-/-}$ cells. Western analysis showed a concentration-dependent increase in the levels of H3K9,K14ac and H4K5ac in ACY-957 treated Karpas-422 and SUDHL4 cells compared to the DMSO (vehicle) treated control cells (FIGS. 2B and 2C). H3K9, K14ac and H4K5ac levels were also increased in Hdac3$^{-/-}$ cells and treatment of Karpas-422 and SUDHL4 cells with increasing concentrations of ACY-1044 (the HDAC3 inhibitor) also resulted in elevated H3K9,K14ac and H4K5ac levels compared to the DMSO treated control cells (FIG. 12). However, the increase in H3K9,K14ac and H4K5ac levels appeared to be more robust following inhibition of HDAC1,2 activities using ACY-957 than inhibition of HDAC3 activity using ACY-1044 (FIGS. 2B, 2C and 12). Collectively, these results determined the minimum concentration of ACY-957 and ACY-1044 required to inhibit HDAC1,2 or HDAC3 activities in vivo in DLBCL cells.

Next we set out to examine the ability of ACY-957 to inhibit only HDAC1,2 activities in DLBCL cells. We performed a screen in Hdac1,2 or Hdac3 knockout cells using Western blotting to identify a histone acetylation mark that is targeted by HDAC1,2 and not HDAC3. Western analysis of histone acetylation marks altered in Hdacs1,2$^{-/-}$ or Hdac3$^{-/-}$ fibrosarcoma cells revealed that global H3K23ac levels were increased only upon loss of HDAC1,2 and not in cells lacking HDAC3 (FIG. 2D). Therefore, this result identified H3K23ac as a substrate that was specifically targeted by HDAC1,2 and not HDAC3. Hence, we used changes in H3K23ac as a readout to test the ability of ACY957 to specifically inhibit HDAC1,2 activities in DLBCL cells. We treated the refractory DLBCL cells, Karpas-422 and SUDHL4, with 2 µM ACY-957, 2 µM ACY-1044 (the HDAC3 inhibitor) or 2 µM Vorinostat (SAHA) (a pan HDAC inhibitor that targets HDAC1,2 and HDAC3). Western analysis showed that ACY-957 treatment of DLBCL cells increased H3K23ac levels (FIG. 2E). Moreover, the increase in H3K23ac obtained using ACY-957 treatment was similar to that obtained following treatment with SAHA (FIG. 2E), indicating that Hdac1,2 were the primary class I HDACs involved in deacetylating H3K23ac. Addition of ACY-957, but not ACY-1044, to Karpas-422 or SUDHL4 cells resulted in an increase in H3K23ac levels compared to the DMSO treated control cells (FIG. 2F). Taken together, these results demonstrated that ACY-957 specifically inhibited HDAC1,2 activities in DLBCL cells.

Example 4

Selective Inhibition of HDAC1,2 Activities Caused Cytotoxic or Cytostatic Effects in EZH2$^{GOF}$ DLBCL Cells Having established that ACY-957 was a selective inhibitor of HDAC1,2, we next asked whether HDAC1,2 activity was required for the proliferation and/or survival of the EZH2$^{GOF}$ DLBCL cells. Since these DLBCL cells expressed a hyperactive form of EZH2, pharmacological inhibition of EZH2 activity was considered a therapeutic strategy. Therefore, we treated Karpas-422 and SUDHL4 cells with ACY-957 for 24 h, 48 h and 72 h, and performed cell cycle analysis to measure the extent of cell death (cytotoxic) and/or cell cycle arrest (cytostatic) triggered as a result of inhibiting HDAC1,2 activity in these cells. For comparison, we also treated Karpas-422 and SUDHL4 cells with another EZH2 inhibitor (DZNep or GSK126), either alone or in combination with ACY957, for the indicated time prior to cell cycle analysis. GSK126 was a S-adenosyl-methionine-competitive inhibitor of EZH2 methyltransferase activity, and DZNep was a S-adenosylhomocysteine hydrolase inhibitor that disrupted the components of the PRC2 complex, thereby causing reduced chromatin-associated EZH2 levels.

Figure 3:
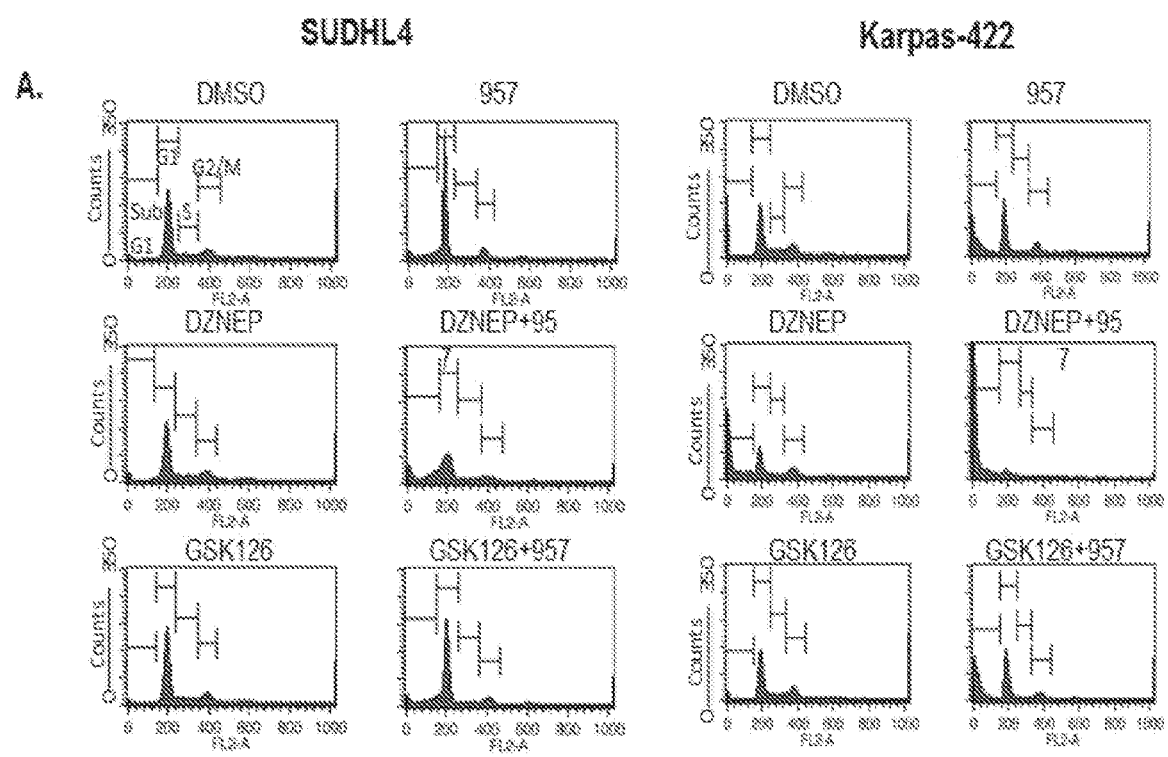
FIG. 3 shows that HDAC1,2 inhibition caused apoptosis in Karpas-422 cells and a G1 arrest in SUDHL4 cells: (A): SUDHL4 and Karpas-422 were treated with DMSO, 2 μM ACY-957, 0.5 μM DZNEP, 0.5 μM GSK126 or a combination of drugs for 72 h prior to cell cycle analysis by propidium-iodide staining. Representative plots from one experiment out of three independent experiments are shown in the figure. (B): Quantitation of the cell cycle data in (A), compiled from three independent analyses. The graphs plotted the average percentage of cells in each phase of the cell cycle. Error bars indicated the standard error calculated from three independent experiments. *p=0.005; **p=0.0176. (C): FACS analysis following BrdU-PI staining of Karpas-422 and SUDHL4 cells was performed following a 48 h or 72 h treatment with ACY-957. Representative plots from two independent experiments are shown in the figure. Quantitation of S-phase cells at 48 h and 72 h post ACY-957 treatment is also shown in the figure. *p=0.01, p=0.03, *p=0.03 and ****p=0.02.

Compared to treatment with ACY-957 for 24 h or 48 h, treatment of Karpas-422 cells with ACY957 for 72 h resulted in a larger increase in the number of sub-G1/dead cells, and treatment of SUDHL4 cells with ACY957 for 72 h resulted in a greater number of cells arrested in G1 phase and those present in the sub-G1 population (FIGS. 3A and 3B). Treatment with DZNep alone triggered a modest increase in dead/sub-G1 SUDHL4 cells, but resulted in a larger increase in the number of dead Karpas-422 cells similar to that obtained with ACY957 treatment (FIG. 3).

Combined addition of both DZNep and ACY-957 caused an enhanced cytotoxic effect with a significant increase in the number of sub-G1 or dead Karpas-422 cells, which was greater than that obtained when these cells were treated with either DZNep alone or ACY-957 alone (FIG. 3B). Combined addition of DZNep and ACY-957 to SUDHL4 cells also elicited a similar enhanced cytotoxic effect, albeit more modest, with an increase in the number dead or sub-G1 cells that was slightly larger than that obtained with ACY-957 or DZNep alone (FIG. 3B).

Addition of GSK126 alone did not result in any defect in the cell cycle progression and/or survival of Karpas-422 and SUDHL4 cells even after an incubation period of 72 h (FIG. 3). Since, we observed a significant cell death with ACY-957 by 72 hr, we could not test the synergistic effect of ACY-957 and GSK-126 following a 6-day treatment.

Figure 13:
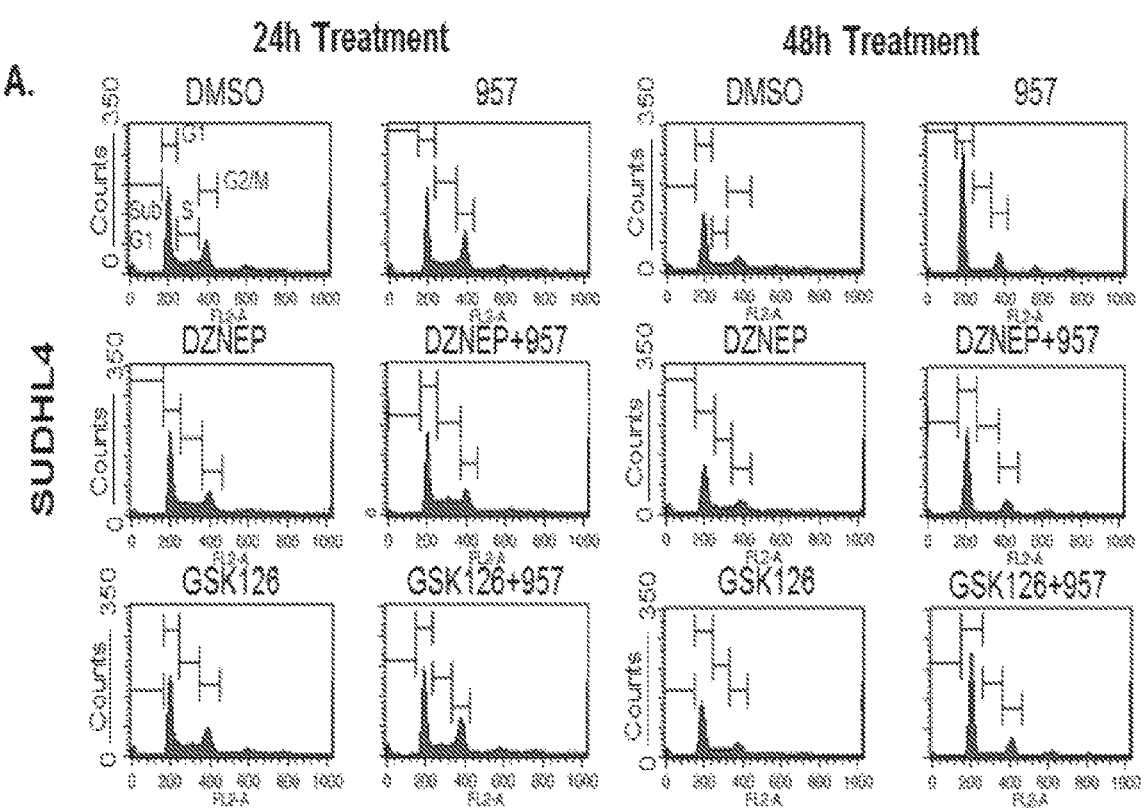
FIG. 13 shows in (A): SUDHL4 and Karpas-422 were treated with DMSO, 2 μM ACY-957, 0.5 μM DZNEP, 0.5 μM GSK or a combination of drugs for 24 or 48 hr and cell cycle analysis of propidium-iodide stained cells was performed. Representative plots are shown in the figure. (B): Quantitation of the cell cycle analysis performed in (A). Data from three independent cell cycle analyses were compiled and average percentage cells with standard errors were shown in this panel.

Treatment of Karpas-422 and SUDHL4 cells for 24 h with the HDAC1,2 selective inhibitor (ACY957) alone or the EZH2 inhibitor alone (DZNep or GSK126) or their combined addition (DZNep+ACY957 or GSK126+ACY957) did not affect their progression through the cell cycle, as the profiles for the inhibitor-treated cells looked similar to that obtained for the DMSO-treated control cells (FIG. 13). Following 48 h incubation, ACY-957 treatment resulted in the accumulation of SUDHL4 cells in G1 phase (G1 arrest) (FIG. 13A) and a modest accumulation of sub-G1 population (indicative of dead cells) was observed in ACY-957-treated Karpas-422 cells when compared to the control DMSO-treated cells (FIG. 13B). Inhibition of EZH2 activity using GSK126 alone did not cause any change in the progression of Karpas-422 or SUDHL4 cells through the cell cycle (FIG. 13).

These results indicated that selective inhibition of HDAC1,2 activities caused a more rapid adverse effect on the proliferation and survival of the chemo resistant DLBCL cells than the selective inhibition of EZH2 activity. Treatment with the EZH2 inhibitor DZNep for 48 h caused a modest increase in the number of dead Karpas-422 cells similar to that observed with the ACY957 treatment (FIG. 13B). However, DZNep when combined with ACY957 resulted in a significant/substantial increase in the number of Sub-G1 or dead Karpas-422 cells (FIG. 13). No such synergistic effect was observed when ACY957 was combined with GSK126. These findings together indicated that inhibition of HDAC1,2 activities along with the dissociation of the PRC2 complex using DZNep, but not inhibition of EZH2 activity using GSK126, caused a synergistic cytotoxic effect on Karpas-422 cells. FACS analysis following bromodeoxyuridine (BrdU)-propidium iodide labeling and staining was performed at 48 h and 72 h following treatment of cells with ACY-957. A decrease in S-phase population accompanied by either increased cell death or a G1 arrest was observed in Karpas-422 and SUDHL4 cells, respectively (FIG. 3C). Collectively, results from our analysis of the chemoresistant DLBCL cells showed that HDAC1,2 activity and an intact PRC2 complex are required for progression through the cell cycle and/or survival.

Collectively, results from this analysis of the chemoresistant DLBCL cells following selective inhibition of HDAC1,2 and/or EZH2 activities showed that HDAC1,2 activities and an intact PRC2 complex were required for progression through the cell cycle and/or survival.

Example 5

H3K27Ac was Increased in the EZH2 Gain-of-Function Mutant DLBCL Cells Upon Selective Inhibition of HDAC1,2 Activities The histone H3K27 residue was subjected to reversible acetylation and methylation. The aberrantly increased H3K27me3 resulting from a hyperactive EZH2 in DLBCL cells may contribute to both lymphomagenesis and chemoresistance. Hence, we next asked whether the cytotoxic or cytostatic effects of ACY-957 or DZNep on the chemoresistant DLBCL cells correlated with any change in the dynamics of acetylation and methylation at the H3K27 residue on chromatin. Therefore, we treated the refractory DLBCL cells, Karpas-422 and SUDHL4, with DMSO (vehicle), the HDAC1,2 selective inhibitor alone (ACY-957), the EZH2 inhibitor alone (DZNep) or a combination of both these inhibitors (ACY-957+DZNep). We also treated cells with the second EZH2 inhibitor, GSK126 alone, or combined with ACY-957 (ACY-957+GSK126). As an additional control, cells were treated with ACY-1044 (the HDAC3 selective inhibitor) alone or combined with one of the two EZH2 inhibitors (ACY-1044+DZNep or ACY-1044+GSK126). Cells were treated for 48 h prior to preparing chromatin extracts for Western analysis using antibodies recognizing H3K27ac or H3K27me3.

Figure 4:
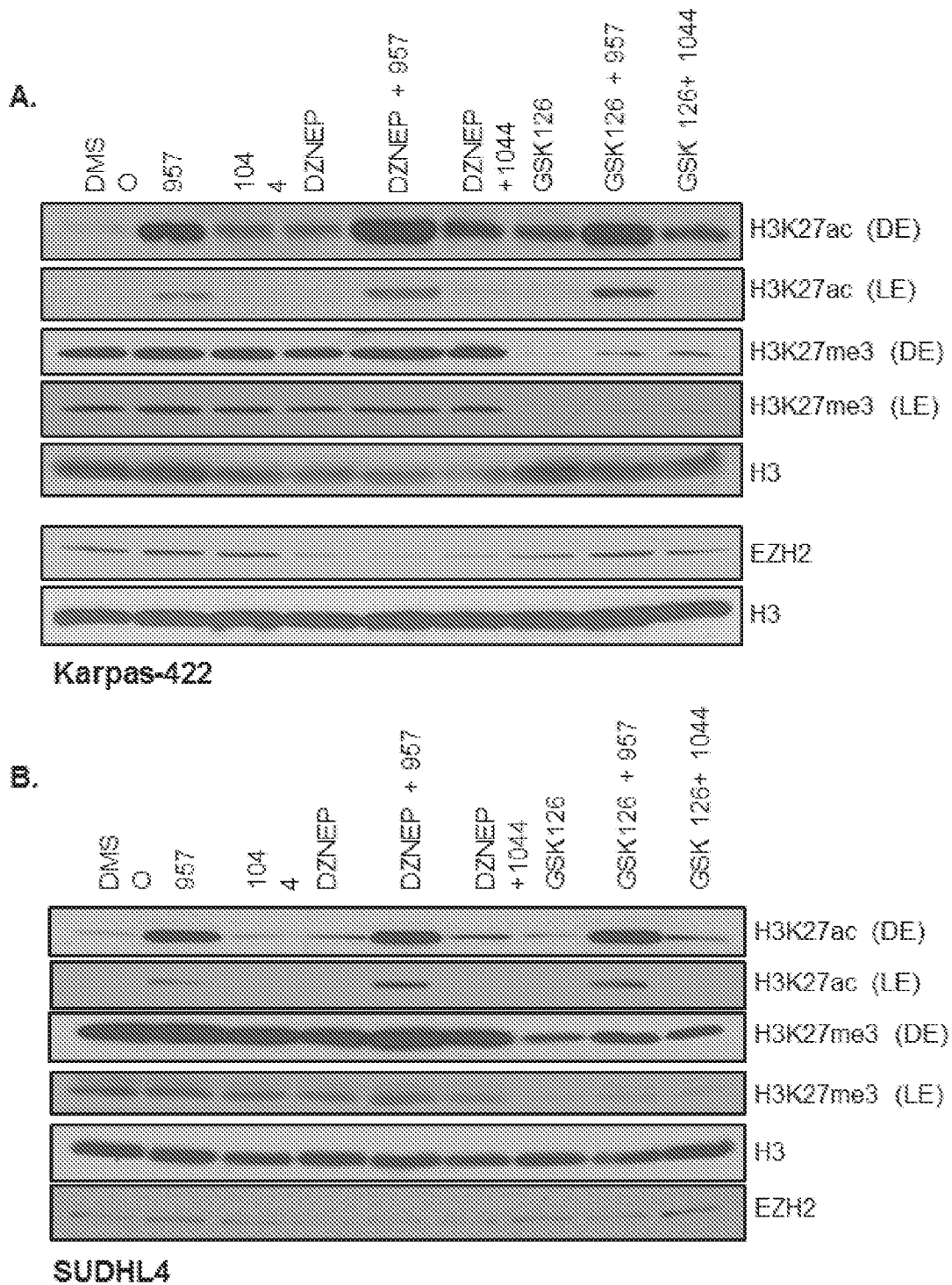
FIG. 4 shows that selective HDAC1,2 inhibition increased global chromatin-associated H3K27ac without altering H3K27me3 in EZH2 gain-of-function mutant DLBCL cells: Karpas-422 (A) and SUDHL4 (B) were treated with DMSO, 2 μM ACY957, 2 μM ACY1044, 0.5 μM DZNEP, 0.5 μM GSK126 or combinations of these drugs for 48 hr prior to chromatin extraction. Western blot analysis was done with anti-H3K27ac, H3K27me3 or EZH2 and histone H3 served as a loading control.

As shown in FIG. 4, selective inhibition of HDAC1,2 activity alone using ACY-957 or when combined with EZH2 inhibitors led to a robust increase in global H3K27ac levels in both Karpas-422 and SUDHL4 cells. Global H3K27me3 levels were not reduced and remained unchanged in ACY957 treated cells compared to the DMSO treated control cells (FIG. 4). While treatment with GSK126 led to a decrease in global H3K27me3 levels, a greater reduction in H3K27me3 levels due to combined action of GSK126 and ACY-957 was not observed (FIG. 4). In fact, a slight increase in H3K27me3 levels was observed when cells were treated with both GSK126 and ACY-957 (FIG. 4). These results indicated that addition of acetyl groups onto unmodified H3K27 residues occurred on chromatin without requiring the removal of existing H3K27me3. GSK126 treatment caused a significant reduction in global H3K27me3 (FIG. 4), but it did not trigger death in the chemoresistant DLBCL by 72 h, except in the case of combination with ACY-957 in Karpas-422 cells (FIG. 3). In contrast, inhibition of HDAC1,2 activity using ACY-957 and/or reducing chromatin-bound EZH2 using DZNep compromised the viability of the chemoresistant DLBCL without reducing global H3K27me3 levels (FIGS. 3 and 4). These results together indicated that the viability and/or cell cycle progression of the refractory DLBCL cells was dependent on HDAC1,2 activity and an intact EZH2 containing PRC2 complex but not on global H3K27me3

Example 6

Selective Inhibition of HDAC1,2 Induced the Expression of DNA Damage Response Genes in EZH2-Mutant DLBCL Cells While selective inhibition of HDAC1,2 activity did not reduce global H3K27me3 in the EZH2 gain-of-function DLBCL cells (FIG. 4), the cell cycle arrest and/or death triggered in these cells by HDAC1,2 inhibition may be due to increased H3K27ac with a concomitant decrease in H3K27me3 locally at select target loci, such as, genes involved in cell cycle regulation, DNA repair or DNA damage signaling and apoptosis, which could also be the targets of EZH2. To test this possibility, we examined changes in gene expression in the EZH2 gain-of-function DLBCL line, Karpas-422, following inhibition of HDAC1,2 activity using ACY-957. Three independent DMSO or ACY-957 treatments of Karpas-422 cells for 24 h were performed for total RNA isolation, which was then subjected to RNA-seq involving next-generation sequencing and bioinformatics analysis. Our RNA-seq analysis showed that expression of 492 genes was up regulated following inhibition of HDAC1,2 activity in Karpas-422 cells compared to the DMSO control (FIG. 5A).

In order to determine whether genes up regulated following inhibition of HDAC1,2 activity were also targets of EZH2, we compared our gene set with GSK-126 treated Karpas-422 RNA-seq dataset, in which target genes of EZH2 were identified by determining changes in the expression following treatment of Karpas-422 cells with GSK-126. This comparison yielded a list of 71 genes that were commonly up regulated in both the datasets (FIG. 5A). A similar comparison yielded 6 targets that were common in the list of genes down regulated following inhibition of HDAC1,2 activity or upon inhibition of EZH2 (FIG. 5A). Classification of the common set of 71 genes that were up regulated in ACY-957 treated samples and the known EZH2 target genes based on their cellular functions revealed that they belonged to pathways, such as, signaling and are not related to apoptosis, DNA repair, DNA damage response and cell cycle regulation (FIG. 5B). Inhibition of EZH2 activity is proposed to inhibit tumor growth in non-Hodgkin's lymphoma via inducing the expression of BLIMP1 (a tumor suppressor). However, DESeq analysis of our RNA-seq data showed that BLIMP1 expression was modestly up regulated following selective inhibition of HDAC1,2 (1.7-fold). GSK-126 treatment of Karpas-422 cells led to a 2.4-fold increase in Karpas-422 cells. However, we saw robust cell death with ACY-957 when compared to GSK-126 even when a high concentration of 2 µM GSK-126 was used on these cells. Hence, up regulation of BLIMP1 alone was unlikely to be the major cause of cell death in the chemoresistant Karpas-422 cells upon ACY-957 treatment. Taken together, these findings indicated that inhibition of HDAC1,2 activity impinged on the viability and cell cycle progression of refractory DLBCL cells by affecting processes other than EZH2 regulated gene expression.

When cells sense endogenous DNA damage, BMF (BCL2-modifying factor, a pro-apoptotic gene) promotes apoptosis by binding to the anti-apoptotic BCL2 protein. SAHA, a pan-HDAC inhibitor, was shown to induce tumor cell selective expression of the BMF gene. We found that BMF expression was increased by 2.5-fold upon selective inhibition of HDAC1,2 activity (FIG. 5C).

Figure 5:
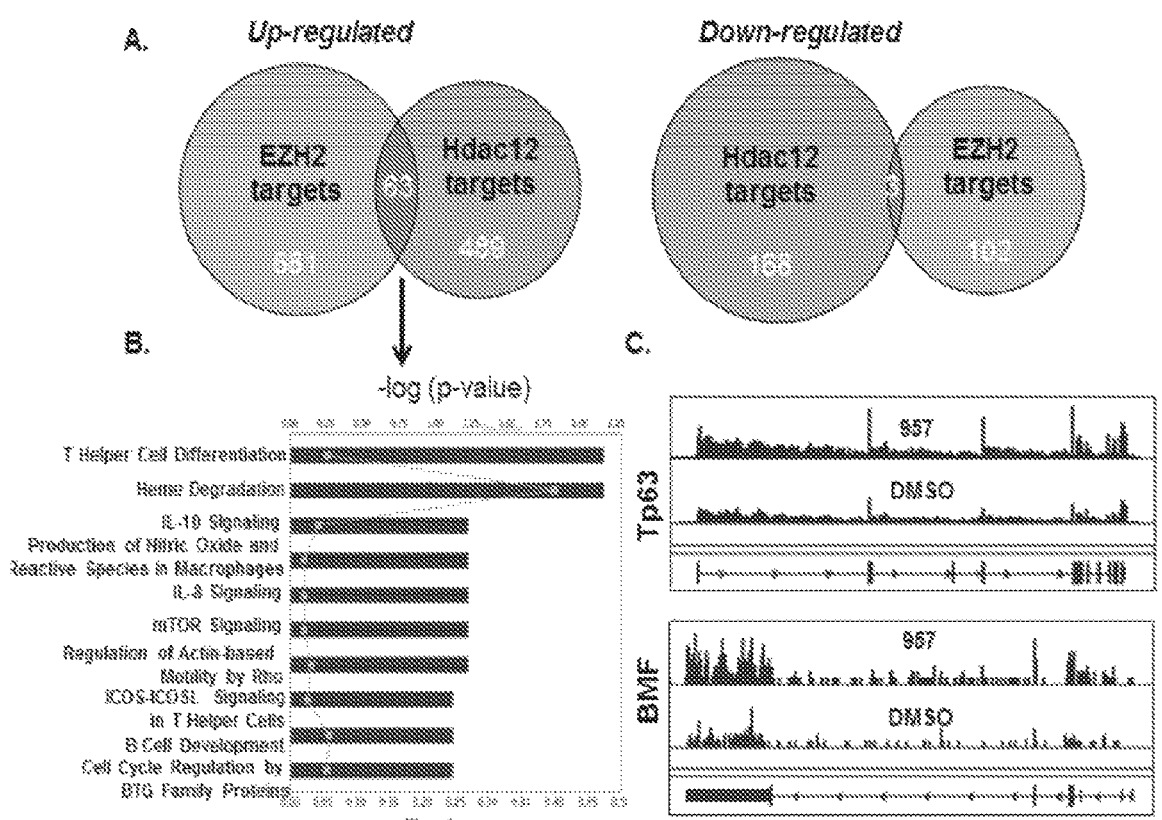
FIG. 5 shows that inhibition of HDAC1,2 activity increased the expression of DNA damage response genes and H3K27ac at these promoters: (A): Total RNA was isolated from Karpas-422 cells following a 24 h treatment with 2 μM ACY-957 for 24 h. RNA samples obtained from three independent treatments were subjected to RiboZero stranded sequencing using the Illumina Hiseq2000 sequencer. RNA-seq data from ACY-957-treated samples was compared to the publically available RNA seq data set from Karpas-422 cells following GSK126 treatment of Karpas-422 cells. Venn diagrams were made using the R package VennDiagram. Genes with adjusted p-value<0.05 and absolute log 2 fold change>0.585 were used in this analysis. (B): Pathway analysis of the 71 commonly up regulated genes was performed. Screen shots of the pathways that were misregulated in both ACY-957-treated Karpas-422 cells and in Karpas-422 cells following GSK-126 treatment. Only genes that showed a greater than 1.5-fold change were used in this analysis. The bars are the significance (−log (pvalue)), the line is the ratio given by number of significant genes in a pathway over number of genes in the pathway. (C): Base read depth, scaled per million mapped reads, for BMF and Tp63 genes in DMSO- or ACY-957-treated Karpas-422 cells. Screenshots taken from IGV are shown in the figure. (D): ChIP analysis of H3K27ac, H3K27me3 and H3 at the promoters of BMF and Tp63 genes was performed following treatment of Karpas-422 cells with either DMSO or 2 μM ACY-957. Three independent ChIP experiments with H3K27me3, H3K27ac and H3 antibodies were done and the PCR was performed in triplicate. Histone H3 occupancy at a given target locus was used as a control to account for total histone levels. Rabbit IgG was also as a negative control to determine background signal. The threshold cycles from qRT-PCR ($C_T$ values) obtained for the rabbit IgG control were between 31-33 cycles, and the signal obtained from using the H3K27ac or H3K27me3 antibodies ranged between 22-28. Hence, we obtained 8- to 512-fold enrichment with the H3K27me3 or the H3K27ac antibody in our ChIP assays when compared to the rabbit IgG negative control. To calculate fold change in the levels of H3K27 modification at a given target locus, we normalized the $C_T$ value obtained from H3K27me3 or H3K27ac ChIP to the $C_T$ value obtained from histone H3 ChIP. Fold-increase as determined by real-time PCR analysis in H3K27ac relative to total H3 occupancy was calculated for both ACY-957-treated and DMSO-treated samples and the relative fold-enrichment of H3K27ac and H4K27me3 in ACY-957-treated samples was calculated following normalization to DMSO-treated samples. The data represented an average fold-change calculated from three independent experiments+/−standard error. *p=0.003 and **p=0.004 (E): ChIP analysis of HDAC1 and HDAC2 at the promoters of BMF and Tp63 genes was performed in Karpas-422 cells. Fold-increase as determined by real-time PCR analysis in HDAC1/HDAC2 relative to rabbit IgG occupancy was calculated from two independent experiments. The ChIP signal obtained from the antibodies recognizing HDAC1 or HDAC2 antibodies was normalized to the $C_T$ values obtained from the input DNA. We then calculated fold enrichment in HDAC1 and HDAC2 ChIP signals relative to the negative rabbit IgG control. This fold-change is depicted in panel E. Statistical analysis of the ChIP data was performed and p-values were calculated. *p=0.07, p=0.0002, *p=0.06 and ****p=0.003.

Additional searches for genes related to the DNA damage response and up regulated following inhibition of HDAC1,2 activity revealed a 2-fold increase in the expression of TP63 (tumor protein 63), a p53 family member (FIG. 5C). TP63 was required for p53-dependent apoptosis in mouse embryo fibroblasts (MEFs) following endogenous DNA damage.

To gain insight into the mechanism of transcriptional activation at the TP63 and BMF genes following inhibition of HDAC1,2 activity, we examined whether changes, if any, occur in the levels of H3K27ac (an activating mark) and H3K27me3 (a repressive mark) at the regulatory promoter regions of these genes using chromatin immunoprecipitation (ChIP) assay. Real-time PCR analysis of ChIP DNA showed an increase in H3K27ac levels at the promoter regions of both TP63 and BMF genes following ACY-957 treatment (FIG. 5D). However, a concomitant decrease in H3K27me3 was not observed at the TP63 and BMF promoters (FIG. 5D). To determine whether HDAC1 and HDAC2 play a direct role at these genes and regulate H3K27ac at their promoter regions, we performed ChIP analysis with HDAC1 and HDAC2 antibodies. We found a significant enrichment in HDAC1 and HDAC2 occupancies at the BMF and Tp63 promoters (FIG. 5E). These results indicated that HDAC1,2 inhibition triggers death and cell cycle defects in the refractory DLBCL cells without requiring a reduction in the repressive H3K27me3 at the target genes. Overall, data from our gene expression analyses indicated that the death and/or cell cycle arrest in chemoresistant/refractory DLBCL cells triggered by selective inhibition of HDAC1,2 activity was from the activation of DNA damage response resulting from endogenous DNA breaks.

Example 7

Selective Inhibition of HDAC1,2 Activity Increased DNA Damage and Impaired DNA Repair in the EZH2 Gain-of-Function Mutant DLBCL Cells Next, we tested whether selective inhibition of HDAC1,2 activity in EZH2 gain-of-function mutant DLBCL cells caused endogenous DNA breaks. Serine 139 of H2AX is phosphorylated ($\gamma$H2AX) in response to DNA breaks and it accumulated on chromatin over many megabases around a break site to form the nuclear foci. $\gamma$H2AX foci formation was a marker of DNA damage and was used to measure the production of DNA damage and the subsequent repair of the DNA lesion.

We measured $\gamma$H2AX foci formation using immunofluorescence in EZH2 gain-of-function mutant DLBCL cells, SUDHL4 and Karpas-422, following a 24 h or 48 h treatment with DMSO or ACY-957 or DZNep and GSK126, the EZH2 inhibitors, were also included in this analysis for comparison. Following a 24 h treatment, no significant increase in DNA damage was observed in EZH2 gain-of-function mutant DLBCL cells treated with the HDAC1,2 selective inhibitor or the EZH2 inhibitors (data not shown), which agreed with the lack of any defects in the cell cycle progression observed at this time point using these inhibitors (FIG. 3). A significant increase in the number of cells with greater than six $\gamma$H2AX foci was observed upon ACY-957 or DZNep treatment of SUDHL4 and Karpas-422 cells for 48 h (FIG. 6A). GSK126 treatment caused a slight increase in $\gamma$H2AX foci at this time point (FIG. 6A). We confirmed our results from immunofluorescence by examining changes in $\gamma$H2AX levels on chromatin using Western analysis following treatment of SUDHL4 and Karpas-422 cells with ACY-957 or either of the EZH2 inhibitors. Similar to that observed using immunofluorescence, selective inhibition of HDAC1,2 activity with ACY-957 led to an increase in chromatin associated $\gamma$H2AX compared to the control DMSO treatment in both SUDHL4 and Karpas-422 cells (FIG. 6B). Between the two EZH2 inhibitors, DZNep treatment caused a greater increase in $\gamma$H2AX levels on chromatin compared to GSK126 (FIG. 6B), consistent with the observations using immunofluorescence (FIG. 6A). These results indicated that both HDAC1,2 and EZH2 activity were required to prevent the accumulation of endogenous DNA damage.

Increase in $\gamma$H2AX and persistent endogenous DNA damage may occur as a consequence of impaired DNA repair. Therefore, to measure the efficiency of DNA repair, we examined $\gamma$H2AX levels on chromatin after a recovery period when DNA repair occurred following exposure to an exogenous DNA damaging agent. The EZH2 gain-of-function mutant DLBCL cells, SUDHL4 and Karpas-422, were treated with DMSO or ACY-957 for 48 h prior to exposure to ionizing radiation (IR). Chromatin extracts were prepared from these cells following a 30 min recovery after exposure to IR and analyzed by Western blotting. Increased $\gamma$H2AX levels on chromatin were observed for ACY-957 treated cells compared to the control DMSO-treated cells following a 30 min recovery time period after exposure to IR (FIG. 6C). $\gamma$H2AX levels on chromatin in the ACY-957-treated cells post-recovery from IR were more than those present on chromatin in the control DMSO-treated cells post-recovery from IR and in the control cells treated with either DMSO or ACY-957 without any exposure to IR (FIG. 6C). These results indicated that HDAC1,2 activities were required for efficient DNA repair and that inhibition resulted in the persistence of DNA breaks. Collectively, these results indicated that selective inhibition of HDAC1,2 in the EZH2 gain-of-function mutant DLBCL impaired DNA repair and activated the DNA damage response.

Example 8

Figure 6:
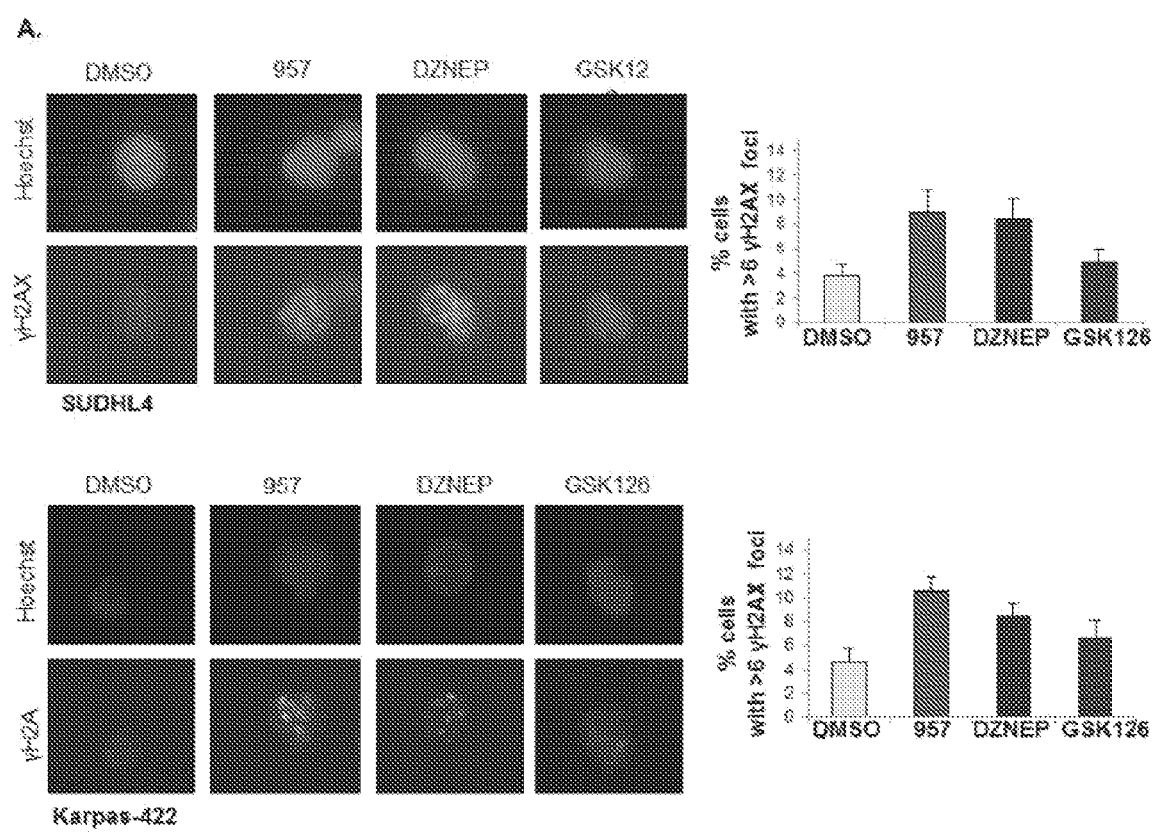
FIG. 6 shows that selective inhibition of HDAC1,2 activated DNA damage response and impaired DSB repair in EZH2 gain-of-function mutant DLBCL cells: (A): SUDHL4 and Karpas-422 cells were treated with DMSO, 2 μM ACY-957, 0.5 μM DZNEP or 0.5 μM GSK126 for 48 hr and immunofluorescence staining with γH2AX was performed. The percentage of cells with 6 or greater γH2AX foci were counted in three independent experiments and at least 100 cells were counted in each experiment. The average with standard errors calculated from three independent experiments is shown in the figure. (B): SUDHL4 and Karpas-422 cells were treated with DMSO, 2 μM ACY-957, 0.5 μM DZNEP or 0.5 μM GSK126 for 48 hr. Histones were purified using trichloroacetic acid extraction protocol (see Example 1). Western blot analysis was done with anti-γH2AX and histone H2AX served as the loading control. (C): SUDHL4 and Karpas-422 cells were treated with DMSO or 2 μM ACY-957 for 48 hr. Following DMSO or ACY957 treatment, cells were exposed to a 5Gy dose of ionizing radiation and allowed to recover for 30 minutes prior to chromatin extraction. Western blot analysis was done with anti-γH2AX where total histone H2AX served as a loading control. (D): Karpas-422 cells were micro-irradiated with laser and allowed to recover for 15 minutes before fixation and immunofluorescence staining with anti-γH2AX, anti-HDAC1 and anti-HDAC2 antibodies was done.

HDAC1,2 Activity were Required for the Enrichment of H3K27Me3 at Break Sites During DNA Repair in EZH2 Gain-of-Function Mutant DLBCL Cells We next set out to gain insights into mechanism by which selective inhibition of HDAC1,2 activity impaired DNA repair in the chemoresistant DLBCL cells expressing the gain-of-function EZH2 mutation. As shown in FIG. 6, both HDAC1,2 and EZH2 activities were required for the repair of DNA breaks. EZH2 and H3K27me3 also localized to the sites of DNA damage and may play a role in the repair of double strand DNA breaks. HDAC1 and HDAC2 localize to DNA break sites in Karpas-422 cells (FIG. 6D). Therefore, we asked whether inhibiting HDAC1,2 activity impaired DNA repair in the refractory DLBCL cells by altering the acetylation-methylation dynamic at the H3K27 residue on chromatin.

We first examined whether inhibiting HDAC1,2 activity induced any change in global H3K27ac or H3K27me3 on chromatin following DNA damage and during DNA repair. SUDHL4 or Karpas-422 cells with or without exposure to ionizing radiation (IR) were initially treated with DMSO or ACY-957 for 48 hr. Chromatin extracts were prepared from these cells following a 30 min recovery period (the repair phase) and changes in histone modifications were examined by Western blotting. Global H3K27ac levels on chromatin were increased in ACY957 treated DLBCL cells compared to the control DMSO treated cells with or without exposure to IR (FIG. 7A). However, a concomitant decrease in global H3K27me3 levels on chromatin was not observed following the 30 min recovery period from IR in the ACY957 treated cells compared to the DMSO treatment (FIG. 7A). These results indicated that HDAC1,2 actively removed H3K27ac on chromatin during DNA repair without affecting global H3K27me3 levels.

Active recruitment of EZH2 and the subsequent active methylation of H3K27 occurred during the repair process following DNA damage, as EZH2 and H3K27me3 were enriched at laser induced DNA break sites. Hence, we next asked whether selective inhibition of HDAC1,2 activity impaired DNA repair in the EZH2 gain-of-function mutant DLBCL cells by affecting H3K27me3 that occurred locally at DNA break sites during repair.

Figure 7:
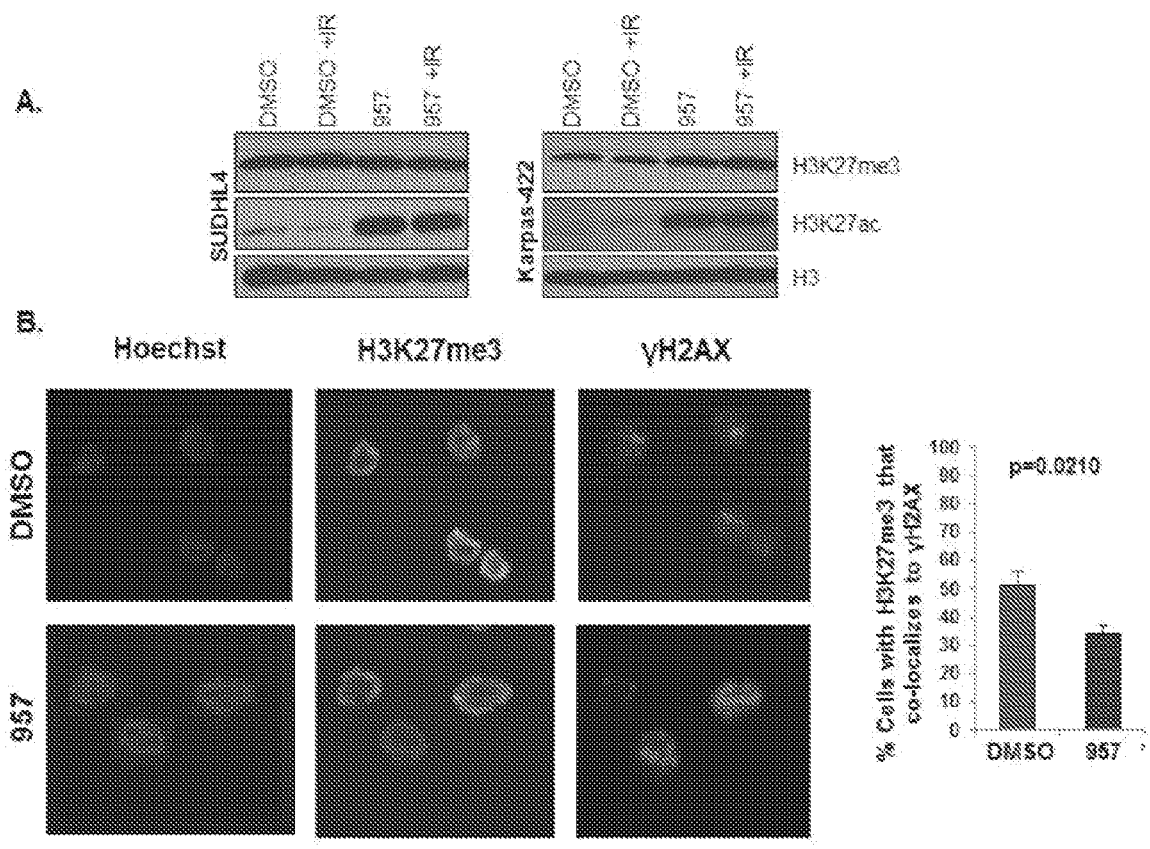
FIG. 7 shows that HDAC1,2 activity did not change global chromatin-associated H3K27me3 following irradiation and are critical for H3K27me3 enrichment at defined laser-induced break sites in chemoresistant DLBCL cells: (A): SUDHL4 and Karpas-422 cells were treated with DMSO or 2 μM ACY-957 for 48 hr. Following DMSO or ACY-957 treatment, cells were exposed to a 5Gy dose of ionizing radiation and allowed to recover for 30 minutes prior to chromatin extraction. Western blots were performed with anti-H3K27ac or anti-H3K27me3 with histone H3 serving as a loading control. (B-E): Karpas-422, SUDHL4, WSU-DLCL2 and HeLa cells were laser micro-irradiated and allowed to recover for 15 minutes before fixation and immunofluorescence staining with anti-γH2AX and anti-H3K27me3. Subsequently, the percentage of cells with H3K27me3 lines that co-localized with γH2AX were counted. Merge is the overlay of γH2AX and H3K27me3 pictures. (F-I): At least 100 cells with γH2AX lines were counted in each experiment. The quantitation shown was the average calculated from independent experiments+/−standard error. Quantitation from five, seven, five and six independent experiments performed in Karpas-422, SUDHL4, WSU-DLCL2 and HeLa cells, respectively, was used in the graph shown in this figure. Statistical analysis was performed and the p-values calculated from the t-test are shown in the figure. (J): Karpas-422 cells were micro-irradiated with a laser and allowed to recover for 15 minutes before fixation and immunofluorescence staining was performed with anti-γH2AX and anti-H3K27ac.

To address this question, we first optimized conditions to induce DNA breaks using a laser in DLBCL cells, which were smaller in size and in suspension compared to other cell types, such as U2OS or HeLa, that were adherent and used in the laser induced break assay. We have determined the optimal laser energy to be applied, the optimum recovery time needed to detect the recruitment of repair proteins or occurrence of histone modification at laser induced break sites in DLBCL cells, and the conditions that promote the adherence of DLBCL cells onto the chamber slide, (see Example 1 above for details). Using the optimized assay, we have detected both γH2AX and H3K27me3 at laser-induced DNA break sites in Karpas-422, SUDHL4 and WSU-DLCL2 cells (FIG. 7, see panels labeled DMSO). We observed that H3K27me3 was enriched at laser induced break sites in DLBCL cells following a 15 min recovery period following exposure to laser (FIGS. 7B-D). Additionally, H3K27me3 was not enriched at laser induced break sites in DLBCL cells after a 5 min recovery (data not shown).

ACY-957 treatment reduced the extent of H3K27me3 present at laser-induced break sites when compared to that present at the break sites in the DMSO treated control cells (FIG. 7). To confirm these results, we performed the laser-break assay in three different EZH2$^{GOF}$ cell lines (Karpas-422, SUDHL4 and WSU-DLCL2) (FIGS. 7B, 7C and 7D). WSU-DLCL2 has an Y641F mutation in the SET domain. We also confirmed this finding in an independent cell line (HeLa) that is routinely used in studies investigating DNA repair dynamics (FIG. 7D). Similar to that observed in the refractory DLBCL cells, decreased H3K27me3 was observed at laser induced break sites in HeLa cells (FIG. 7D). These results indicated that HDAC1,2 activity was required for EZH2-mediated H3K27me3 to occur at break sites during DNA repair.

Figure 14:
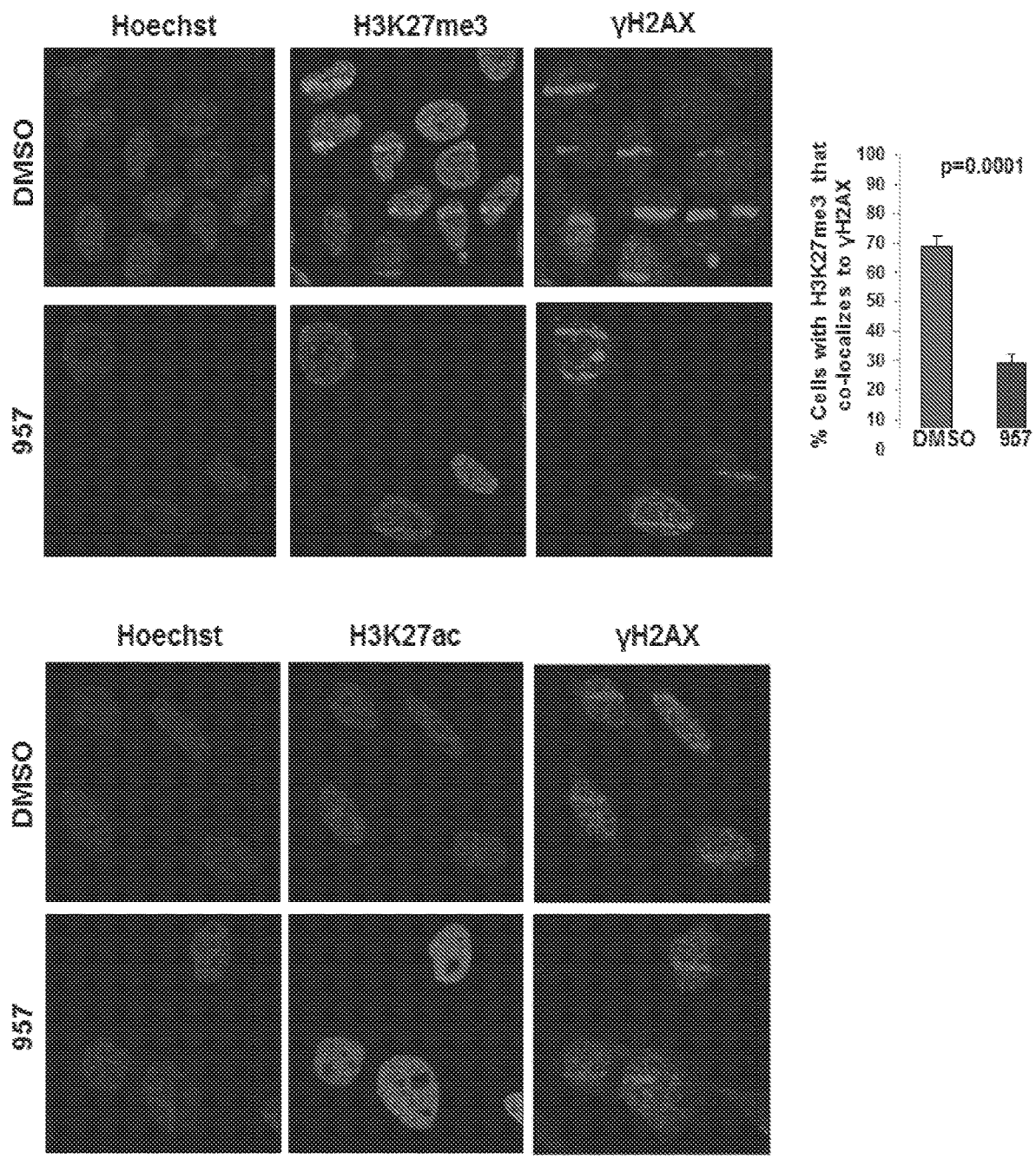
FIG. 14 shows HeLa cells that were laser micro-irradiated and allowed to recover for 15 minutes before fixation and immunofluorescence staining was performed with anti-γH2AX and anti-H3K27ac as described in Example 1.

Given the enrichment of H3K27me3 along with γH2AX at the laser-induced breaks (which appear as a stripe within the nucleus, see FIGS. 7B-7E), we then examined whether H3K27ac forms 'anti-stripe' and was excluded from the laser-induced break sites. A pan-nuclear staining for H3K27ac was observed in DMSO treated control Karpas-422 (FIG. 7J) or HeLa cells (FIG. 14), which was increased following inhibition of HDAC1,2 activities using ACY-957 (FIGS. 7J and 14). H3K27ac was neither enriched at nor excluded from laser-induced break sites in DMSO or ACY-957 treated cells (FIGS. 7J and 14). These results indicated that HDAC1,2 did not remove all the H3K27ac marks at break sites; but they targeted a fraction of H3K27ac (specific or stochastic) in order for the enrichment of H3K27me3 catalyzed by EZH2 to occur at the break sites during DNA repair. In summary, these findings indicated that selective inhibition of HDAC1,2 activity impaired DNA repair in the EZH2 gain-of-function mutant DLBCL cells in part by blocking EZH2-mediated H3K27me3.

Example 9

Chemoresistant EZH2 Gain-of-Function Mutant DLBCL Cells Expressing Hyperactive EZH2 Also Overexpressed the E3 Ligase BBAP GSK126 was a highly selective and potent inhibitor of EZH2 activity, and it targeted the catalytic SET domain. GSK126 treatment of SUDHL4 and Karpas-422 cells led to a significant decrease in H3K27me3 following 48 h treatment of cells with this EZH2 inhibitor (FIG. 4), but viability or cell cycle progression of these chemoresistant DLBCL cells was not compromised at this time point or even after 72 h post-incubation with GSK126 (FIG. 3). These results indicated that a decrease in H3K27me3 alone was not sufficient to trigger death and/or cell cycle arrest in the refractory DLBCL cells in a short time frame. A prolonged 7 days of incubation with GSK126 was required to decrease the viability of Karpas-422 cells. EZH2 gain-of-function mutant DLBCL cells appeared to be more sensitive to selective inhibition of HDAC1,2 activity than inhibition of EZH2 activity, because we observed death and/or cell cycle arrest in SUDHL4 and Karpas-422 cells as early as 48 h or 72 h following treatment with ACY-957 (FIGS. 3 and 13). These findings together indicated that in addition to H3K27me3, inhibition of HDAC1,2 activity adversely affected other factors that were required for proliferation/survival and/or chemoresistance in these refractory DLBCL cells.

A genetically diverse set of DLBCL cell lines were classified as either sensitive or resistant to chemotherapy based on responsiveness to CHOP chemotherapy regime, which included doxorubicin. Karpas-422 was a chemoresistant DLBCL cell line and SUDHL4 DLBCL cell line was partially resistant to chemotherapy drugs when compared to the sensitive SUDHL8 DLBCL cell line. Deltex (DTX)-3-like E3 ubiquitin ligase (DTX3L), also known as B-lymphoma and BAL-associated protein (BBAP), was overexpressed in high risk, chemotherapy-resistant aggressive form of DLBCL. BBAP was required for the monoubiquitination of histone H4K91 (H4K91ub1) and may protect cells from death when exposed to DNA-damaging agents. Accordingly, BBAP and H4K91ub1 may also contribute to the chemoresistance and/or survival of the DLBCL cells. We therefore tested whether chemoresistant DLBCL cells with gain-of-function mutation in EZH2 also expressed higher levels of BBAP compared to the chemosensitive DLBCL cells.

We prepared extracts for Western blotting from EZH2 gain-of-function mutant DLBCL lines (Karpas-422, SUDHL4) and a chemosensitive EZH2 wild-type DLBCL line (SUDHL8). Extracts from NALM6 (a pre-B ALL line), HeLa (a cervix adenocarcinoma line), mouse NIH3T3 cells and mouse fibrosarcoma cells were included for comparison. Additionally, extracts from HeLa cells transfected with either a non-targeting siRNA (siNT) or one of the two siRNAs targeting the BBAP transcript were also included as controls.

Western analysis showed that BBAP levels were higher in the chemoresistant Karpas-422 when compared to SUDHL4 cells and the chemosensitive SUDHL8 cells (FIG. 8A). Amongst the EZH2 gain-of-function mutant DLBCL lines, Karpas-422 was more chemoresistant than SUDHL4; BBAP levels were higher in the former than the latter (FIG. 8A). Additionally, BBAP levels were high in the chemoresistant Nalm6 cells (FIG. 8A). These results together showed a correlation between chemoresistance and elevated BBAP levels. Refractory DLBCL cells contained a hyperactive EZH2 and EZH2 was important for DNA repair (FIG. 6), but inhibition of EZH2 activity alone was not sufficient to cause cytotoxicity in these cells (FIG. 3). BBAP was required for the efficient repair of double strand DNA breaks, and BBAP-mediated H4K91ub1 was increased upon exposure of cells to doxorubicin (a DNA-damaging chemotherapy drug). The increased BBAP levels in the refractory DLBCL cells may promote repair of the DNA damage induced by chemotherapy drugs via increased H4K91ub1 to confer chemoresistance and support the proliferation/survival of these cells.

Example 10

Selective HDAC1,2 Inhibition Increased H4K91Ac and Decreased the DNA Damage Induced, BBAP-Mediated Ubiquitination of H4K91 in the EZH2 Gain-of-Function Mutant DLBCL Cells The H4K91 residue is involved in DNA repair in yeast and mammalian cells. H4K91 undergoes chemically exclusive modifications, acetylation and ubiquitination, in mammalian cells. Therefore, we hypothesized that selective inhibition of HDAC1,2 activity may increase H4K91ac to block BBAP-mediated H4K91ub1 and impair DNA repair in the chemoresistant DLBCL cells.

To test this possibility, we performed acid extraction of nuclei isolated from either DMSO or ACY957 treated Karpas-422 and SUDHL4 cells to obtain histones-enriched fractions. We used the acid extraction procedure to not only enrich for the highly basic histone proteins, but to also prevent the loss of histone ubiquitination, which was a labile modification that was removed by the action of deubiquitinases within the cell. Western analysis of acid-extracted histones showed that inhibition of HDAC1,2 activity increased global H4K91ac levels in both SUDHL4 and Karpas-422 cells (FIG. 8B), and therefore, revealed that H4K91ac was a target of HDAC1,2.

Additionally, ACY-957 treatment also increased global levels of H4K16ac (FIG. 8B), which is a target of HDAC1,2. H4K16ac occurred at the N-terminal tail region and disrupted chromatin packaging by preventing inter-nucleosomal interactions. On the other hand, the H4K91 residue was present at the interface between the H3-H4 tetramer core and the H2A-H2A dimer within the nucleosome, and acetylation at this residue may weaken nucleosome stability by preventing the salt bridge formation and adversely affect chromatin assembly. Therefore, these results together indicated that Hdacs1,2 play a role in nucleosome and chromatin dynamics in the chemoresistant DLBCL cells.

We next examined whether global H4K91ub1 was impacted upon selective inhibition of HDAC1,2 activity in DLBCL cells. Covalent addition of a bulky 7.6-kDa ubiquitin moiety onto the H4K91 residue retarded gel migration, resulting in slower migrating species of H4.

We further treated HeLa cells transfected with a plasmid to express a Flag-Myc epitope-tagged H4 or Flag-Myc epitope-tagged H4 mutant harboring a lysine to arginine substitution at position 91 (H4K91R) and exposed to doxorubicin. As shown in FIG. 8C, H4K91ub1 induced by doxorubicin was reduced by H4K91R mutation.

An antibody recognizing H4K91ub1 was not available. We therefore used an anti-histone H4 antibody in the Western analysis of acid-extracted histones obtained from SUDHL4 or Karpas-422 cells treated for 30 h (FIG. 8D) or 48 h (data not shown) with DMSO or ACY-957, which showed no change in global levels of the slow migrating monoubiquitinated form of H4. This result indicated that inhibition of HDAC1,2 activity did not affect preexisting H4K91ub1 marks. H4K91ub1 levels were increased when cells are exposed to DNA-damaging agents, such as, doxorubicin.

Given the increase in global H4K91ac with ACY957 treatment (FIG. 8B), we next asked whether active monoubiquitination of H4K91 catalyzed by BBAP was regulated by HDAC1,2 activity. We treated Karpas-422 or SUDHL4 cells with DMSO or ACY-957 for 48 h prior to the incubation for 4 h or 8 h in the presence of doxorubicin. Western analysis of acid-extracted histones showed a significant reduction to complete absence of the slow migrating monoubiquitinated form of H4 in ACY-957-treated Karpas-422 or SUDHL4 cells, respectively (FIG. 8E). Collectively, these results showed that HDAC1,2 activity was required for BBAP-catalyzed active H4K91ub1 to occur when DLBCL cells were exposed to doxorubicin, a chemotherapy drug and a DNA-damaging agent.

Example 11

Figure 8:
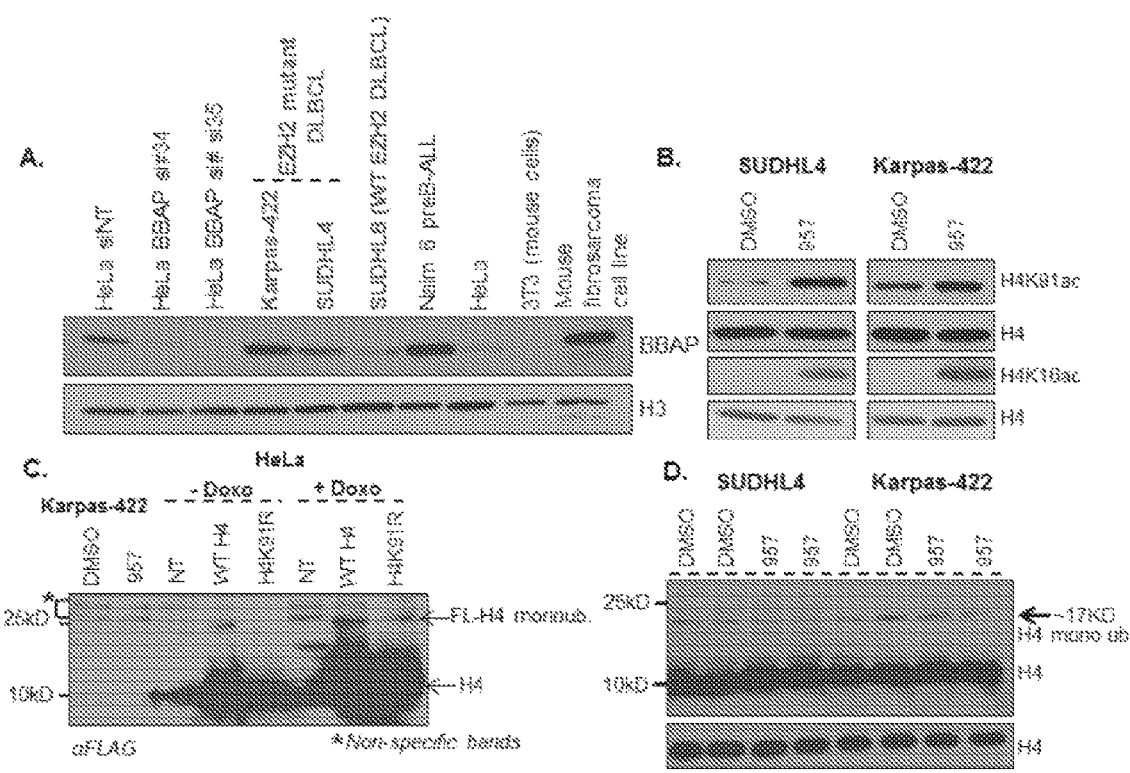
FIG. 8 shows that EZH2 gain-of-function mutant DLBCL cells also over expressed BBAP E3 ligase, HDAC1,2 target H4K91ac and inhibition of HDAC1,2 activity decreased H4 monoubiquitination following doxorubicin treatment: (A): Whole cell lysate was prepared from Karpas-422, SUDHL4, SUDHL8, Nalm6, HeLa, NIH3T3, and mouse fibrosarcoma cell lines. Western analysis was performed with anti-BBAP antibody and histone H3 was used as a loading control. Whole cell lysate of HeLa cells was prepared following transfection of cells with either non-targeting or two different BBAP siRNAs. These extracts served as negative controls for the signal from BBAP antibody. (B): SUDHL4 and Karpas-422 cells were treated with DMSO or 2 μM ACY-957 for 48 hr prior to chromatin extraction. Western analysis was done using anti-H4K91ac or anti-H4K16ac and histone H4 served as a loading control. (C): HeLa cells were transfected with either wild type H4 or H4K91R mutant constructs for 65 hours prior to extraction of histones by trichloroacetic acid. Western blot analysis was performed with anti-FLAG antibody. (D): SUDHL4 cells and Karpas-422 were treated with DMSO or 2 μM ACY-957 for 24 hours and histones were extracted by TCA precipitation. Western blotting with anti-H4 was performed to detect H4 and monoubiquitylated H4. (E): SUDHL4 cells and Karpas-422 were treated with DMSO or 2 μM ACY-957 for 48 hours and treated with 50 nM doxorubicin for 4 hr or 8 hr prior to histone extraction. Histones were extracted by TCA precipitation and western blotting with anti-H4 was performed to detect H4 and monoubiquitinated H4.

Selective Inhibition of HDAC1,2 Activity Delayed the Kinetics of BBAP-Dependent 53BP1 Recruitment to Chemo-Induced DNA Break Sites Knockdown of BBAP delayed the accumulation of 53BP1 (a repair protein) at DNA breaks induced by doxorubicin, suggesting that BBAP, via H4K91ub1, protected DLBCL cells from DNA damage by facilitating 53BP1-mediated repair of double-strand DNA breaks. Active BBAP-mediated H4K91ub1 induced by doxorubicin was inhibited when cells were pretreated with ACY-957 (FIG. 8). Therefore, we hypothesized that selective inhibition of HDAC1,2 activity may impair DNA repair in EZH2 gain-of-function mutant chemoresistant DLBCL cells by delaying the recruitment of 53BP1 to DNA break sites as a result of increased H4K91ac and decreased H4K91ub1.

To test this possibility, we treated DLBCL cells with DMSO or ACY957 for 24 h prior to a low dose of doxorubicin (50 nM) treatment. We examined γH2AX and 53BP1 foci formation at 4 h or 8 h post-doxorubicin treatment using immunofluorescence. We chose a 24 h ACY-957 treatment for this assay as we did not detect any significant accumulation of endogenous DNA damage resulting from inhibiting HDAC1,2 activity using this treatment time, unlike that observed when cells were treated with ACY-957 for 48 h (FIG. 6). Thus, this short duration of inhibitor treatment enabled us to bypass the DNA repair events triggered by endogenous DNA damage in the absence of HDAC1,2 activity and directly follow the kinetics of doxorubicin-mediated DNA repair upon inhibiting HDAC1,2. Immunofluorescence showed co-localization of 53BP1 with γH2AX at 4 h and 8 h following addition of doxorubicin to the control DMSO-treated Karpas-422 cells (FIG. 9).

The percentage of cells containing 0, 1-5, 6-10 and greater than 10 γH2AX and 53BP1 foci were determined in at least 100 cells from three independent experiments. Quantitation of the percentage of cells with 53BP1 foci co-localizing with γH2AX foci revealed a decrease in the number of 53BP1 foci in ACY-957-treated Karpas-422 cells at 4 h post-doxorubicin treatment when compared to DMSO-treated controls (FIG. 9). Following an 8 h treatment with doxorubicin, the percentage of cells with 1-5, 6-10, and greater than 10 53BP1 foci in ACY-957-treated cells increased to the level that was observed in the control DMSO-treated cells. However, ACY-957-treated cells had an even higher percentage of cells with 6-10 and greater than 10 γH2AX foci compared to DMSO-treated control cells at this 8 h time point (FIG. 9). These results together indicated that HDAC1,2 activity were required for the initial recruitment of 53BP1 to DNA break sites following exposure to doxorubicin. These results also indicated that pretreatment of EZH2 gain-of-function mutant DLBCL cells with HDAC1, 2-selective inhibitor sensitized cells to doxorubicin, which resulted in increased DNA damage response and increased number of γH2AX-containing double-strand breaks. However, the repair of these breaks was impaired in the absence of HDAC1,2 activities as the majority of γH2AX-containing break sites did not also contain 53BP1 repair protein.

Example 12

Figure 9:
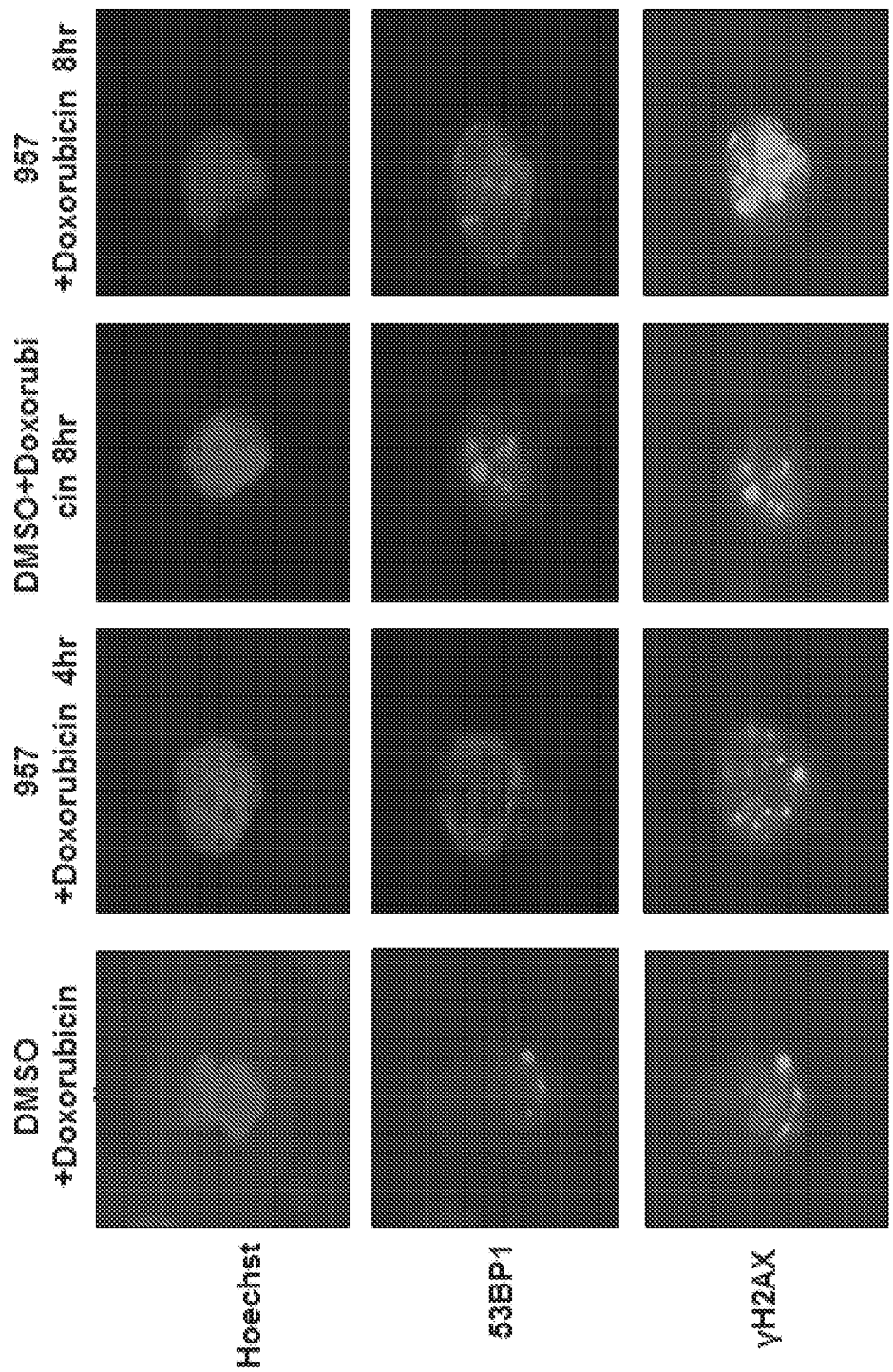
FIG. 9 shows that HDAC1,2 inhibition delayed the kinetics of 53BP1 foci formation in refractory EZH2-mutant DLBCL cells: (A): Karpas-422 cells were treated with either DMSO or 2 μM ACY-957 for 24 h before the addition of doxorubicin. After 4 h or 8 h of doxorubicin treatment, cells were fixed and immunofluorescence staining was performed with anti-γH2AX and anti-53BP1 antibodies. Cells shown were representative images based on the quantitation. Merge was the overlay of γH2AX and 53BP1 pictures. (B) and (C): Graphs depicted the percentage of cells with 53BP1 foci present at γH2AX containing break sites and the percentages of cells with γH2AX foci. The data represented the average +/−standard error from four independent experiments. *p=0.05; **p=0.009.
Figure 10:
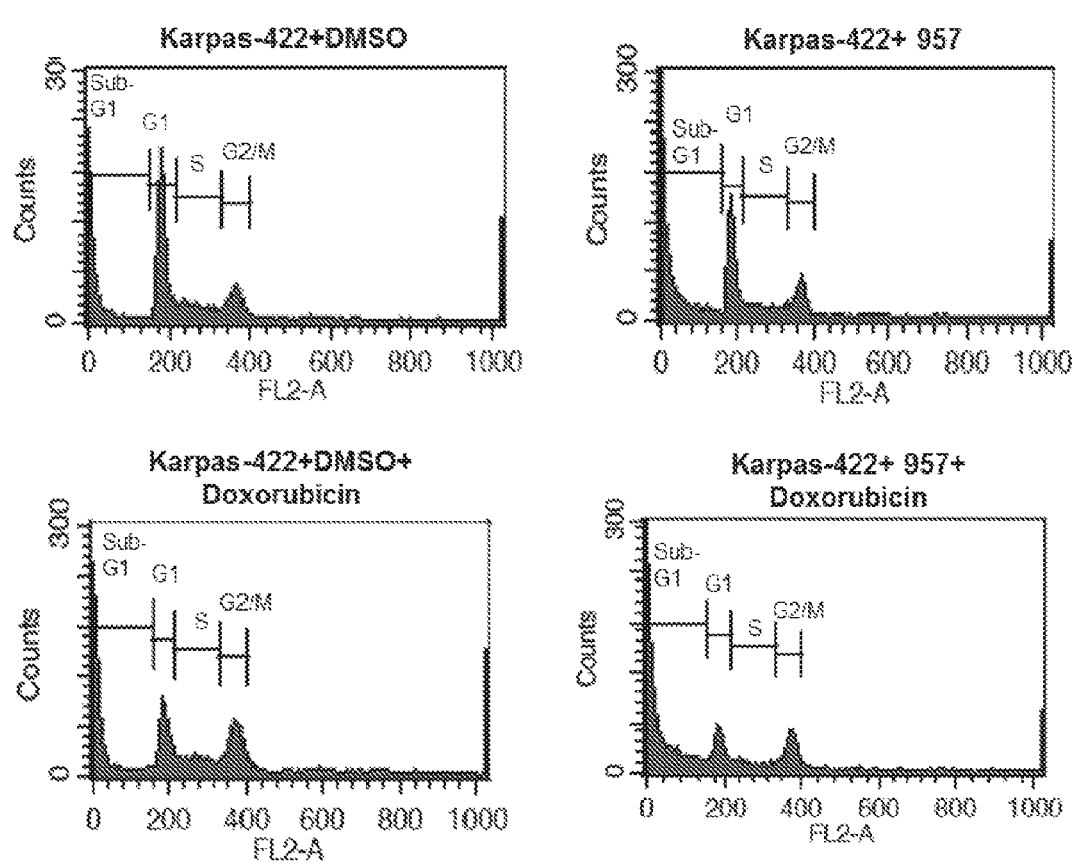
FIG. 10 shows that HDAC1,2 inhibition sensitized chemoresistant Karpas-422 cells to doxorubicin induced cell death: (A): Karpas-422 cells were treated with DMSO, 2 μM ACY-957, 50 nM doxorubicin or ACY-957 plus 50 nM doxorubicin for 48 h. Cell cycle analysis of propidium-iodide stained cells was performed with fixed cells. Representative plots from five independent experiments are shown in the figure. (B): The graph represented average percentage cells+/−standard error of five independent experiments. *p=0.003, **p=0.005. (C): FACS analysis following BrdU-PI staining of Karpas-422 and SUDHL4 cells was performed following a treatment with 2 μM ACY-957, 50 nM doxorubicin or both for 48 h. Representative plots from two independent experiments are shown in the figure.
Figure 11:
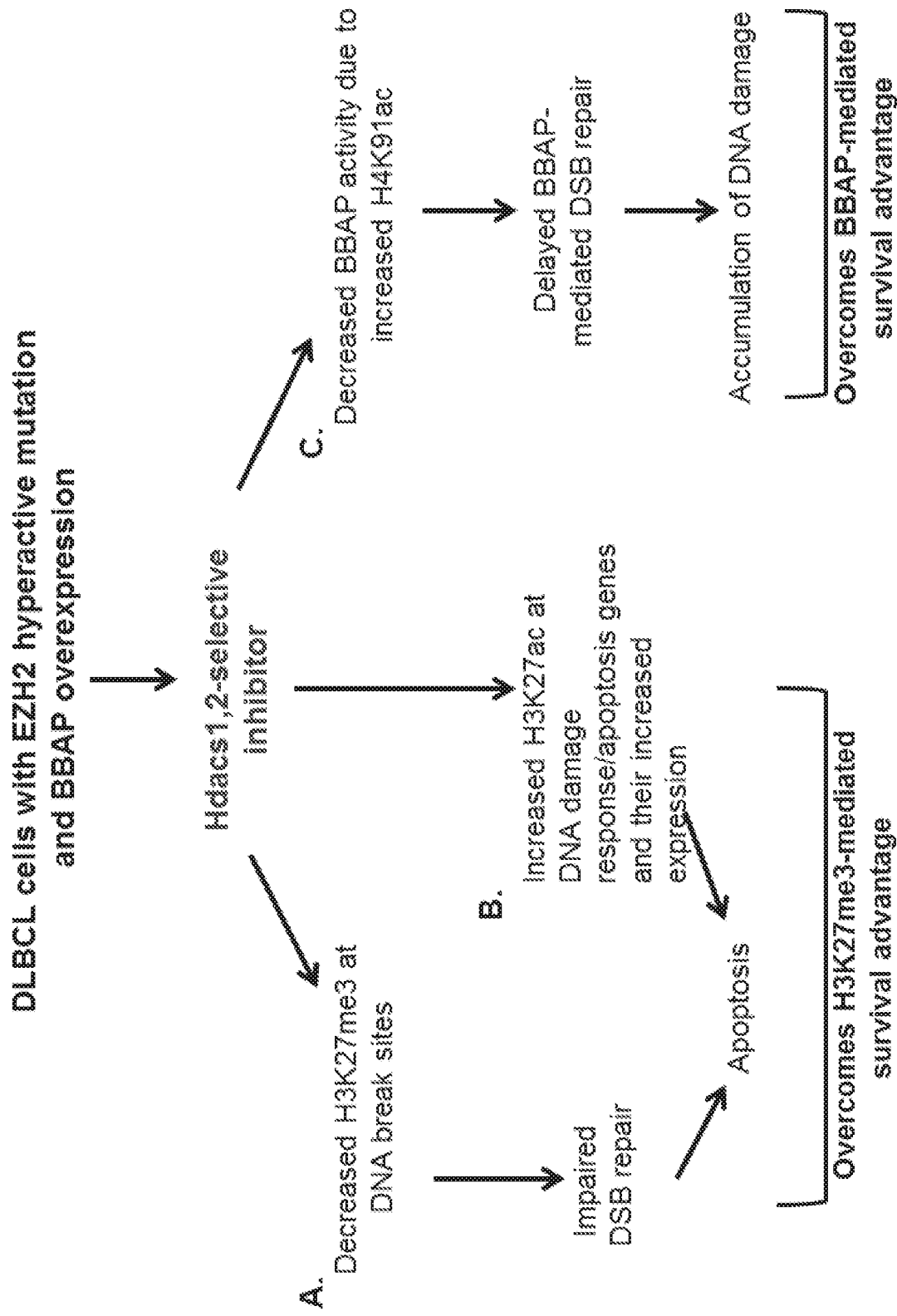
FIG. 11 shows a model for the mechanism of action of HDAC1,2-selective inhibitor in EZH2 gain-of-function mutant DLBCL cells: (A): HDAC1,2 selective inhibition decreased H3K27me3 at break sites to impair DSB repair and activated DNA damage response. (B): HDAC1,2 inhibition increased H3K27ac at DNA damage response genes to increase their transcription. (A) and (B) together overcame the survival advantage provided by increased H3K27me3 in these EZH2 gain-of-function DLBCL cells. (C): HDAC1,2 inhibition increased H4K91ac and decreased H4K91 monoubiquitination following doxorubicin treatment. This resulted in a defective 53BP1 recruitment to damage sites and defective repair of doxorubicin-induced breaks. Hence, Hdac1,2 inhibition overcame BBAP-mediated chemoresistance following doxorubicin treatment in DLBCL cells with EZH2 hyperactive mutation.

Treatment with HDAC1,2 Selective Inhibitor Sensitized the EZH2 Gain-of-Function Mutant Refractory DLBCL Cells to Doxorubicin BBAP knockdown sensitized HeLa cells to doxorubicin-induced cell death and inhibition of HDAC1,2 activity decreased H4 monoubiquitination and 53BP1 recruitment during doxorubicin-induced DSB repair (FIGS. 8, 9). Hence, it was examined whether Hdac1,2 inhibition could sensitize the chemorefractory EZH2$^{GOF}$ Karpas-422 cells to doxorubicin treatment and overcome drug resistance. To test this possibility, cell cycle analysis following treatment of Karpas-422 with ACY-957, doxorubicin, or ACY-957 in combination with doxorubicin was performed. Karpas-422 cells showed a 1.5 to 2-fold increase in the percentage of cells in G2/M phase with a modest increase in cell death upon doxorubicin treatment (FIG. 10A). Additionally, a sub-G1 population (i.e., dead cells) was observed following ACY-957 treatment of Karpas-422 cells (FIG. 10A). However, combined treatment of Karpas-422 cells with doxorubicin and ACY-957 resulted in an increased sensitivity of cells to death, as the sub-G1 population increased by about 5-fold when compared to DMSO control (FIG. 10A). BrdU-PI analysis also showed a consistent increase in sub-G1 population upon combined application of ACY-957 and doxorubicin to Karpas-422 cells (FIG. 10B). The results therefore indicated that HDAC1,2 inhibition overcame doxorubicin-resistance in the refractory EZH2$^{GOF}$ Karpas-422 cells by impairing BBAP-mediated DSB repair via H4K91ub1 in addition to EZH2-mediated DSB repair via H3K27me3.

In summary, Examples 2-12 demonstrated that selective inhibition of histone deacetylase 1,2 (HDAC1,2) activity using a small molecule inhibitor caused cytotoxic or cytostatic effects in EZH2 gain-of-function mutant (EZH2$^{GOF}$) DLBCL cells. Our results showed that blocking the activities of HDAC1,2 increased global H3K27ac without causing a concomitant global decrease in H3K27me3 levels. Our data showed that inhibition of HDAC1,2 was sufficient to decrease H3K27me3 present at double-stranded breaks (DSBs), decrease DSB repair and activate the DNA damage response in these cells. In addition to increased H3K27me3, we found that the EZH2$^{GOF}$ DLBCL cells overexpressed another chemotherapy resistance factor—B-lymphoma and BAL-associated protein (BBAP). Our results showed that selective inhibition of HDAC1,2 increases H4K91ac, decreases BBAP-mediated H4K91 monoubiquitination, impairs BBAP-dependent DSB repair and sensitizes the refractory EZH2$^{GOF}$ DLBCL cells to treatment with doxorubicin, a chemotherapy agent. Hence, selective Hdacs1,2 inhibition provided a DNA repair mechanism-based therapeutic approach as it overcame both EZH2- and BBAP-mediated DSB repair in the EZH2$^{GOF}$ DLBCL cells.

Example 13

Small Molecule Inhibitors to Selectively Inhibit HDAC1 and HDAC2

Figure 17:
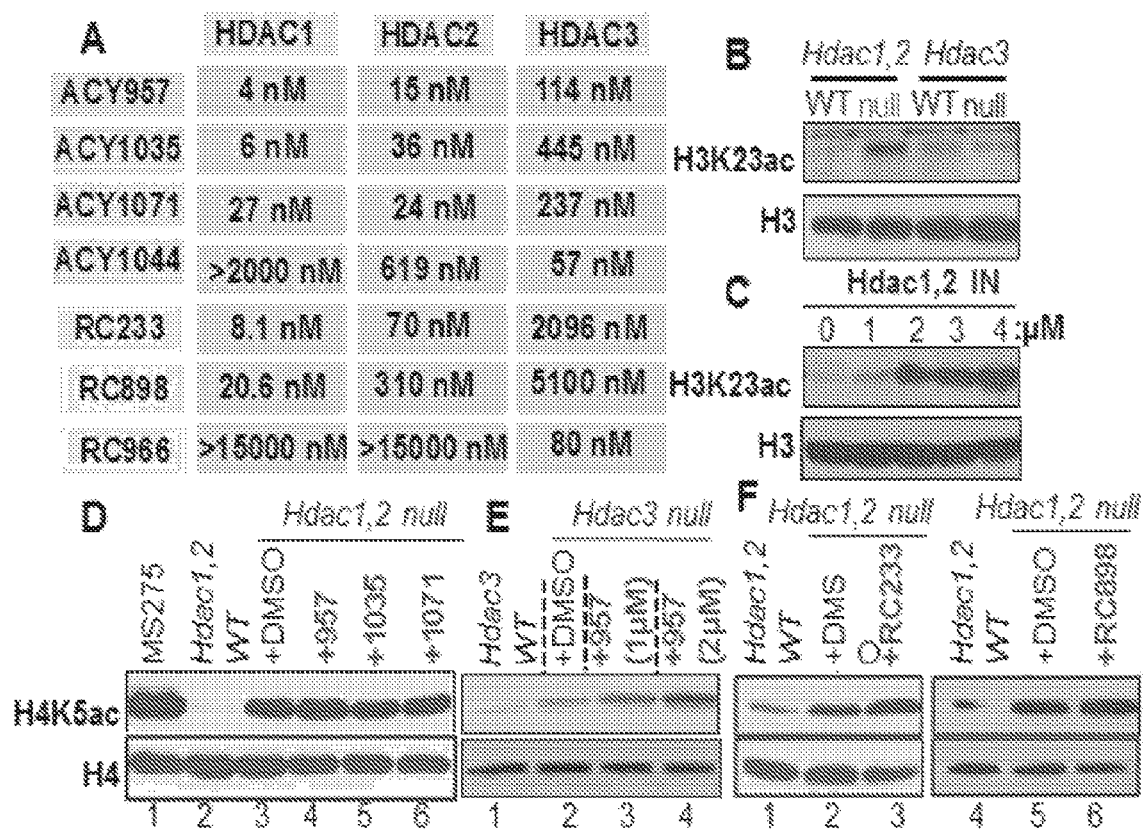
FIG. 17 shows confirmation of the selectivity of HDAC1,2 inhibitors. (A). For $IC_{50}$ determination, recombinant HDAC enzymes were treated with HDAC1,2 or HDAC3 inhibitors in in vitro HDAC assays. (B). Western blots for H3K23ac using extracts from Pre-B-ALL SupB15 cells treated with increasing dose of HDAC1,2 inhibitor (ACY1035). (C). Hdac1$^{Fl/Fl}$, 2$^{Fl/Fl}$ cells were infected with Ad-Cre virus to delete HDAC1 and HDAC2 (HDAC1,2 null) or uninfected (WT). (D). Hdac3$^{Fl/Fl}$ cells were either uninfected (WT) or infected with Ad-Cre virus to delete Hdac3. HDAC3-null cells were treated with DMSO or the HDAC1,2 selective inhibitor.

IC50 values obtained from in vitro enzyme assays showed that compounds ACY1035, ACY957, ACY1071 inhibited Hdac1,2 activities very selectively compared to Hdac3 (FIG. 17A). We have determined 2 µM (FIG. 17B) as the minimum dose for the ACY compounds, respectively, that when added to cells increased H3K23ac (a mark targeted by Hdac1,2 but not Hdac3).

We have rigorously validated the selectivity of all the Hdac1,2 inhibitors in hand using conditional Hdac1,2 or Hdac3 knockout cell lines and by examining changes in H4K5ac (a mark targeted by Hdacs1,2 and 3). We reasoned that when Hdac1,2 are deleted from cells, an Hdac1,2 selective inhibitor will lack its target enzymes and therefore it cannot change H4K5ac levels any further. If however H4K5ac levels are increased in Hdac1,2-null cells upon adding an Hdac1,2 inhibitor, then it would mean that this compound has an off-target effect and inhibits Hdac3 activity. Confirming their target selectivity, our Hdac1,2 inhibitors did not increase H4K5ac when added to Hdac1,2 knockout cells (compare lanes 4-6 to lane 3 in FIG. 17C).

Addition of ACY957 (FIG. 17D) to Hdac3-null cells resulted in an additive increase in H4K5ac (compare lanes 3-4 to 2 in FIG. 17D), due to the loss of Hdacs1,2&3 activities.

MS275 is a benzamide-class inhibitor of Hdacs1, 2 and 330, and it caused a greater increase in H4K5ac than the deletion of just Hdac1,2 (compare lane 3 to 1 in FIG. 17C). If an Hdac1,2 selective inhibitor targeted Hdac3, then it would be functionally equivalent to MS275; but H4K5ac levels following Hdac1,2 inhibition were not similar to that seen in MS275 treatment (compare lanes 4-6 to 1 in FIG. 17C).

The Hdac1,2 inhibitors in hand were designed to hit the zinc-binding pocket that was not present in Class III sirtuin HDACs. Also, these Hdac1,2 and Hdac3 inhibitors in hand belonged to amino-benzamide class of inhibitors (similar to MS-275) that only inhibited Hdacs1-344. Also, biochemical data showed that Hdac1,2 or Hdac3 inhibitors did not inhibit Class II Hdacs.

Moreover, Hdac1,2 inhibitors did not increase Smc3 acetylation, a target of Hdac8, another Class I HDAC. Therefore, all our results together confirmed that the ACY compounds were highly selective inhibitors of Hdac1,2. Further endorsing the utility of these compounds for our studies, phenotypes obtained using these Hdac1,2 selective inhibitors agreed very well with those obtained using genetic systems to delete Hdac1,2. We also have pharmacokinetic (PK) data for these compounds for our in vivo experiments in mice.

Example 14

Figure 18:
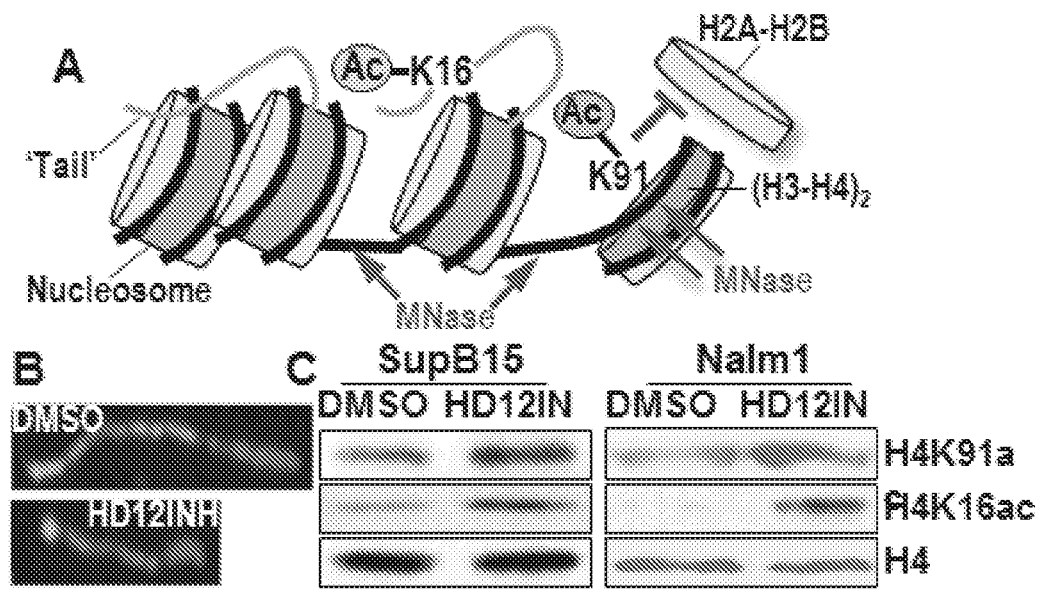
FIG. 18 in (A) shows a model for how HDAC1,2 regulated inter- and intra-nucleosomal interactions by targeting H4K16ac and H4K91ac, respectively. (B). Inhibition of HDAC1,2 increased global H4K91ac and H4K16ac in Ph+ Pre-B-ALL cell lines.

H4K91Ac is a Histone Target of HDAC1,2 and Involved in Nucleosome Assembly and DNA Repair In addition to increased release of nucleosomes from chromatin, we also noticed increased MNase digestion of mononucleosomes at candidate replicating loci following Hdac1,2 inhibition, indicating that Hdac1,2 may affect nucleosome assembly in addition to chromatin packaging. How may Hdac1,2 affect both chromatin packaging and nucleosome assembly? H4K16ac increased chromatin accessibility to MNase digestion by inhibiting the inter-nucleosomal interactions mediated by the H4 'tail' domain to promote chromatin decompaction (FIG. 18A). H4K91ac influenced nucleosome assembly by regulating H3-H4 tetramer core interaction with the H2A-H2B dimers48 (FIG. 18A). Hdac1,2 inhibition caused an increase in global H4K91ac in Ph+Pre-B-ALL cells (FIG. 18B). We have therefore uncovered H4K91ac as a histone target of Hdac1, 2. Increased H4K91ac following Hdac1,2 inhibition may prevent H2A-H2B deposition onto H3-H4 tetramer and disrupt nucleosome assembly, which in turn may result in an unstable nucleosome/chromatin that was prone to DNA damage in cancer cells, including Pre-B-ALL, and thus providing another mechanism for Hdac1,2 inhibitor action.

Example 15

FEN1 is a Nuclease Involved in Processing DNA During Replication and Repair, and is a Non-Histone Target of HDAC1,2

We asked whether Hdac1,2 contributed to replication and repair by regulating non-histone protein acetylation. Using quantitative mass spectrometry following IP with an a-pan-acetyllysine antibody, we identified FEN1 as a non-histone target of Hdac1,2 (FIG. 19A). Mass spectrometry revealed acetylation of a lysine (K375) near the C-terminal region of FEN1 was increased 18-fold following treatment with Hdac1,2 selective inhibitor (FIG. 19A). We have confirmed that FEN1 acetylation was increased upon Hdac1,2 inhibition in Pre-B-ALL cells (FIG. 19B).

Figure 23:
FIG. 23 shows that (A) FEN1 interacted with PCNA at replication forks, where it was involved in removing the 5'-flap structures as part of the Okazaki fragment maturation process. The RNA primer is also shown. (B). Upon replication stress, FEN1 was recruited by WRN, the helicase, to process aberrant replication intermediates. (C). DNA damage in SupB15 cells following shRNA-mediated knockdown of endogenous FEN1 and re-expression of wild-type FEN1 or FEN1-K375 mutants. Merged IF images were shown. (D). Homologous recombination (HR) repair in the presence of DMSO or the HDAC1,2 inhibitor was measured using cells expressing BCR-ABL and containing a stably integrated DR-GFP reporter cassette. HR quantitation was done.

Our results also showed that mutating the K375 residue in FEN1 caused DNA damage in Pre-B-ALL cells (FIG. 23C), indicating a function for this residue in genome maintenance. This identification of FEN1 as a target of Hdac1,2 provided yet another avenue by which selective inhibition of these enzymes may be used to restrict the growth of cancer cells. Increased FEN1 acetylation upon Hdac1,2 inhibition led to an S-phase arrest as a result of aberrant processing of Okazaki fragments or caused mitotic catastrophe due to DNA damage introduced in S-phase. This puts forth another mode of Hdac1,2 inhibitor action, that by targeting a non-histone genome regulatory protein they caused genotoxic stress in cancer cells.

Example 16

HDAC1,2 are Therapeutic Targets for Early B-Cell Derived Acute Lymphoblastic Leukemia Acute lymphoblastic leukemia (ALL) is a fast-growing cancer of the lymphocyte-forming cells (the lymphoblasts) with >3200 new cases reported in the United States per year; 80-85% of these cases are precursor B-cell ALL (Pre-B-ALL). Pre-B-ALL is characterized by the presence of onco-genic BCR-ABL fusion protein, which increased homologous recombination based DNA repair in cycling leukemic cells to prevent apoptosis.

Figure 20:
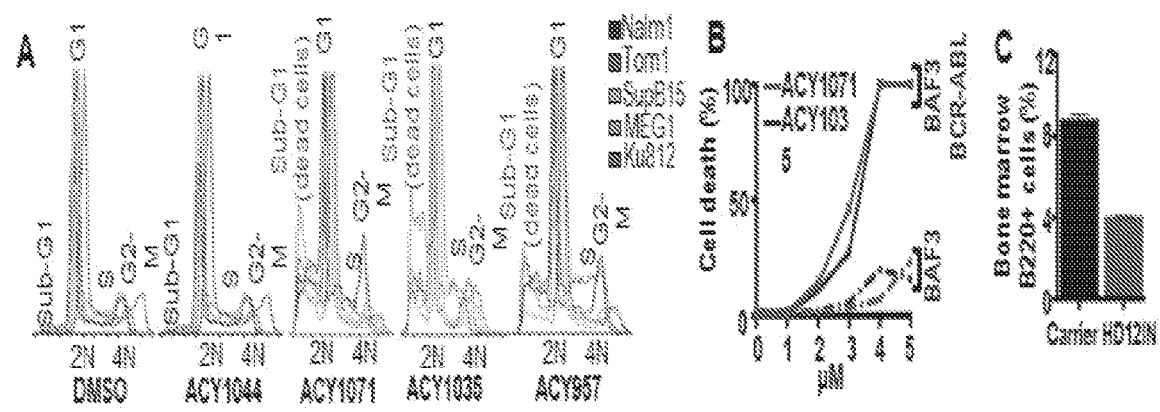
FIG. 20 shows in (A) five BCR-ABL expressing cell lines that were treated with DMSO, HDAC3 inhibitor (1044) or three HDAC1,2 selective inhibitors for 96 h. FACS was performed following propidium-iodide staining (PI). (B). BCR-ABL transformed or non-transformed murine Baf3 cells were treated with increasing dose of ACY1035 or ACY1071. Cells in subG1 phase (dead cells) were measured using FACS after PI. (C). Wild-type mice injected with 50 mg/kg body weight of ACY1035 or cyclodextrin carrier every day for 5 days. FACS was used to measure percentage B220+ B-cells in total bone marrow cells isolated from these mice. (D). % B220+ B-cells in the peripheral blood of mice treated with ACY1035 for 5 days or after a week of recovery without inhibitor treatment. % B220+ B-cells from bone marrow and spleen after recovery are also shown. C, carrier; T, HDAC1,2 inhibitor. (E). FACS profiles for B220+CD43+ population isolated from bone marrow of mice with or without recovery from inhibitor treatment. In (E), arrows indicated decrease in B-cells upon inhibitor treatment and their reemergence following recovery from inhibitor treatment. Mice treated with ACY1035 as described for panel (C). (F). FACS profiles for LSK+ stem and progenitor cells (Lineage negative, cKit+, Sca-1+) isolated from bone marrow of control or HDAC1,2 inhibitor treated mice. (G). SupB15 cells were treated with HDAC1,2 inhibitor for 24 h and molecular combing was done to measure fork velocity. Average fiber length were shown on the side. (H). Representative IF image for SupB15 cells, Ph+ mononuclear cells and Ph+ stem/progenitor cells was shown in panels (H-J). Merged IF images for γH2AX foci and Hoechst, nuclear stain were shown. (K). Quantitation of DNA damage in CD34+ stem/progenitor cells isolated from normal bone marrow and Ph+ patient bone marrow. DNA damage was measured using immunofluorescence (IF) staining for γH2AX.

We asked whether Hdac1,2 inhibition impaired BCR-ABL mediated hyperactive DNA repair to cause DNA damage and death in Ph+Pre-B-ALL cells. Hdac1,2 inhibitors caused significant cell death in three Ph+Pre-B-ALL cell lines (Nalm1, Tom1 and SupB15) (FIG. 20A). This effect was specific for Hdac1,2 inhibition, as treatment with a Hdac3 inhibitor (ACY1044) did not cause any cell death (FIG. 20A). Similar results were also obtained for MEG1 and Ku812 cells, which were BCR-ABL expressing chronic myeloid leukemia (CML) lines (FIG. 20A).

Hdac1,2 selective inhibitors caused a significant dose-dependent cell death in BCR-ABL transformed, but not in the control non-transformed, mouse IL-3 dependent immortalized Pro-B Baf3 cells (FIG. 20B). Overall, these results showed that BCR-ABL expressing cells were sensitive to Hdac1,2 inhibition.

SAHA, the FDA approved pan-HDI that targets 10 different Class I and Class II HDACs, showed anti-tumor activity in a mouse model of Pre-B-ALL. Since inhibition of Hdac1,2 (i.e., only 2 of the 10 SAHA targets) was sufficient to kill Ph+leukemic cells (FIG. 20A), our studies indicated that selective, isotype-targeted inhibition of individual HDACs may be a clinically effective therapeutic strategy that can avoid side effects resulting from unnecessary targeting of multiple HDACs with important cellular functions.

Deletion of Hdac1,2 in mice led to a block in B-cell development. Treatment of mice with Hdac1,2 inhibitor decreased B220+B-cells in the bone marrow (FIG. 20C), peripheral blood and spleen (data not shown). However, normal B220+ B-cell population reappeared in within 7 days after stopping Hdac1,2 inhibitor treatment (FIG. 20D). Normal B220+CD43+ (early, immature) and B220+CD43− (late, mature) B-cell population were also observed in the bone marrow following recovery from Hdac1,2 inhibition (FIG. 20E). Moreover, LSK+ stem and progenitor cell population in bone marrow remained unaffected by Hdac1,2 inhibition (FIG. 20F), and this explained the revival of normal B-cell population upon removing the inhibitor. Overall, transient inhibition of Hdac1,2 did not result in any irreversible block in B-cell development (FIG. 20E).

Hdac1,2 inhibition reduced replication fork velocity, activated DNA damage response in Ph+Pre-B-ALL SupB15 cells (FIGS. 20G and 20H) and in mononuclear cells obtained from a Ph+Pre-B-ALL patient (FIG. 20I). These results showed that Hdac1,2 inhibitors were effective in cycling Ph+leukemic cells.

Hdac1,2 inhibition did not cause any significant DNA damage in normal stem/progenitor cells obtained from a healthy individual, but it triggered DNA damage in a vast majority of Ph+ stem/progenitor cells (FIGS. 20J and 20K). Ph+ LSCs have reduced quiescence, increased cell division and higher level of HR repair activity compared to normal hematopoietic stem cells, and given the link between Hdac1,2 and DNA replication, we therefore propose that Hdac1,2 inhibition induced DNA damage in these relatively cycling/replicating LSCs, likely via its direct adverse effects on the nascent chromatin and FEN1 repair activity at replication forks. Based on all these reasons, selective inhibition of Hdac1,2 was an effective therapeutic strategy for treating Ph+Pre-B acute lymphoblastic leukemia, as inhibiting Hdac1,2 activities caused replication stress in cycling cells to induce DNA damage in addition to impairing DNA repair.

Example 17

Where in the S-Phase Genome is H4K16Ac Targeted by HDAC1,2?

To understand how Hdac1,2 affects chromatin structure in S-phase, we will determine whether inhibition of Hdac1,2 increases H4K16ac around replication forks genome-wide. The 'open' euchromatic regions replicate early in S-phase and the condensed heterochromatin replicates late in S-phase. Therefore, use of genome-wide approaches will enable us to obtain a global view of Hdac1,2 functions at and around replication forks present in different chromatin environments.

Figure 21:
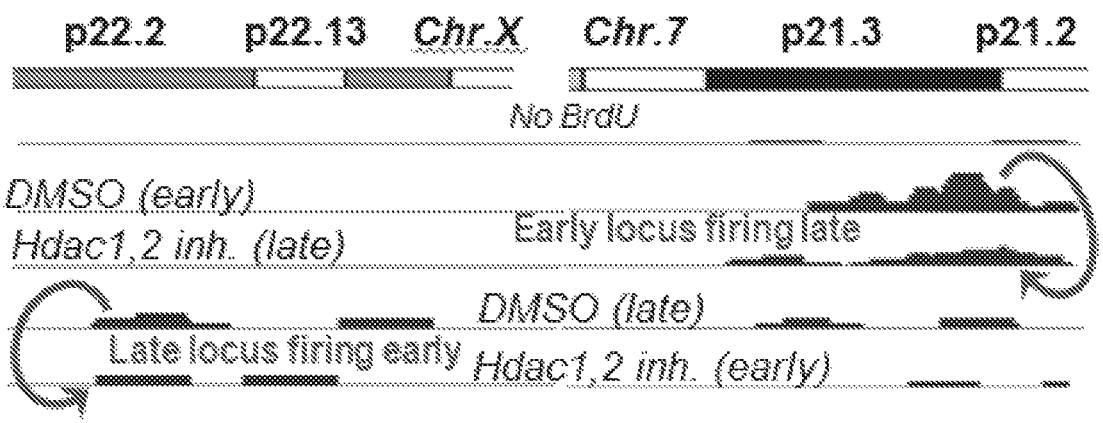
FIG. 21 shows Repli-seq of Ph+Pre-B-ALL SupB15 cells, in particular, representative snapshots of Illumina sequencing data. Signal strengths (number of reads) for BrdU-labeled loci that fire in early or in late S-phase cells treated with either DMSO or the HDAC1,2 inhibitor are shown. Reads obtained for the same loci without BrdU labeling (background) are also shown. Replication timing was changed at these loci in the absence of HDAC1,2 activities.

In order to determine the sites of DNA replication, we have already standardized the powerful genome-wide approach—Repli-seq—to label and capture nascent DNA for high-throughput sequencing and to map temporally ordered replicating DNA in S-phase cells (FIG. 21). We FACS sorted early and late S-phase cells from SupB15 cultures following a short pulse of BrdU labeling. BrdU-labeled DNA from S-phase cells was immunoprecipitated using an anti-BrdU antibody and subjected to next generation sequencing. An early 48 h time point following Hdac1,2 inhibition when cell death was not observed was chosen for the analysis. Our preliminary Repli-seq experiment has identified around 60,000 and 84,000 regions replicating in early or late S-phase SupB15 cells, respectively. Around 17% of these replicating regions showed a shift in their timing (early to late or vice versa) upon Hdac1,2 inhibitor treatment (FIG. 21). We have therefore shown that Hdac1,2 inhibition altered replication timing in Pre-B-ALL cells. This change in replication timing might be due to altered chromatin structure as a result of increased histone acetylation.

We will therefore determine where in the genome is H4K16ac targeted by Hdac1,2 in S-phase cells. We will treat SupB15 cells with either DMSO or the Hdac1,2 inhibitor and perform ChIP-seq to obtain genome-wide occupancy profiles for H4K16ac. For this ChIP-seq, we will use FACS sorted cells similar to that we used for Repli-seq in order to get genome-wide maps that can correlate replicating regions with enriched H4K16ac occupancy. We will also perform ChIP-seq of DNA polymerase a in these cells to obtain a reference point for the location of the fork, and then determine the extent to which H4K16ac around a replication fork is altered upon Hdac1,2 inhibition. To resolve our data, we will use bioinformatics tools (e.g., Useq or IGB, see attached letter) to overlay ChIP-seq and Repli-seq datasets and identify replicating regions where H4K16ac is targeted by Hdac1,2.

Example 18

Does HDAC1,2 Inhibition Trigger DNA Damage at Sites of DNA Replication?

In addition to impeding fork progression, inhibition of Hdac1,2 induced γH2AX foci formation, indicating activation of the DNA damage signaling. The defective chromatin template formed in the absence of Hdac1,2 activities might be the cause for fork stalling and DNA damage. Therefore, we will test whether γH2AX is also present at loci where inhibition of Hdac1,2 caused increased H4K16ac and an 'open' chromatin. To this end, we will perform ChIP-seq to determine genome-wide occupancies of γH2AX in early and late S-phase cells treated with either DMSO or the Hdac1,2 inhibitor.

Example 19

Expected Results from Examples 17 and 18

If defective chromatin structure in the absence of Hdac1,2 activities is the instigator of DNA damage, then we expect γH2AX to be present at and around replication forks with increased H4K16ac. Presence of γH2AX in a non-replicating region would likely be due to impaired DNA repair upon Hdac1,2 inhibition. If DNA breaks upon inhibiting Hdac1,2 occur in late S-phase coincident with heterochromatin replication, then it would explain how HDAC inhibitors induce chromosomal breaks (i.e., genome instability), as DNA breaks in late S-phase would have insufficient time to be repaired and would get 'torn' apart during mitosis.

This information has important implication for cancer therapeutics. For example, if breaks occur in heterochromatin, one could achieve synthetic lethality by combining Hdac1,2 inhibitor with inhibitors of DNMT1 (which is recruited to nascent heterochromatin) in case Hdac1,2 inhibition alone fails to kill cancer cells. Since H4K16ac is enriched at candidate replicating loci and nascent DNA, we anticipate a good correlation between H4K16ac occupancy and replicating regions genome-wide. However, in the unlikely scenario we notice H4K16ac occupancies do not overlap with replicating loci, we will then use ChIP-seq to determine S-phase genome-wide occupancy of H4K91ac, a modification targeted by Hdac1,2 that can also affect nucleosome/chromatin structure (FIGS. 18A and 18C). Overall, completion of our studies will provide us a panoramic view of how Hdac1,2 activities are required to regulate histone acetylation and genome stability during S-phase progression of Pre-B-ALL cells. We have successfully conducted Repli-seq in Pre-B-ALL cells (FIG. 21). We have performed ChIP for H4K16ac in S-phase cells, and have optimized conditions for ChIP in SupB15 cells. We will further confirm our results in two additional Ph+Pre-B-ALL cell lines and primary patient samples using standard ChIP and/or BrdU-IP at target loci selected from our Repli-seq data.

Example 20

Determination of Whether HDAC1,2 Target Histone Acetylation to Modulate Nucleosome Transactions During DNA Replication and Repair in Pre-B-ALL Cells Inhibiting Hdac1,2 activities made nascent mononucleosomes sensitive to MNase digestion in addition to polynucleosomes. This indicated a role for Hdac1,2 in regulating intra-nucleosomal interactions in addition to inter-nucleosomal interactions. We had found H4K91ac, a modification in the nucleosome core, as a target of Hdac1,2 (FIG. 18C). H4K91 influenced nucleosome assembly by regulating interactions between the H3-H4 tetramer core and the H2A-H2B dimers (FIG. 18A). Proper nucleosome assembly was important for fork progression. During DNA replication, parental nucleosomes are disassembled to facilitate fork movement and reassembled after DNA synthesis.

We will examine if nucleosome assembly is affected in the absence of Hdac1,2 function by measuring the kinetics of deposition and removal of H4K91ac at BrdU-labeled nascent DNA over time in Ph+Pre-B-ALL cells using our novel Brdu-ChIP assay. As a control, we will also include known histone deposition marks (H4K5acK12ac). Additionally, we will examine if increase in H4K91ac reduces H2A-H2B deposition by measuring their levels associated with BrdU-labeled nascent DNA.

Figure 22:
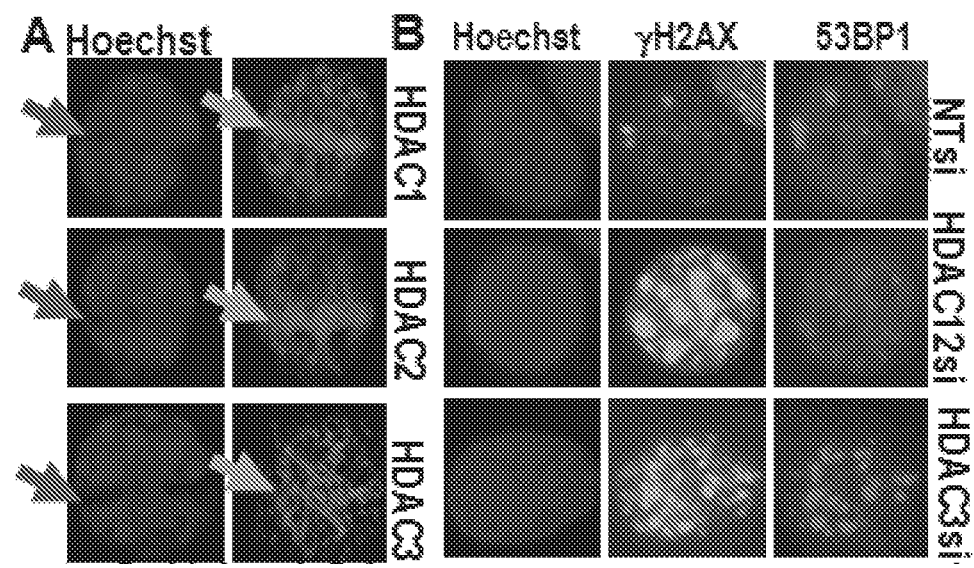
FIG. 22 shows that HDAC1,2 function in DNA repair. siRNA-mediated knockdown of HDAC1,2 or HDAC3 induced DNA damage, as seen by γH2AX foci formation. Loss of HDAC1,2, but not HDAC3, in NIH3T3 cells impaired 53BP1 foci formation. NTsi, non-targeting siRNA (negative control).

The E3 ligase BBAP (B-cell lymphoma & BAL-associated protein) catalyzes H4K91 monoubiquitylation (H4K91ub1) during DNA repair. H4K91ub1 is essential for establishing H4K20 methylation (me), which in turn is involved in the recruitment of 53BP1 (p53-binding protein) to the break sites. 53BP1 is an important factor promoting chromatin dynamics during double-strand break (DSB) repair. Loss or inhibition of Hdac1,2 led to a defective 53BP1 recruitment to break sites (FIG. 22).

To explain this observation, we hypothesize that increased H4K91ac upon Hdac1,2 inhibition blocks H4K91ub1 resulting in reduced H4K20me and impaired 53BP1 recruitment to the break sites. Therefore, our studies allude to the presence of a hitherto unknown '1-14K91 acetyl-ubiquityl switch' at double-strand break sites regulated by Hdac1,2 during DNA repair.

We have optimized laser-mediated DNA break assay in B-cells in the lab and found that Hdac1,2 localized to break sites (FIG. 6D). Using this assay, we will examine if localization of 53BP1, H4K91ac, H4K20me1 and H4K20me2 to laser-induced breaks are altered in Hdac1,2-knockout cells and in Hdac1,2 inhibitor-treated Pre-B-ALL cells. Since an H4K91ub1 specific antibody is not available, we will perform sequential ChIP using antibodies recognizing H4 and ubiquitin to evaluate changes in H4K91ub1 at defined DNA break sites following Hdac1,2 inhibitor treatment. To make defined DNA breaks, we will transfect a plasmid to express I-Ppo1 (a homing endonuclease) in Ph+Pre-B-ALL cells before DMSO or Hdac1,2 inhibitor treatment. I-Ppo1 cleaves at a 15 bp recognition sequence present at multiple sites within the human genome. In addition to H4K91ub1, we will also examine the levels of 53BP1 and other above-mentioned histone marks around specific I-Ppo1 break sites in Ph+PreB-ALL cells using ChIP.

Example 21

Expected Results from Example 20

Without Hdac1,2 activities, we expect defects in nucleosome assembly during the chromatin maturation steps in DNA replication and DNA repair. Given the sensitivity of mononucleosomes to MNase, we anticipate changes in H2A-H2B occupancy relative to H3-H4 occupancy associated with nascent DNA using our BrdU-ChIP approach. In the event, we do not see any change using this bulk nascent chromatin analysis; we will then determine changes in nucleosome assembly at specific candidate replicating loci (e.g., aglobin or selected from our Repli-seq data (Example 18)).

Given the role for H4K91 in DNA repair, we expect Hdac1,2 inhibition to impact nucleosome assembly around break sites. In the unlikely event, we do not see these expected defects in DSB repair, we will examine changes in nucleosome assembly during nucleotide excision repair, where Hdac1,2 played a role as per our pilot studies (data not shown). Related to DNA replication, data from Example 21 to look at H4K91ac on nascent DNA when combined with data for H4K16ac from Examples 18 and 19 will provide us an in-depth view of how Hdac1,2 maintain nascent chromatin structure to regulate replication fork progression.

Example 22

Examine Whether HDAC1,2 Regulate FEN1 Functions in DNA Replication

Figure 19:
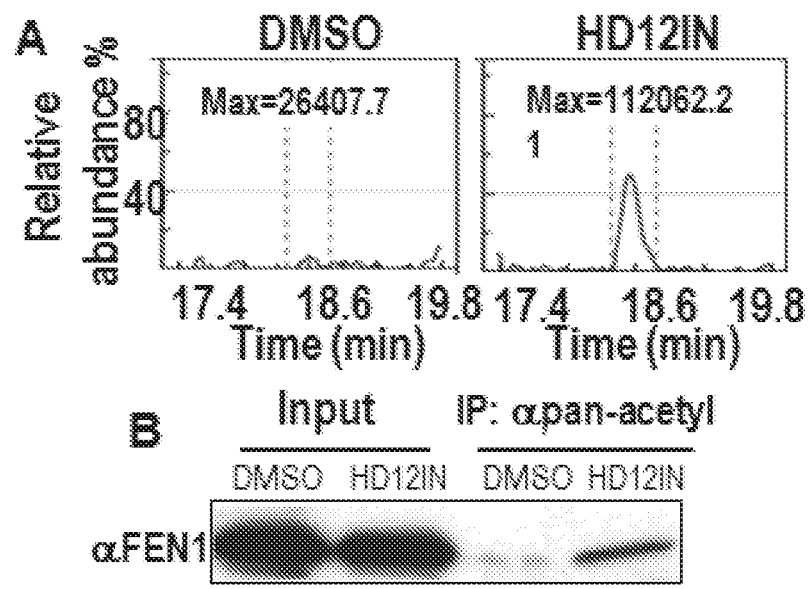
FIG. 19 shows FEN1 was a non-histone target of HDAC1, 2. (A). Extracted ion chromatogram of peptide TGAAGK [Ac]FK (m/z 411.230) attributed to protein FEN1_HUMAN. Chromatograms showed increased abundance of this peptide in samples treated with HDAC1,2 inhibitor (HD12IN). (B). Pre-B-ALL SupB15 cells were treated with DMSO or ACY1035 for 24 h before lysate preparation for immunoprecipitation (IP) using an antibody recognizing pan-acetyl lysine. FEN1 present in the immunoprecipitate was detected using αFEN1 antibody.

Mass spectrometry revealed FEN1 (Flap endonuclease 1), a nuclease involved in DNA replication and replication-stress induced repair (FIG. 23), as a target of Hdac1,2 (FIG. 19). WRN interacts with FEN1 to remove DNA intermediates formed during replication stress. Acetylation-mimetic mutation in K375 of FEN1 disrupts its binding to WRN. We therefore hypothesize that inhibition of Hdac1,2 impairs FEN1 repair activity during replication stress, and makes it unresponsive to the increased WRN helicase activity stimulated by the oncogenic BCR-ABL (FIG. 16). We will examine whether Hdac1,2 inhibition impairs FEN1 functions during DNA replication (Example 23) and in replication stress-induced repair (Example 24) in Pre-B-ALL cells.

FEN1 acetylation decreases its DNA binding affinity in vitro. Therefore, we will use our modified BrdU-ChIP assay to determine whether inhibiting Hdac1,2 affects FEN1 levels on newly synthesized DNA in vivo. To test whether Hdac1,2 regulate the nuclease activity of FEN1 during Okazaki fragment maturation, we will use BrdU pulse-chase combined with comet assays. Briefly, to measure defects in Okazaki fragment maturation, the amount of BrdU-stained DNA in the 'tail' versus the comet head in control and Hdac1,2 inhibitor-treated cells will be measured following gel electrophoresis. As Okazaki fragments mature, the amount of BrdU-labeled DNA in the comet 'tail' will decrease over the period of BrdU-chase.

FEN1 interacts with 34 different proteins involved in various aspects of DNA metabolism, and many of these interactions occur at the C-terminal region of FEN1. Consistent with its role in Okazaki fragment maturation, FEN1 interacts with DNA polymerase δ, RPA (the single-strand DNA binding protein) and DNA ligase 1. We will test if acetylation targeted by Hdac1,2 plays any role in regulating FEN1 interaction with these proteins involved in DNA replication/Okazaki fragment maturation using co-IPs following Hdac1,2 inhibitor treatment of Ph+Pre-B-ALL cells. To directly test the effect of FEN1 acetylation on its nuclease activity and DNA binding affinity in vitro, we will use recombinant FEN1 site-specifically acetylated at K375. This involves expressing acetyl-lysyl-tRNA synthetase and the cognate tRNACUA in bacterial cells, which will direct the incorporation of Nc-acetyl-lysine in response to an amber codon (TAG) introduced for residue 375 of FEN1.

Example 23

Examine Whether HDAC1,2 Regulate FEN1 Functions during Replication Stress Repair Inhibiting Hdac1,2 activities during hydroxyurea-induced replication fork arrest increases the formation of collapsed forks, which suggests a role for Hdac1,2 in DNA repair and/or restart of stalled forks following replication stress. Stalled replication forks can be converted into a four-way structure resembling a Holliday junction. In response to replication arrest, FEN1 interacts with WRN to form a complex. WRN stimulates FEN1 nuclease activity to process aberrant DNA replication intermediates formed during replication stress in order to enable repair and fork restart. WRN interacts with the C-terminal region of FEN1 and mutating the K375 residue in FEN1 to alanine severely disrupted its interaction with WRN. Changing lysine to alanine causes charge neutralization similar to acetylation of a lysine residue.

To test whether Hdac1,2 regulate FEN1-WRN interaction during replication stress, we will use co-IPs to determine changes in their interaction in the presence of Hdac1,2-selective inhibitor upon hydroxyurea-induced replication stress in Pre-B-ALL cells. WRN helicase activity at the Holliday junction intermediate will provide a free 5'ssDNA to be cleaved by FEN1 (FIGS. 23A and 23B). To determine whether Hdac1,2 activities regulate FEN1 activity to resolve recombination intermediates arising from fork stalling, we will perform Holliday junction cleavage assays. We will incubate double-flap DNA substrates with nuclear extracts containing FEN1 prepared from control and Hdac1,2 inhibitor-treated or Hdac1,2-knockout cells. We will resolve the products on a 20% polyacrylamide gel to look at the cleaved flap substrates as described 52. We will also use nuclear extracts from FEN1 depleted cells as a control in these assays.

Our preliminary results showed that mutations in FEN1 K375 residue caused DNA damage in SupB15 cells (FIG. 23C). Hdac1,2 inhibition decreased homologous recombination (HR) in a BCR-ABL transformed cell line (FIG. 23D) containing a stably integrated DR-GFP reporter with an I-Sce1 site. We will examine the effect of FEN1 K375 mutants (K75A/K375R/K375Q) on HR in these BCR-ABL transformed reporter cell line. We will also examine the effect of FEN1 K375 mutations on the viability of SupB15 cells using FEN1 shRNA-mediated knockdown/complementation approach as described above. We will test whether Hdac1,2 inhibition affects the interaction of BCR-ABL with WRN and the ability of BCR-ABL in phosphorylating and nuclear-targeting of WRN using co-IP and cell fractionation, respectively.

Example 24

Expected Results from Examples 22 and 23

Since the C-terminal region of FEN1 is important for its functions, we anticipate defects in Okazaki fragment maturation following Hdac1,2 inhibition. If Okazaki fragment maturation is not defective, then our parallel studies to test whether acetylation affects FEN1 interactions with replication-associated proteins will uncover how Hdac1,2 might regulate FEN1 functions during replication. Since FEN1K375 mutants caused DNA damage (FIG. 23C), we anticipate these mutants to impair HR repair and also compromise viability in SupB15 cells. We expect Hdac1,2 inhibition to reduce/abolish interaction with WRN under replication stress. Thus, we will be able to determine how Hdac1,2 regulate FEN1 functions during replicative-stress repair.

If Hdac1,2 inhibition does not affect the interaction or activity of BCR-ABL towards WRN, then it will support our possibility that Hdacs1,2 work primarily by affecting the overall functions of WRN and FEN1. If however Hdac1,2 inhibition disrupts the interaction or activity of BCR-ABL on WRN, then we will test whether these two proteins are direct targets of Hdacs1,2. Overall, successful completion of studies described in Examples 23 and 24 would for show the direct functions for Hdac1,2 in the DNA repair steps after replication stress via targeting FEN1 acetylation and delineate the precise mechanism by which Hdac1,2 inhibition causes genotoxic stress in Pre-B-ALL cells.

Example 25

Figure 24:
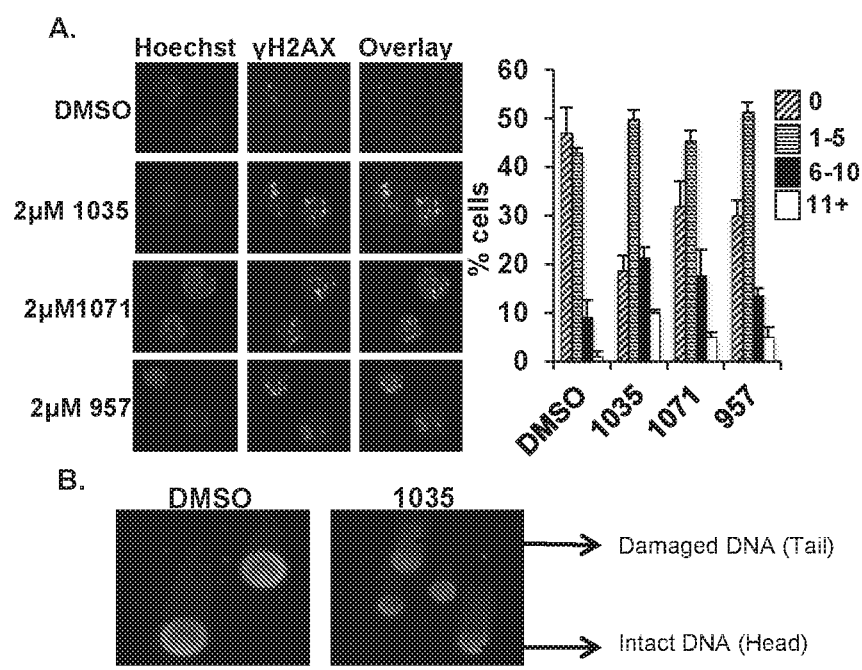
FIG. 24 shows DNA damage activation in Ph+PreB-ALL cells. SupB15 cells were treated with 2 µM ACY1035, ACY1071, ACY957, or solvent (DMSO) for 48 hours. (A) Immunofluorescence with γH2AX was performed on treated SupB15 cells. The number of γH2AX foci was counted in around 100 cells for each treatment and classified into cells with no foci, 1-5, 6-10, and greater than 10 foci. (B) SupB15 cells treated with DMSO or ACY1035 for 48 hours were tested via neutral comet assay to measure the amount of double-strand breaks (DSBs), indicated by the tail.

Inhibition of HDAC1,2 Impairs Double-Strand Break Repair and Activates DNA Damage in Ph+Pre-B-ALL Cells BCR-ABL promotes DNA repair to prevent DNA damage accumulation in Philadelphia chromosome-positive (Ph+) leukemia cells. To examine the effect of various HDAC1, 2-selective inhibitors on DNA repair and DNA damage response in Pre-B-ALL cells that express BCR-ABL, SupB15 (Ph+PreB-ALL) cells were treated with 2 µM ACY1035 or 2 µM ACY1071 or 2 µM ACY957 for 48 hours. A dramatic increase in DNA damage response was observed in SupB15 cells upon HDAC1,2 inhibitor treatment (FIG. 24A). Quantitation of γH2AX foci, a marker of double-strand breaks, showed a statistically significant increase in DNA damage following ACY957 or ACY1035 or ACY1071 treatments.

We next asked whether double-strand break repair is impaired in SupB15 cells. We used neutral comet assays to measure the efficiency of double-strand break repair following treatment with ACY1035 for 48 hours. The neutral comet assay specifically measures double-strand breaks and not single-strand breaks. In this assay, control and HDAC1,2 inhibitor treated SupB15 cells were embedded in low melting agarose and subjected to electrophoresis to separate damaged DNA from intact DNA. Damaged DNA runs faster and therefore forms a tail, and the intact DNA is present in the head (FIG. 24B). DNA was visualized with sybrgreen staining. In this repair assay, an increase in damaged DNA was observed following ACY1035 treatment of SupB15 cells (FIG. 1B). We observed similar results with ACY1071 and ACY957. Hence, these results again confirms that HDAC1,2 inhibition impairs double-strand break repair and results in accumulation of broken DNA in Ph+Pre-B-ALL cells.

Example 26

High-Throughput Quantitative Mass Spectrometry Analysis Identified Key Double-Strand Break Repair Pathways Affected Upon HDAC1,2 Inhibition As disclosed herein, HDAC1,2 impairs of DNA repair via FEN1 acetylation.

Figure 25:
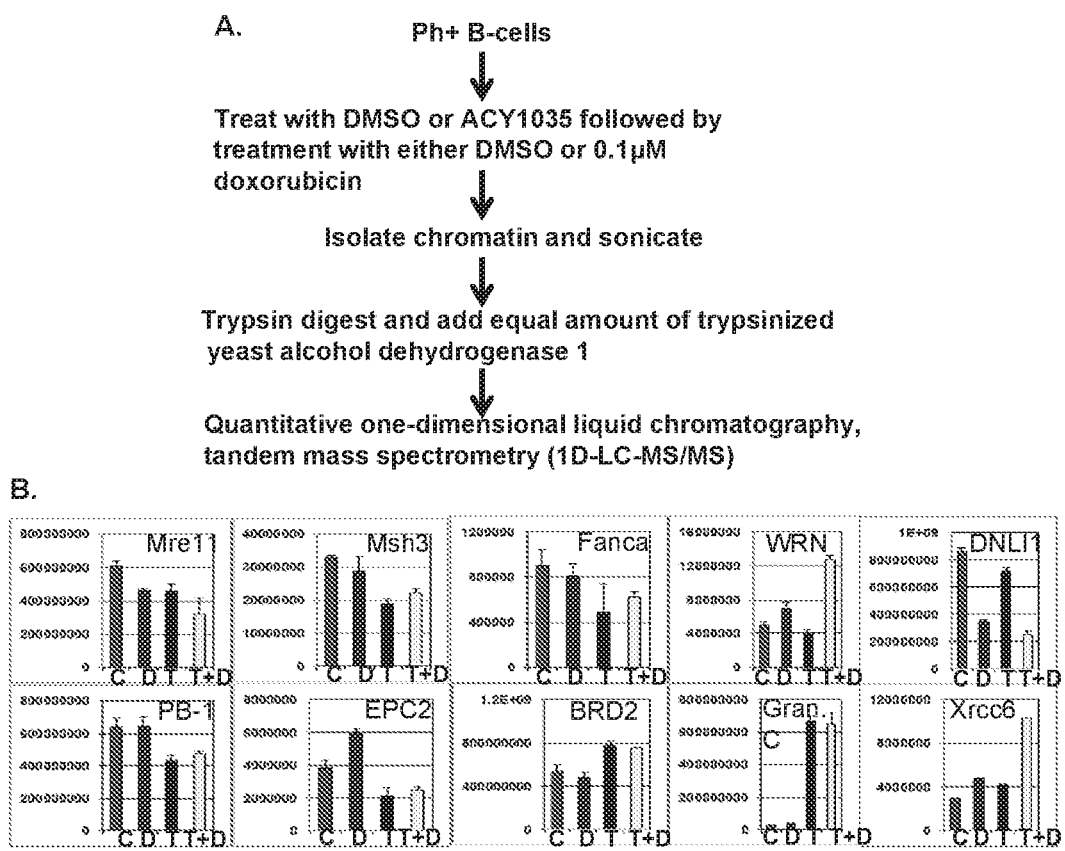
FIG. 25 shows mass spectrometry analysis in Ph+BCR-ABL expressing cells following treatment with doxorubicin, HDAC1,2 inhibitor, or doxorubicin plus HDAC1,2 inhibitor. (A) Schematic diagram of quantitative one-dimensional liquid chromatography and tandem mass spectrometry (1D-LC-MS/MS) analysis in BCR-ABL containing cells following ACY1035 treatment for 48 hours or 0.1 µM doxorubicin for 10 hours or ACY1035+doxorubicin for 36 hours+10 hours. Proteins that showed a differential binding to chromatin were filtered following an ANOVA test across all the four treatment groups. An ANOVA value of 0.01 or less than 0.01 cut-off was used to filter statistically significant proteins. Using the Panther software, molecular function of proteins with at least a 1.3-fold decrease in the chromatin-binding was determined. (B) Average peptide counts from obtained from mass spectrometry analysis with three independent chromatin isolates and three independent treatments. Yeast chromatin was used as the spike-in control for normalization. C refers to DMSO control, D refers to doxorubicin treatment, T refers to ACY1035 treatment; and T+D refers to ACY1035 plus doxorubicin treatment.

Experiments were performed to determine whether inhibition of HDAC1,2 affects other DNA repair and replication proteins in Pre-B-ALL cells expressing BCR-ABL. To examine changes in chromatin binding of nuclear proteins that are involved in repair and replication, a large-scale quantitative LC-MS/MS (1D-LC/MS-MS) proteomic screen was performed in BAF3/BCR-ABL cells following treatment with DMSO; HDAC1,2 inhibitor; doxorubicin; or HDAC1,2 inhibitor plus doxorubicin (FIG. 25A). A time point where only DNA damage but no cell death was activated was chosen for this analysis. There was a ≥1.5-fold decrease or increase in the chromatin-bound levels of ~150 nuclear proteins following HDAC1,2 inhibition. Proteins that had an ANOVA test value of 0.01 or less than 0.01 across all four treatment groups were analyzed. No change in chromatin-bound SMARCA5 chromatin remodeler was observed following HDAC1,2 inhibition.

Figure 26:
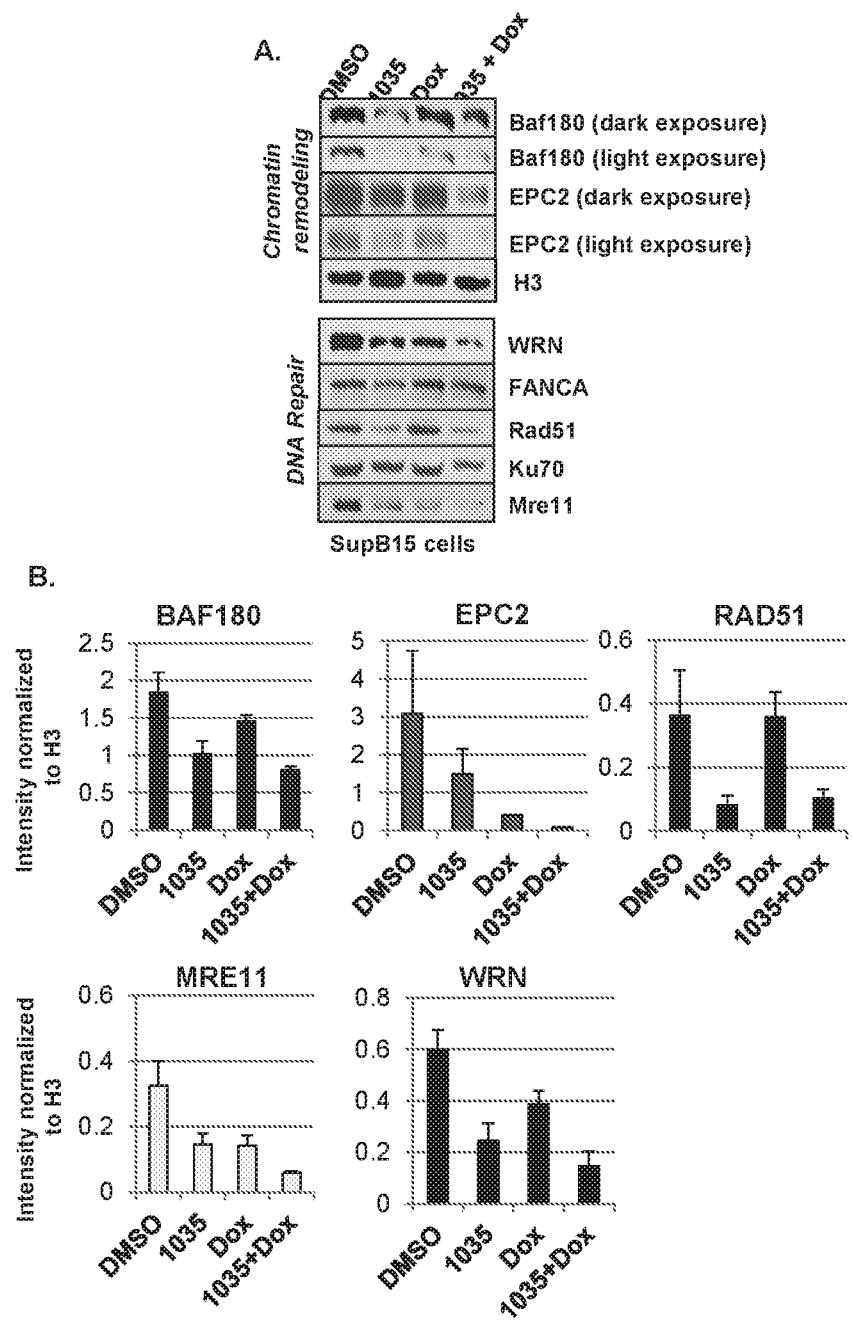
FIG. 26 shows validation of data obtained from mass spectrometry analysis using western blot analysis. (A) Western blots targeting various proteins were performed with at least five independent isolates of chromatin from cells treated with solvent (DMSO), HDAC1,2 inhibitor ACY1035 (1035), doxorubicin (Dox), or doxorubicin plus ACY1035 (1035+Dox). (B) Quantitation of the western blot signal for various repair proteins after normalization to total H3.

Several proteins obtained from mass spectrometry analysis were further validated by western blot analysis. A decrease in chromatin-bound levels of double-strand break repair proteins (Mre11, Rad50, Rad51, WRN, FANCA, and DNA Ligase I (DNLI1)) was observed (FIGS. 25B, 26A and 26B). In addition to proteins that are directly involved in the double-strand break repair pathway, a decrease was observed in the levels of chromatin remodelers, BAF180 and EPC2, following HDAC1,2 inhibition. BAF180 is a subunit of PBAF SWI/SNF family chromatin remodeler complex and localizes to double-strand breaks, where it promotes transcriptional silencing during DNA repair via H2AK119 monoubiquitylation (H2AK119ub1, another transcriptional repression marker).

Figure 27:
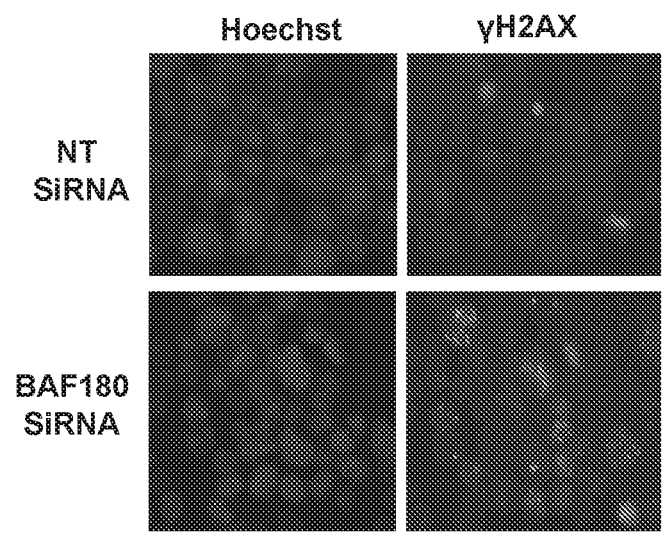
FIG. 27 shows that BAF180 knockdown leads to increased DNA damage in cells expressing BCR-ABL. HAP1 adherent cells that contain the BCR-ABL translocation were transfected with either non-targeting or BAF180 siRNA pool and immunofluorescence for γH2AX was performed at 72 hours post-siRNA transfection. Increased DNA damage is seen in BAF180 knockdown cells when compared to the control non-targeting siRNA knockdown cells.
Figure 28:
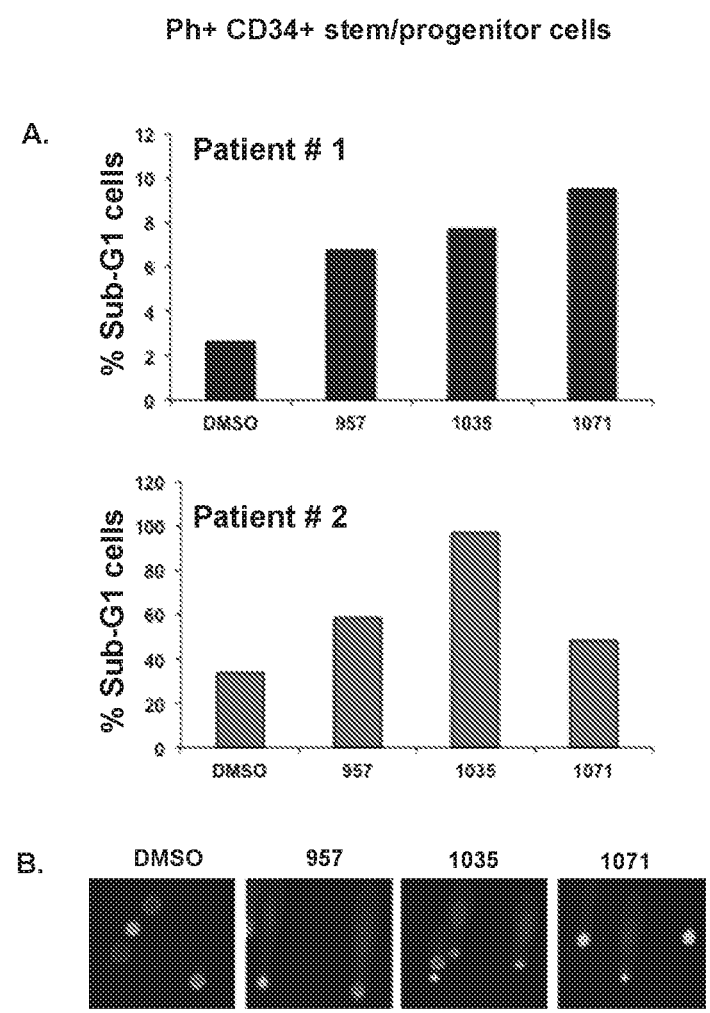
FIG. 28 shows that HDAC1,2-selective inhibitors cause cytotoxic or cytostatic effects and impair DNA repair in Ph+ CD34+ stem/progenitor cells. (A) FACS analysis of propidium iodide stained-cells following treatment of cells with solvent (DMSO, ACY957, ACY1035, or ACY1071, showing the percentage of cells determined to be in the SubG1 stage following each treatment. (B) Neutral comet assays show increased DNA damage and decreased DNA repair in Ph+ CD34+ cells upon HDAC1,2 inhibitor treatment. Comet analysis was performed with two different Ph+ALL CD34+ samples and representative pictures from one experiment are shown.

Experiments also demonstrated an increase in DNA damage following BAF180 knockdown in cells expressing BCR-ABL (FIG. 27). Inhibition of BAF180 activity results in an activation of DNA damage response, so a decrease in chromatin-bound BAF180 following HDAC1,2 inhibition is one of the mechanisms by which DNA damage is activated in these cells. A reduction in chromatin-bound enhancer of polycomb repression complex 2 (EPC2) was observed following HDAC1,2 inhibitor treatment (FIGS. 26A and 26B). EPC2 is a component of p400 chromatin remodeler complex and is also involved in DNA damage response and DNA repair. EPC2 is required for sustained oncogenic potential of leukemia stem cells, and a decrease in EPC2 can result in activation of DNA damage response in leukemia stem cells. Treatment with HDAC1, 2 inhibitors led to cytoxic or cytostatic effects and impaired DNA repair in CD34+ Ph+ALL stem/progenitor cells (FIG. 28).

Example 27

Inhibition of HDAC1,2 in Combination with Low Doses of Doxorubicin Massively Affects DNA Replication Processes Doxorubicin can be used to treat leukemias in addition to lymphomas. Doxorubicin is a DNA intercalating agent that impairs DNA repair. Doxorubicin inhibits the process of DNA replication and activates the DNA damage response in cancer cells. Experiments were conducted to determine what chromatin-bound proteins are affected upon treatment of BCR-ABL containing cells with ACY1035 in the presence of low doses of doxorubicin. For the mass spectrometry analysis, BAF3/BCR-ABL cells were treated with 2 µM ACY1035 for 48 hours. Doxorubicin at a final concentration of 0.1 µM was added during the last 10 hours of treatment.

The majority of chromatin-bound proteins that decreased following ACY1035 plus doxorubicin treatment compared to ACY1035 treatment alone belong to DNA replication and DNA replication-associated repair processes (FIGS. 29A and 29B). These results provide the precise mechanism by which doxorubicin impairs DNA replication in cancer cells. In concordance with defective S-phase associated DNA repair pathways identified in our mass spec analysis, BrdU ChIP assays revealed an increase in γH2AX on the nascent chromatin in SupB15 cells following ACY1035 treatment.

Example 28

Figure 30:
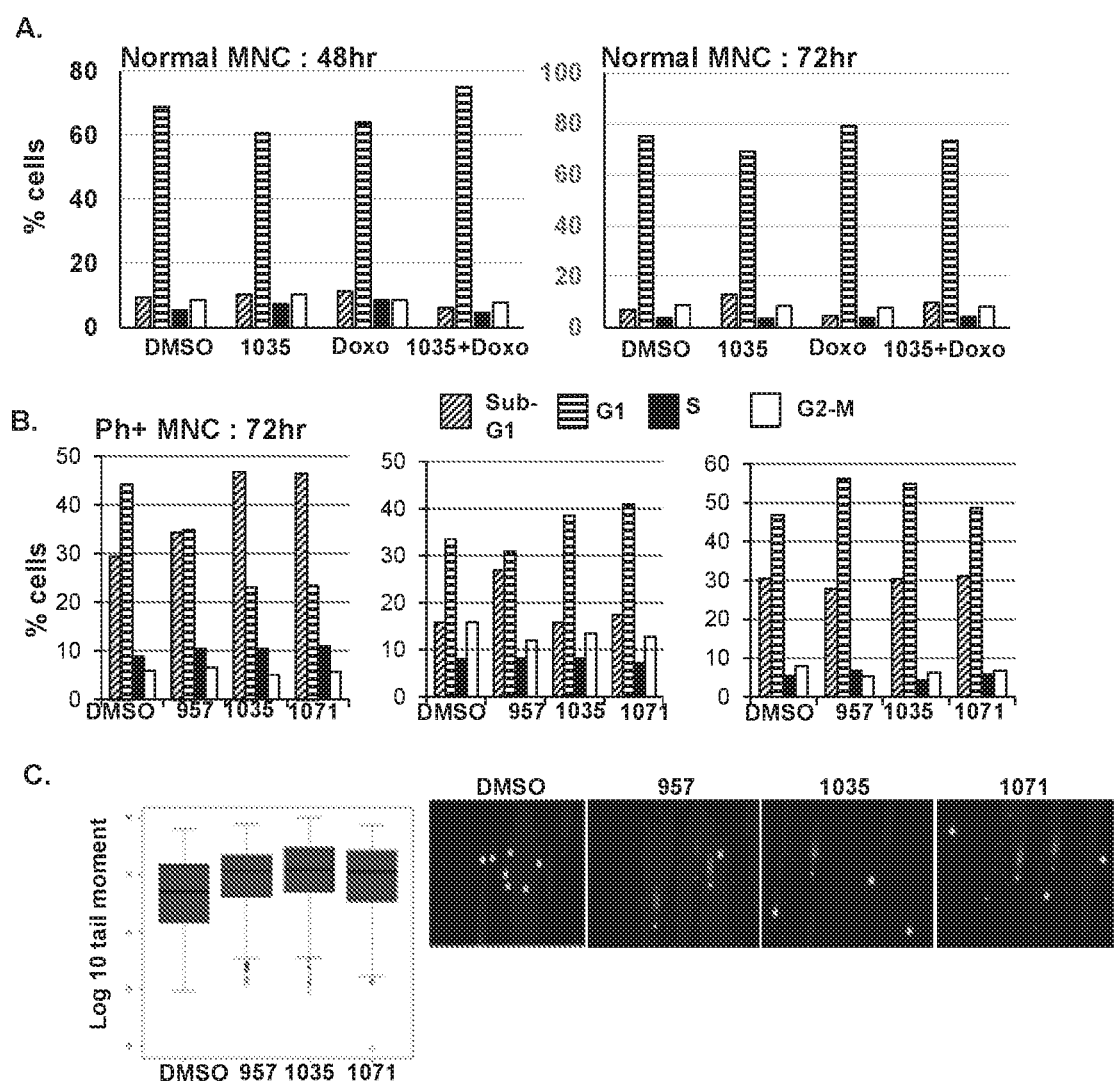
FIG. 30 shows that (A) HDAC1,2-selective inhibitors cause no cytotoxic or cytostatic effects normal mononuclear cells (MNC) but (B) do cause cytotoxic or cytostatic effects in Ph+ mononuclear cells. (C) Neutral comet assay shows increased DNA damage and decreased DNA repair in Ph+ MNC upon HDAC1,2 inhibitor treatment for 48 hours. Comet analysis was performed with four different Ph+ALL patient samples and the cumulative tail moment from this analysis is shown, along with representative comet assay images.

HDAC1,2 Inhibition has Cytotoxic/Cytostatic Effects on Primary Ph+PreB-ALL Mononuclear and Stem/Progenitor Cells Inhibition of HDAC1,2 triggers death in Ph+Pre-B-ALL cell lines. In order to test the efficacy of HDAC1,2 inhibitor in primary Ph+ALL patient samples, primary Ph+ALL mononuclear cells (MNC) were cultured and cell cycle analysis was performed following a 72-hour treatment with HDAC1,2 inhibitors. Normal mononuclear cells served as a negative control. In this analysis, either a G1 arrest or an increase in sub-G1 population was observed following treatment of Ph+MNCs with HDAC1,2 inhibitors, and normal mononuclear cells were unaffected by treatment with HDAC1,2 inhibitors (FIGS. 30A and 30B). Neutral comet assays revealed an increase in damaged DNA in these primary patient samples following HDAC1,2 inhibition (FIGS. 30C, 30D).

As disclosed herein, chromatin-bound EPC2 (the chromatin remodeler that promotes leukemia stem cell potential) decreased upon HDAC1,2 inhibition. Experiments were conducted to determine whether HDAC1,2 inhibitors are effective against Ph+ALL stem/progenitor cells. Stem/progenitor cells were FACS-sorted using human CD34 stem/progenitor cell surface marker and used for propidium-iodide cell cycle analysis as well as comet assays. A G1 arrest or an increase in subG1 (dead) population was observed in Ph+ALL CD34+ cells following HDAC1,2 inhibition (FIG. 28A). Since the majority of CD34+ stem/progenitor cells are quiescent, no significant population of S-phase cells was detected (FIG. 28A). An increase in the damaged DNA was also observed in comet assays following HDAC1,2 inhibition, suggesting that non-homologous recombination repair pathway used by quiescent stem cells is also affected upon HDAC1,2 inhibition (FIG. 28B). HDAC1,2 inhibitors are very potent in primary patient samples.

Example 29

Selective HDAC1,2 Inhibition is an Effective Therapeutic for Ph+Pre-B-ALL

Figure 32:
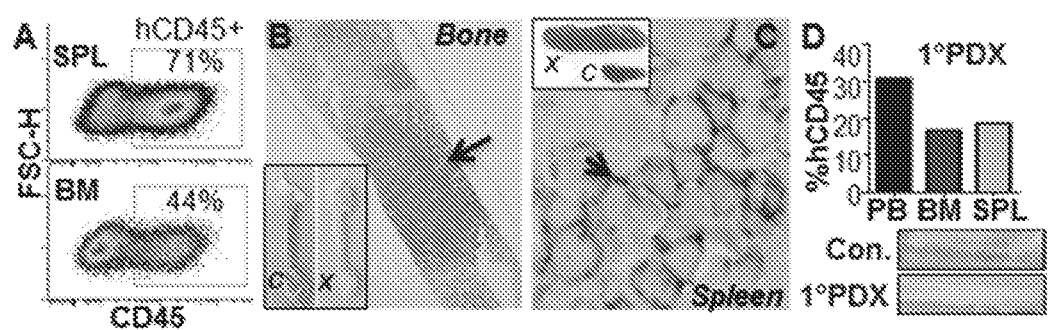
FIG. 32 shows in (A). FACS profiles for human (h) CD45 B-cell marker in spleen (SPL) and bone marrow (BM) 5-wk post SupB15 cell engraftment into NSG mice. (B). Representative TdT staining of a bone cross-section from a Supb15 xenograft showing patchy leukemic infiltrate in the bone marrow (arrow). Inset showed normal bone from a control mouse (c) and pale bone from a xenograft (x) mouse. (C). CD19 immunohistochemistry showing membrane positivity in leukemia cells with negative signal in adjacent normal spleen cells in a SupB15 xenograft. Inset showed normal spleen from a control mouse and an enlarged spleen from a xenograft mouse. (D). FACS data for human (h) CD45 cells in peripheral blood (PB), bone marrow (BM) and spleen (SPL) from a primary patient-derived xenograft mouse (1° PDX). Analysis was done 4-wk post engraftment of Ph+CD34+ leukemic cells from a newly-diagnosed patient into NSG mouse. Normal bone from a control mouse (Con.) and pale bone from a primary PDX mouse were shown.

Disclosed herein are methods for using and use of HDAC1,2 selective inhibitors to treat the hyperactive repair addicted BCR-ABL expressing Ph+Pre-B-ALL cells in the clinic. Pre-B-ALL cell lines as well as Ph+ALL primary patient samples were engrafted in NOD scid gamma (NSG) mice to examine the efficacy of Hdac1,2 inhibitor in killing cells in vivo. We injected NSG mice with SupB15 cells ($1 \times 10^6$) and Ph+Pre-B-ALL primary patient cells and monitored engraftment by flow cytometry using anti-human CD45/CD19 antibodies every week for 4-5 weeks. We saw successful engraftment with SupB15 and primary Ph+Pre-B-ALL cells (FIG. 32). FACS analysis showed human CD45+ cells in bone marrow and spleen of xenografts (FIG. 32A). Similar results were obtained with human CD19 antibody in combination with CD45 or in isolation (data not shown). To examine the extent of leukemia infiltration in spleen and bone marrow, we performed IHC analysis. Human TdT (a B-cell marker highly expressed in Pre-B-ALL patients) staining showed leukemia infiltration in bone marrow (FIG. 32B) and in spleen of xenograft mice (data not shown). We also observed human CD19 surface staining by IHC (FIG. 32C). Pale bones and enlarged spleen indicative of a diseased state were seen in SupB15 xenograft mouse (insets in FIGS. 29B and 29C). Successful engraftment of primary patient Ph+ PreB-ALL cells in NSG mice was also achieved, as we detected human CD45+ cells in peripheral blood, bone marrow and spleen of patient-derived xenograft (PDX) mice (FIG. 32D).

Additional experiments were performed to assess the therapeutic benefits of HDAC1,2 inhibition in vivo using primary Ph+ALL patient derived xenograft mouse models. NOD/SCID mice were irradiated with a sub lethal dose of irradiation to ablate the immune system in these mice. Immune-compromised NSG mice were then injected with $2 \times 10^6$ CD34+ cells isolated from a Ph+ ALL patient. Bone and spleens were harvested from these primary xenograft mice when the leukemia burden reached the maximum 90-95% level as determined by FACS analysis for human CD19 and CD45 markers. Cells isolated from bone marrow and spleen of these primary xenograft mice were frozen in liquid nitrogen until use. A mixture of bone marrow and spleen cells from the primary xenograft mice was then injected into a cohort of sub-lethally irradiated NOD/SCID mice. Mice were divided into four treatment groups: solvent, ACY1035, doxorubicin, and ACY1035 plus doxorubicin. Xenograft mice were injected according to one of the four treatment groups after 5 days post-xenograft induction, when human CD45 marker reached around 5-10% in the peripheral blood. Mice were injected with 25 mg/kg ACY1035 every other day via i.p. and 0.25 mg/kg doxorubicin once a week via i.v., a dosing schedule that has minimal toxicity in immune compromised mice.

Figure 31:
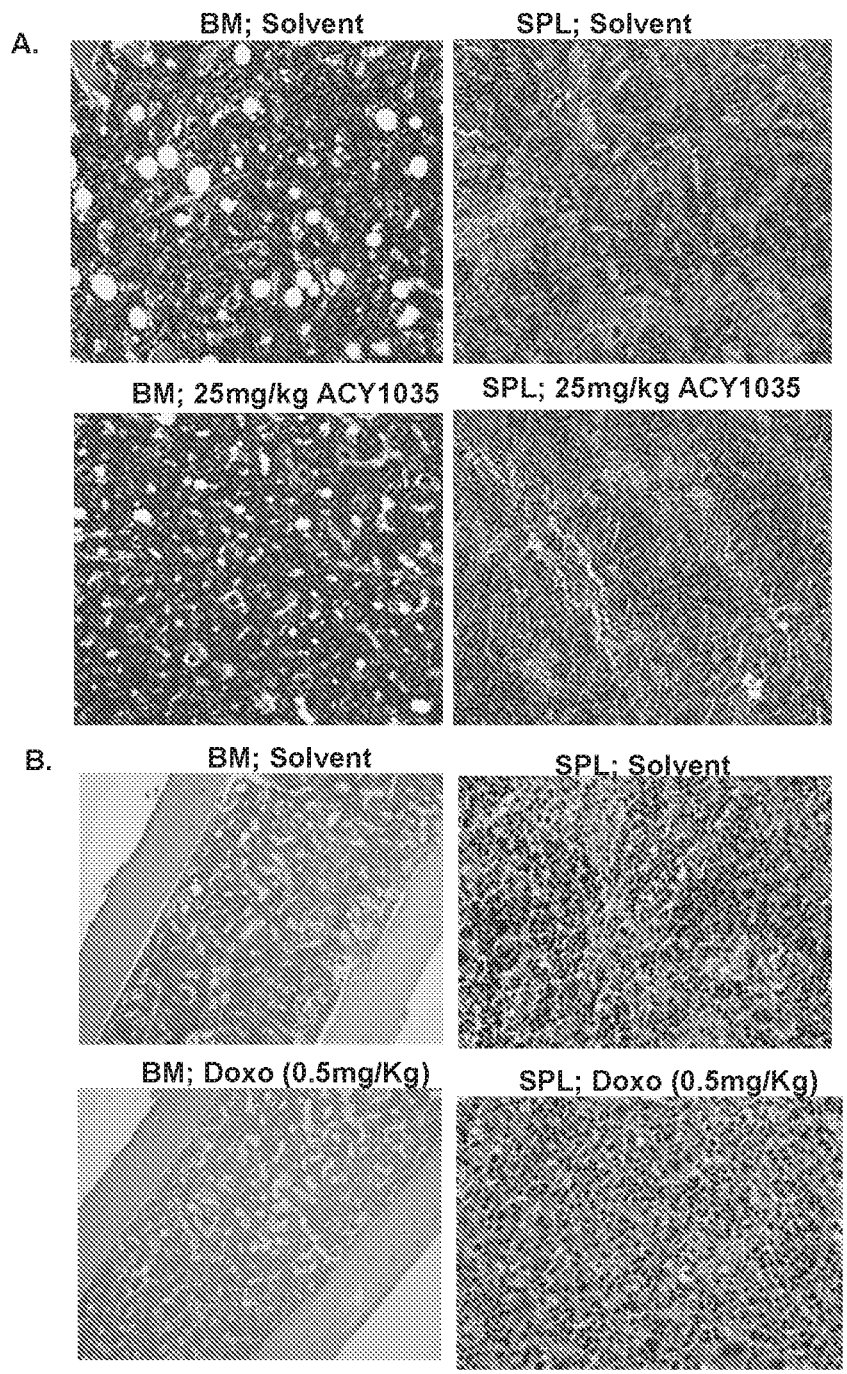
FIG. 31 shows hematoxylin and eosin staining of bone marrow (BM) and spleen (SPL) sections from normal NOD-SCID-Gamma mice injected with solvent, 25 mg/kg ACY1035 (fifteen doses), or 0.5 mg/kg doxorubicin (six doses). These tests showed no abnormalities or changes in the cell morphology in bone marrow or spleens of mice after ACY1035 or doxorubicin administration. ACY1035 does not have toxic effects in vivo.

No changes in the morphology of spleen or bone marrow cells were observed at the doses of ACY1035 used (FIG. 31A) or even at 0.5 mg/kg doxorubicin which is the twice the concentration used in the present study (FIG. 31B). Moreover, no cardiac toxicity was observed upon HDAC1,2 inhibitor treatment even after 21 doses. Hence, HDAC1,2 inhibition can potentially overcome the cardiac toxicity observed in patients upon treatment with the broad spectrum pan HDAC inhibitors.

Figure 33:
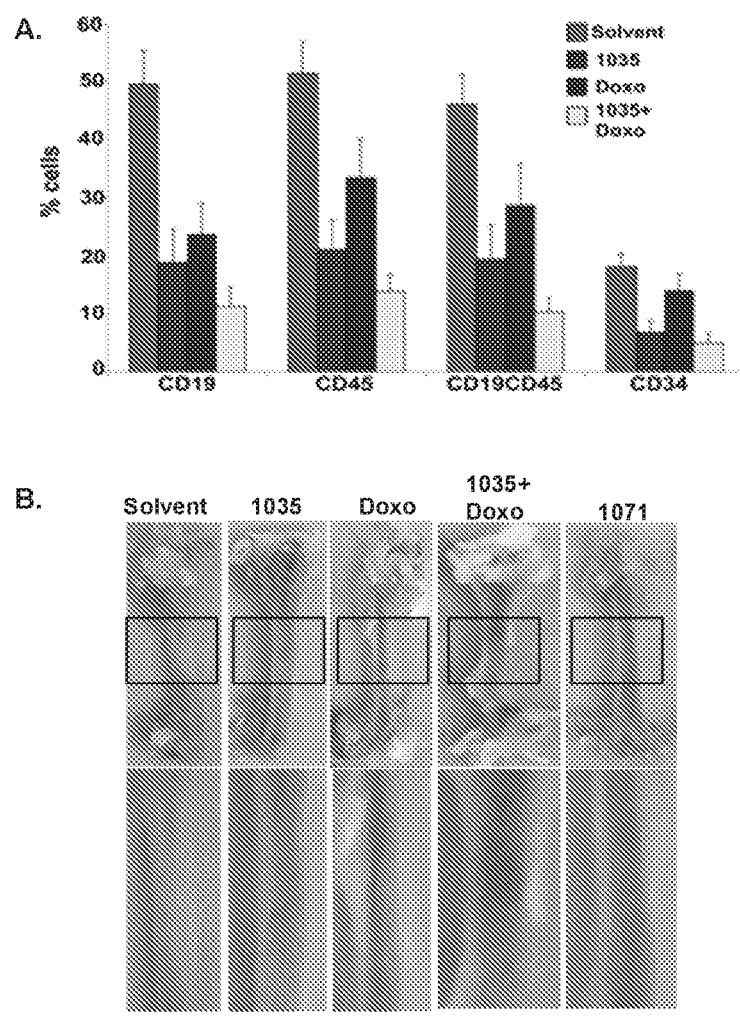
FIG. 33 shows that HDAC1,2 inhibition has therapeutic benefits in a Ph+ALL patient-derived xenograft mouse model. Patient-derived xenograft mice were treated with either cyclodextrin (solvent) or 25 mg/kg ACY1035 every other day for a total of 21 doses. (A) The level of human CD19, CD45, and CD34 markers were assessed in the bone marrow of these mice by FACS analysis. For each FACS marker, the bars represent (from left to right): solvent, ACY1035, doxorubicin, ACY1035+doxorubicin. (B) Solvent-treated mice have bones infiltrated with white blood cells.

Analysis of bone marrow and spleen cells by FACS analysis showed a significant reduction in the human CD45 and CD19 markers in bone marrow of ACY1035, doxorubicin, and ACY1035 plus doxorubicin-treated PDX mice when compared to the solvent-treated mice (FIG. 33A). In this PDX model, the majority of leukemia cells homed in the bone marrow and not spleen. Surprisingly, ACY1035-treated mice exhibited greater decrease in the human leukemia markers when compared to doxorubicin-treated mice. Similar results were observed with ACY1071 treatment in vivo. Furthermore, a decrease in human CD34+ stem/progenitor cells was observed similar to the results obtained from in vitro studies (FIG. 33A). A decrease in the white cell burden was visually seen in PDX mice treated with ACY1035, doxorubicin, or ACY1035 plus doxorubicin compared to the solvent-treated mice (FIG. 33B). The disclosed mechanistic and preclinical results provide strong evidence that HDAC1,2 inhibition or HDAC1,2 inhibition in combination with doxorubicin can provide a very potent therapeutic for Ph+PreB-ALL.

Example 30

In Vivo Hdac1,2 Inhibition in Pre-B-ALL Using a Mouse Model of BCR-ABL/B-ALL

The effect of Hdac1,2 inhibition on Pre-B-ALL will be further investigated in vivo using an induced mouse model of BCR-ABL/B-ALL. Pre-B-ALL will be induced by injecting BALB/c bone marrow cells ($1 \times 10^6$) retrovirally transduced with a vector for co-expression of BCR-ABL and a GFP marker into lethally irradiated recipients. These mice develop leukemia in 1-2 weeks and start to die by 3-4 weeks. If needed, survival will be increased to perform analyses in a longer time window by injecting fewer cells. To monitor BCR-ABL containing cells, GFP+B220+ cells will be measured in peripheral blood at 3-days interval after 10 days following retroviral transduction. Heska HemaTrue blood cell counter will be used to measure blood counts, and FACS will be used to measure GFP+ cells to diagnose the onset of leukemia.

Intraperitoneal (IP) injections with DMSO or Hdac1,2 inhibitor will occur when GFP+B220+ cells reach 1% of total white blood cells, and animals will be monitored to determine if leukemia is reversed over time. The percentage of GFP+B220+ cells in the peripheral blood will also be monitored to track leukemia regression following Hdac1,2 inhibitor treatment, for example, treatment with ACY1035.

We expect a decrease in GFP+B220+ cells in the peripheral blood with ACY1035 treatment within 1-2 weeks following treatment. We will use enhanced survival and decrease in GFP+white blood cells as our endpoint analysis. Diseased mice will be subjected to histopathological analysis to examine spleen, liver, bone marrow and any other macroscopically involved organs. Immunohistochemistry (IHC) analysis with leukemia markers will also be performed.

Example 31

Figure 34:
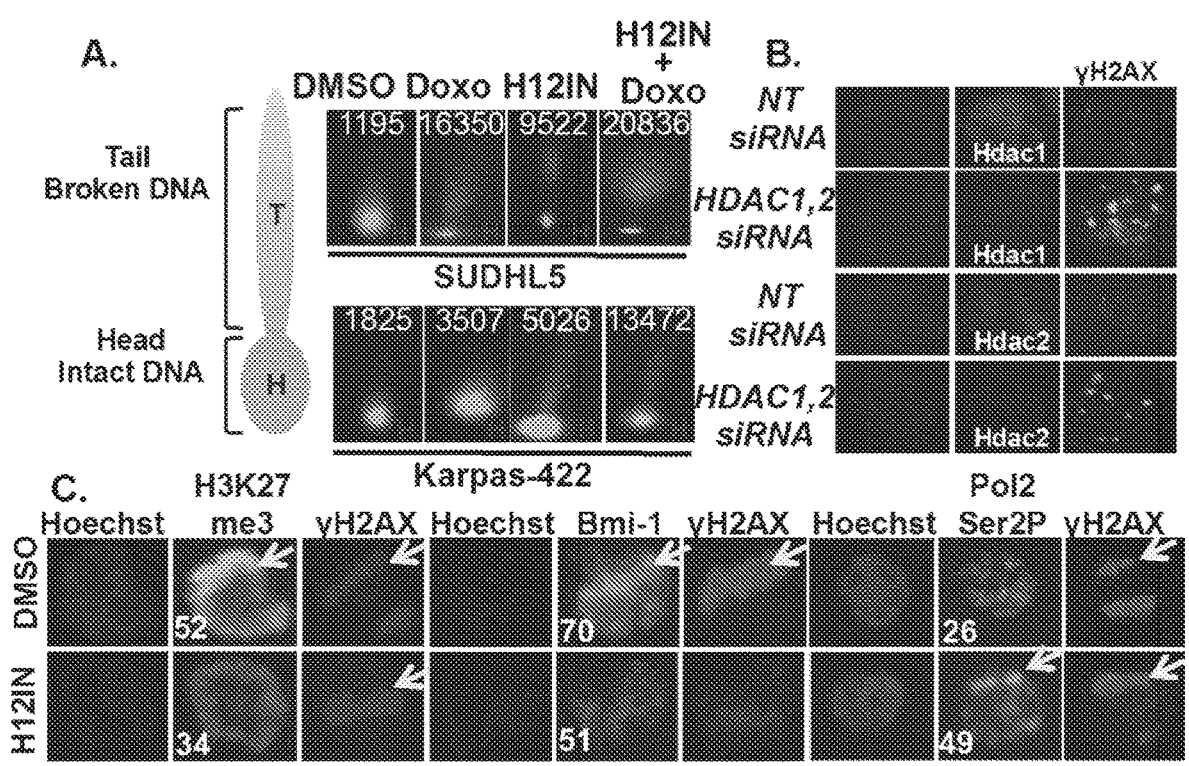
FIG. 34 shows that HDAC1, 2 inhibition affects DNA repair and induces DNA damage in EZH2$^{GOF}$ DLBCL cells. (A) Measurement of repair efficiency in SUDHL5 (EZH2$^{WT}$) and Karpas-422 (EZH2$^{GOF}$) cells using neutral comet assay that detects only double-strand breaks (DSBs). In the comet, the head (H) represents intact DNA and the tail (T) represents the number of DSBs in a single cell. Tail moment is a measure of length and intensity of DNA in the tail, and the average tail moments from 100 comets are indicated within the figure for each cell/treatment combination. Doxo indicates doxorubicin; H121N indicates HDAC1,2 inhibitor. (B) DNA damage in EZH2GOF cells following knockdown of HDAC1,2 using siRNA. NT indicates non-targeting control siRNA; HDAC1,2 siRNA indicates combined treatment with HDAC1 siRNA and HDAC2 siRNA. (C) Karpas-422 cells treated with DMSO solvent or HDAC1,2 inhibitor were subjected to microlaser irradiation. H3K27me3, γH2AX, Bmi-1, and serine2-phosphorylated RNA Polymerase II (engaged in transcriptional elongation) were monitored at laser break sites (arrows) after 15 minutes of recovery time. Numbers overlaying the images indicate percentages of cells with γH2AX lines that co-localized with H3K27me3, Bmi-1, or Pol2Ser2-P lines from at least four independent experiments (p value<0.01).

Selective Inhibition of HDAC1,2 Activities Blocks Active H3K27Me3 at DNA Break Sites, Impairs DNA Repair and Causes Cytotoxicity in $EZH2^{GOF}$ DLBCL Cells Treatment of $EZH2^{GOF}$ DLBCL lines (Karpas-422 and SUDHL4) with ACY957 for 72 hours resulted in a large increase in the number of sub-G1 or dead Karpas-422 cells and a cell cycle arrest at G1 phase in SUDHL4 cells, which could be due to impaired DNA repair. Indeed, EZH2, H3K27me3, and HDAC1,2 all localize to sites of DNA breaks, which links them to DNA repair. Neutral comet assays were performed to directly measure the efficiency of DSB repair in $EZH2^{WT}$ (wild-type) or $EZH2^{GOF}$ DLBCL cells following doxorubicin and HDAC1,2 inhibitor treatments. Karpas-422 is a doxorubicin resistant cell line, and Karpas-422 cells were far less sensitive to doxorubicin compared to the SUDHL5 cell line with wild type EZH2 in the neutral comet assays (FIG. 34A). However, the refractory Karpas-422 cells are sensitive to HDAC1,2 inhibition and HDAC1,2 inhibition makes these cells sensitive to doxorubicin treatment, because an increase in comet tail moment and a decrease in comet head intensity was observed with ACY957 alone and ACY957+doxorubicin treatments (FIG. 34A). Abrogating HDAC1,2 functions in $EZH2^{GOF}$ DLBCL cells using ACY957 or following siRNA knockdown led to an accumulation of DSBs, as evidenced by an increase in γH2AX (H2AX Serine 139 phosphorylation, a marker of DNA damage) foci by immunofluorescence (FIG. 34B). Therefore, these results provide direct evidence that impairment of DSB repair upon loss of HDAC1,2 increases DNA breaks in an otherwise chemoresistant $EZH2^{GOF}$ DLBCL cells to trigger death.

At a low 2 μM concentration, ACY957 or ACY1035 did not cause any cell death within 72 hr in non-transformed, mouse bone marrow Pro-B derived Baf3 cells or cord blood stem cells. Therefore, transformed lymphoma cells are more sensitive to HDAC1,2 inhibition when compared to the untransformed normal B-cells. HDAC1,2 inhibitor causes replication fork collapse in S-phase to trigger DNA damage response, and transformed cancer cells have increased DNA replication when compared to normal B cells. Hence transformed cancer cells are exquisitely sensitive to HDAC1,2 inhibition. In addition to this property, $EZH2^{GOF}$ DLBCL cells also have increased DNA repair compared to $EZH2^{WT}$ DLBCL cells (FIG. 34A), which can also be targeted by HDAC1,2 inhibitor as it impairs the HDAC1,2 regulated DNA repair processes used by $EZH2^{GOF}$ DLBCL cells for their survival.

To examine whether HDAC1,2 activities regulate EZH2-mediated H3K27me3 at the DNA break sites, experiments were performed using a system to create DNA breaks using microlaser in the non-adherent/suspension DLBCL cells. H3K27me3 catalyzed by EZH2 at laser-induced DNA breaks was abolished in the Karpas-422 cells treated with ACY957 (FIG. 34C). These results therefore showed that selective inhibition of HDAC1,2 in the $EZH2^{GOF}$ DLBCL cells impairs DNA repair and activates the DNA damage response in part by blocking the EZH2-mediated H3K27me3 at break sites. H3K27me3 recruits the PRC1 complex containing Bmi-1 E3 ligase to catalyze H2AK119 ubiquitination and facilitates further downstream EZH2 signaling. A decrease in repair factor Bmi-1 and an increase in serine 2-phosphorylated form of RNA polymerase II (a transcriptional elongation mark) at laser break sites was observed following HDAC1,2 inhibition (FIG. 34C). The disclosed results for the first time show the requirement of HDAC1,2 activities in EZH2-mediated DSB repair and the control of transcription at break sites.

Example 32

Acetylation at H2AK119, a Residue Involved in EZH2-Dependent Repair Signaling, is a Novel Target of HDAC1,2 in $EZH2^{GOF}$ DLBCL Cells H2AK119 monoubiquitination (H2AK119ub1) catalyzed by the PRC1 complex is downstream of the EZH2-containing PRC2 complex during DNA repair. H2AK119ub1 is required for recruiting several repair proteins including RNF8 and subsequent recruitment of BRCA1 and 53BP1 to the break sites in order to propagate damage signaling. To further understand the mechanisms by which HDAC1,2 regulate EZH2-mediated DSB repair signaling in the $EZH2^{GOF}$ DLBCL cells, experiments were performed to assess whether HDAC1,2 regulates H2AK119ub1 via targeting H2AK119 acetylation (H2AK119ac).

Figure 35:
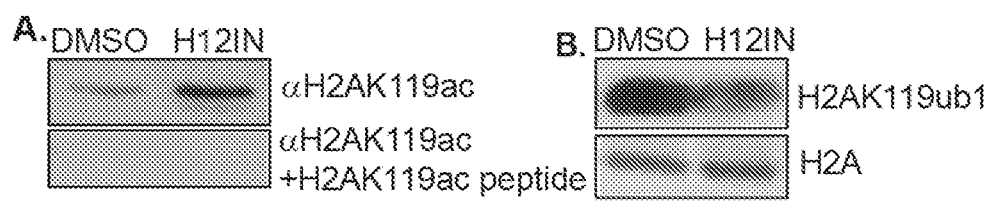
FIG. 35 shows that H2AK119ac is a novel target of HDAC1,2 and that HDAC1,2 inhibition alters the H2AK119ac-ub switch. (A) Western blot showing that treatment with an HDAC1,2 inhibitor (H121N) in EZH2$^{GOF}$ DLBCL cells leads to increased global H2AK119ac. (B) Western blot showing that treatment with an HDAC1,2 inhibitor in EZH2$^{GOF}$ cells leads to decreased chromatin-associated H2AK119ub.

Inhibition or knockdown of HDAC1,2 increases H2AK119ac (FIG. 35A). An increase in H2AK119ac is also accompanied by a decrease in global chromatin-associated H2AK119ub1 (FIG. 35B). HDAC1,2 inhibition thus decreases H2AK119ub1 indirectly via decreasing H3K27me3 (FIG. 34C) and directly by increasing H2AK119ac (FIG. 35), which adds another layer to the regulation of EZH2-mediated repair by HDAC1,2.

Example 33

HDAC1,2 Inhibition Increases H4K91Ac to Alter the H4K91Acetyl-Ubiquityl Switch Following Doxorubicin Treatment BBAP is overexpressed in the high risk, chemotherapy-resistant and aggressive form of DLBCL. BBAP catalyzes H4K91 monoubiquitination (H4K91ub1), which is proposed to protect cells from death when exposed to DNA damaging agents. We found BBAP protein levels are higher in Karpas-422 and SUDHL4 cells when compared to the chemosensitive SUDHL8 cells1. Inhibition of HDAC1,2 increased global H4K91ac levels in both SUDHL4 and Karpas-422 cells. ACY957 treatment resulted in a decrease in the BBAP-mediated H4K91 monoubiquitination following addition of doxorubicin1. Importantly, treatment with ACY957 sensitized the Karpas-422 cells to doxorubicin. Our results also showed that inhibition of HDAC1,2 delayed the kinetics of BBAP-dependent 53BP1 recruitment to damage sites. Therefore, our published results have provided a second mechanism by which HDAC1,2 inhibition impairs DNA repair and overcomes chemoresistance in EZH2$^{GOF}$ DLBCL cells via counteracting overexpressed BBAP activity in addition to nullifying the effects of a hyperactive EZH2 mutant.

Example 34

Therapeutic Efficacy of HDAC1,2 Inhibition in a Mouse Model of EZH2$^{GOF}$ DLBCL As disclosed herein, selective inhibition of HDAC1,2 triggers apoptosis in chemoresistant/refractory EZH2$^{GOF}$ DLBCL cells. A first-of-its-kind study was carried out to test the therapeutic benefits of selective inhibition of HDAC1,2 as a treatment for chemoresistant EZH2$^{GOF}$ DLBCL using a xenograft mouse model. We will examine whether HDAC1,2 inhibition alone or in combination with doxorubicin can causes tumor regression using this mouse model.

Figure 36:
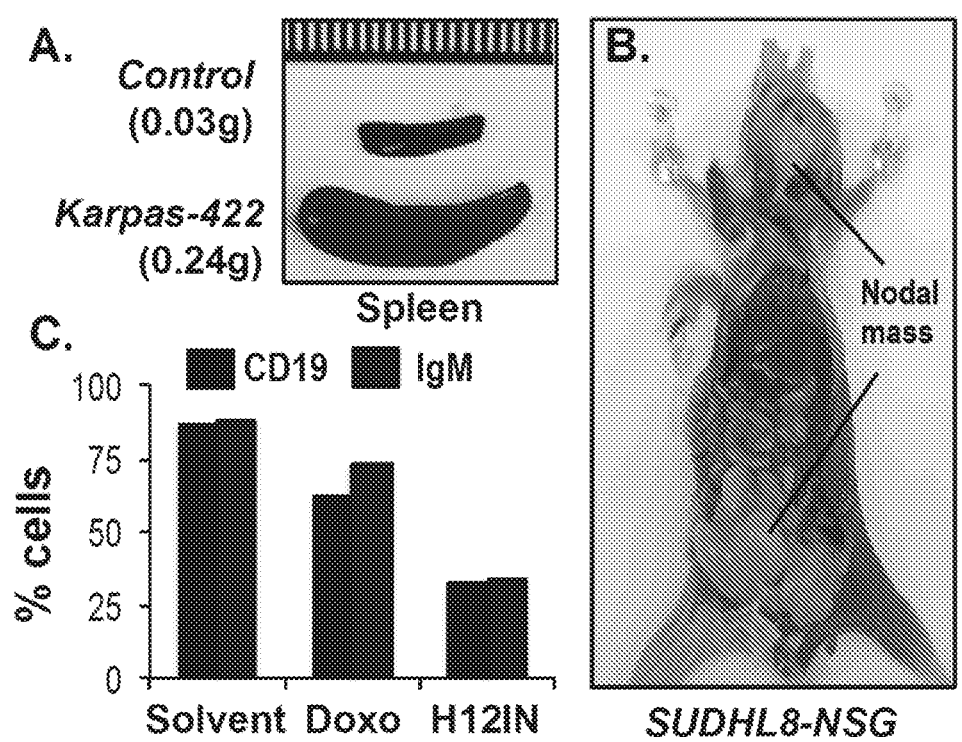
FIG. 36 shows chemoresistant and chemosensitive DLBCL xenograft mouse models. (A) Xenografted chemoresistant EZH2$^{GOF}$ DLBCL Karpas-422 cells home to spleen in NOD-SCID-Gamma mice. Spleens are enlarged in Karpas-422 NSG mice compared to control NSG mice. (B) Xenografted chemosensitive EZH2WT DLBCL SUDHL8 cells home to lymph nodes in NOD-SCID-Gamma mice. (C) FACS analyses of human CD19 and IgM markers in peripheral blood of Karpas-422/NSG xenograft mice treated with solvent or doxorubicin (Doxo) or the HDAC1,2 inhibitor ACY1035 (H12IN). Seventeen doses of HDAC1,2 inhibitor and five doses of doxorubicin were administered.

The in vivo testing used a doxorubicin-resistant EZH2$^{GOF}$ DLBCL (Karpas-422/NSG) mouse model and a doxorubicin-sensitive EZH2$^{WT}$ DLBCL (SUDHL8/NSG) mouse model (FIG. 36). To create these models, NOD-SCID-Gamma (NSG) mice were injected intravenously (i.v.) with 1×10$^6$ Karpas-422 cells (chemoresistant and expressing the EZH2 gain-of-function mutant) or SUDHL8 cells (chemosensitive and expressing wild-type EZH2). Human CD19+ cells were detected in the peripheral blood by FACS analysis following 5 days post-xenograft induction in the Karpas-422/NSG mouse model. Karpas-422/NSG mice had enlarged spleens compared to the control NSG mice at 5 weeks post-xenograft induction (FIG. 36A), indicating lymphoma development. On the other hand, SUDHL8 cells homed into the lymph nodes in NSG mice. Large lymphoma masses were observed in the neck and abdominal nodes of the SUDHL8/NSG xenograft mice (FIG. 36B). The difference in the homing of different DLBCL cells is consistent with human lymphomas, where some occur in spleen whereas others exhibit a lymphonodular distribution.

A significant decrease in human CD19 and IgM population in peripheral blood (PB) was observed with ACY1035-treated Karpas-422 xenograft mice, and no significant change in these markers was observed following doxorubicin treatment (FIG. 36C). The same concentration of doxorubicin significantly decreased leukemia burden in separate SupB15 Pre-B-ALL leukemia xenograft mice. Hence, the Karpas-422/NSG mice are doxorubicin-resistant even in the in vivo setting and HDAC1,2 inhibition seems to be effective in overcoming that chemoresistance (FIG. 36C).

Example 35

No Effect on the Cell Cycle Following HDAC1,2 Inhibition in Glioma Cells

Figure 37:
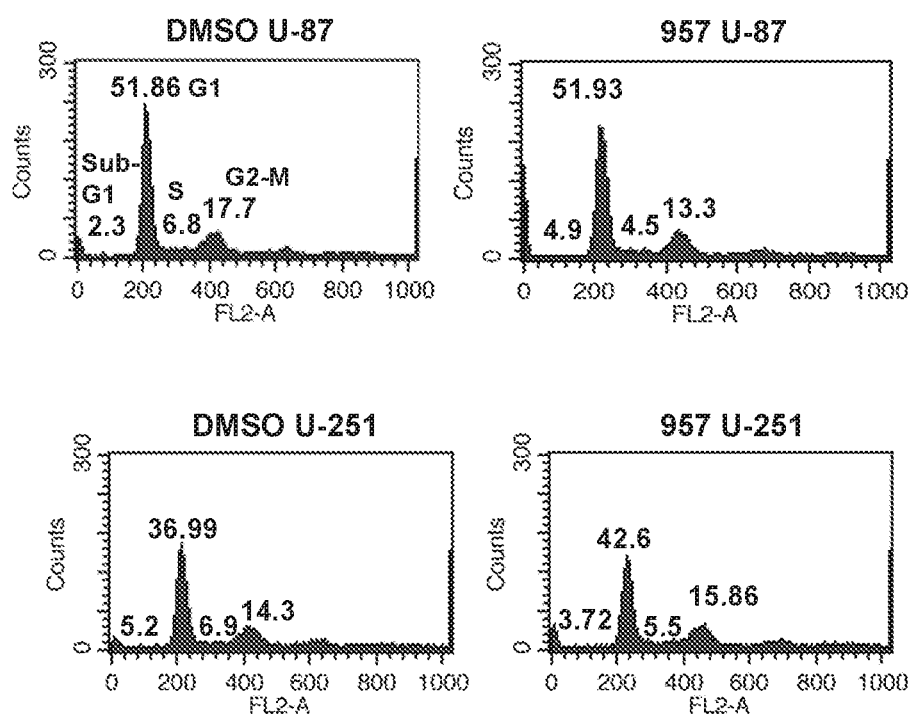
FIG. 37 shows FACS analyses of cell cycle progression in U-87 and U-251 glioma cells treated with the HDAC1,2 inhibitor ACY957 (957) or solvent (DMSO). Cells were treated with ACY957 or DMSO for 72 hours, stained with propidium iodide, and assessed by FACS. The percentage of cells in Sub-G1, G1, S, and G2-M phases were quantified for each sample.

Glioma is a type of primary brain tumor that originates in the glial cells present in the brain or spinal cord. The glioma cell lines U-87 and U-251 were treated with either DMSO or 2 µM ACY957 for 72 hours and then subjected to propidium iodide staining and FACS analysis to evaluate cell cycle progression. No effect on the cell cycle was observed in glioma cells following HDAC1,2 inhibition (FIG. 37).

8. Clauses

Clause 1. A method of treating a cancer characterized by BCR-ABL expression or BBAP overexpression in a subject in need thereof, the method comprising administering to the subject an agent that selectively inhibits HDAC1 and HDAC2.

Clause 2. The method of clause 1, wherein the cancer is a B cell malignancy.

Clause 3. The method of clause 2, wherein the B cell malignancy is diffuse large B cell lymphoma or early Pre-B cell derived acute lymphoblastic leukemia (Pre-B-ALL).

Clause 4. The method of clause 3, wherein the diffuse large B cell lymphoma contains a gain-of-function mutation in Enhancer of Zeste Homologue 2 (EZH2), a gain-of-function mutation in a histone H3K27 methyltransferase, or a loss-of-function mutation in a H3K27 demethylase.

Clause 5. The method of clause 3, wherein the Pre-B-ALL contains a chromosomal translocation and wherein the chromosomal translocation is t(9;22).

Clause 6. The method of any one of clauses 1-5, wherein the cancer is further characterized as being dependent upon on a double-stranded break repair pathway.

Clause 7. The method of clause 6, wherein the double-stranded break repair pathway includes one or more of the group consisting of FEN1, EPC2, BAF180, and DNA Ligase I.

Clause 8. The method of any one of clauses 1-7, wherein the cancer is further characterized by increased H3K27me3.

Clause 9. The method of any one of clauses 1-8, further comprising determining if the cancer is characterized by BCR-ABL expression or BBAP overexpression, wherein determining comprises detecting a level of BCR-ABL, a level of BBAP, or a level of BCR-ABL and a level of BBAP in a sample obtained from the subject.

Clause 10. The method of clause 9, further comprising comparing the detected levels of BCR-ABL, BBAP, or BCR-ABL and BBAP to levels of BCR-ABL, BBAP, or BCR-ABL and BBAP in a control sample, wherein if the detected level of BCR-ABL is increased relative to the control level of BCR-ABL, the cancer is characterized by BCR-ABL expression, and wherein if the detected level of BBAP is increased relative to the control level of BBAP, the cancer is characterized by BBAP overexpression.

Clause 11. The method of any one of clauses 1-10, further comprising sensitizing the cancer to a chemotherapeutic agent.

Clause 12. The method of clause 11, wherein the chemotherapeutic agent is doxorubicin.

Clause 13. The method of any one of clauses 1-12, further comprising administering doxorubicin to the subject.

Clause 14. A method of sensitizing a cancer characterized by BCR-ABL expression or BBAP overexpression to a chemotherapeutic agent in a subject in need thereof, the method comprising administering an agent that selectively inhibits HDAC1 and HDAC2 to the subject.

Clause 15. The method of clause 14, wherein the cancer is a B cell malignancy.

Clause 16. The method of clause 15, wherein the B cell malignancy is diffuse large B cell lymphoma or early Pre-B cell derived acute lymphoblastic leukemia (Pre-B-ALL).

Clause 17. The method of clause 16, wherein the diffuse large B cell lymphoma contains a gain-of-function mutation in Enhancer of Zeste Homologue 2 (EZH2), a gain-of-function mutation in a histone H3K27 methyltransferase, or a loss-of-function mutation in a H3K27 demethylase.

Clause 18. The method of clause 16, wherein the Pre-B-ALL contains a chromosomal translocation and wherein the chromosomal translocation is t(9;22).

Clause 19. The method of any one of clauses 14-18, wherein the cancer is further characterized as being dependent upon on a double-stranded break repair pathway.

Clause 20. The method of clause 19, wherein the double-stranded break repair pathway includes one or more of the group consisting of FEN1, EPC2, BAF180, and DNA Ligase I.

Clause 21. The method of any one of clauses 14-20, wherein the cancer is further characterized by increased H3K27me3.

Clause 22. The method of any one of clauses 14-21, further comprising determining if the cancer is characterized by BCR-ABL expression or BBAP overexpression, wherein determining comprises detecting a level of BCR-ABL, a level of BBAP, or a level of BCR-ABL and a level of BBAP in a sample obtained from the subject.

Clause 23. The method of clause 22, further comprising comparing the detected levels of BCR-ABL, BBAP, or BCR-ABL and BBAP to levels of BCR-ABL, BBAP, or BCR-ABL and BBAP in a control sample, wherein if the detected level of BCR-ABL is increased relative to the control level of BCR-ABL, the cancer is characterized by BCR-ABL expression, and wherein if the detected level of BBAP is increased relative to the control level of BBAP, the cancer is characterized by BBAP overexpression.

Clause 24. A method for determining if a cancer is sensitive to an agent that selectively inhibits HDAC1 and HDAC2, the method comprising: (a) obtaining a sample from a subject suffering from the cancer; (b) measuring a level of one or more markers in the sample, wherein the one or more markers are selected from the group consisting of: BCR-ABL and BBAP; (c) comparing the measured level of the one or more markers in the sample to a level of the one or more markers in a control sample; and (d) determining that the cancer is sensitive to an agent that selectively inhibits HDAC1 and HDAC2 when the measured level of the one or more markers in the sample is increased relative to the level of the one or more markers in the control sample.

Clause 25. The method of clause 24, further comprising administering the agent that selectively inhibits HDAC1 and HDAC2 to the subject suffering from the cancer that is sensitive to the agent.

Clause 26. The method of clause 24 or 25, wherein measuring the level of the one or markers includes an immunoassay, fluorescence in situ hybridization, or polymerase chain reaction.

Clause 27. The method of any one of clauses 24-26, wherein the cancer is a B cell malignancy.

Clause 28. The method of clause 27, wherein the B cell malignancy is diffuse large B cell lymphoma or early Pre-B cell derived acute lymphoblastic leukemia (Pre-B-ALL).

Clause 29. The method of clause 28, wherein the diffuse large B cell lymphoma contains a gain-of-function mutation in Enhancer of Zeste Homologue 2 (EZH2), a gain-of-function mutation in a histone H3K27 methyltransferase, or a loss-of-function mutation in a H3K27 demethylase.

Clause 30. The method of clause 28, wherein the Pre-B-ALL contains a chromosomal location and wherein the chromosomal location is t(9;22).

Clause 31. The method of any one of clauses 24-30, wherein the cancer is characterized as being dependent upon on a double-stranded break repair pathway.

Clause 32. The method of clause 31, wherein the double-stranded break repair pathway includes one or more of the group consisting of FEN1, EPC2, BAF180, and DNA Ligase I.

Clause 33. The method of any one of clauses 24-32, wherein the cancer is characterized by increased H3K27me3.

Clause 34. A method for monitoring the efficacy of a treatment for a cancer that includes administration of an agent that selectively inhibits HDAC1 and HDAC2, the method comprising: (a) obtaining a first sample from the subject before the treatment and a second sample from the subject during or after the treatment; (b) measuring a first level of one or more markers in the first sample and a second level of the one or more markers in the second sample, wherein the one or more markers are selected from the group consisting of: 53BP1, and γH2AX; (c) comparing the first level of the one or more markers and the second level of the one or more markers; and (d) determining that the treatment is effective when the second level of the one or more markers is higher than the first level of the one or more markers.

Clause 35. The method of clause 34, wherein measuring first and second levels of the one or more markers includes measuring foci formation of the one or more markers.

Clause 36. The method of clause 34 or 35, wherein the cancer is a B cell malignancy.

Clause 37. The method of clause 36, wherein the B cell malignancy is diffuse large B cell lymphoma or early Pre-B cell derived acute lymphoblastic leukemia (Pre-B-ALL).

Clause 38. The method of clause 37, wherein the diffuse large B cell lymphoma contains a gain-of-function mutation in Enhancer of Zeste Homologue 2 (EZH2), a gain-of-function mutation in a histone H3K27 methyltransferase, or a loss-of-function mutation in a H3K27 demethylase.

Clause 39. The method of clause 37, wherein the Pre-B-ALL contains a chromosomal translocation and wherein the chromosomal translocation is t(9;22).

Clause 40. The method of any one of clauses 34-39, wherein the cancer is characterized as being dependent upon on a double-stranded break repair pathway.

Clause 41. The method of clause 40, wherein the double-stranded break repair pathway includes one or more of the group consisting of FEN1, EPC2, BAF180, and DNA Ligase I.

Clause 42. The method of any one of clauses 34-41, wherein the cancer is characterized by increased H3K27me3.

Clause 43. The method of any one of clauses 34-42, further comprising administering a chemotherapeutic agent to the subject when the treatment is determined to be effective.

Clause 44. The method of clause 43, wherein the chemotherapeutic agent is doxorubicin.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method of treating a cancer characterized by BCR-ABL expression and BBAP overexpression in a subject in need thereof, the method comprising administering to the subject an agent that selectively inhibits HDAC1 and HDAC2.

2. The method of claim 1, wherein the cancer is a B cell malignancy.

3. The method of claim 2, wherein the B cell malignancy is diffuse large B cell lymphoma or early Pre-B cell derived acute lymphoblastic leukemia (Pre-B-ALL).

4. The method of claim 3, wherein the diffuse large B cell lymphoma contains a gain-of-function mutation in Enhancer of Zeste Homologue 2 (EZH2), a gain-of-function mutation in a histone H3K27 methyltransferase, or a loss-of-function mutation in a H3K27 demethylase.

5. The method of claim 3, wherein the Pre-B-ALL contains a chromosomal translocation and wherein the chromosomal translocation is t(9;22).

6. The method of claim 1, wherein the cancer is further characterized as being dependent upon on a double-stranded break repair pathway.

7. The method of claim 6, wherein the double-stranded break repair pathway includes one or more of the group consisting of FEN1, EPC2, BAF180, and DNA Ligase I.

8. The method of claim 1, wherein the cancer is further characterized by increased H3K27me3.

9. The method of claim 1, further comprising determining if the cancer is characterized by BCR-ABL expression and BBAP overexpression, wherein determining comprises detecting a level of BCR-ABL and a level of BBAP in a sample obtained from the subject, and comparing the detected levels of BCR-ABL and BBAP to levels of BCR-ABL and BBAP in a control sample, wherein if the detected level of BCR-ABL is increased relative to the control level of BCR-ABL, the cancer is characterized by BCR-ABL expression, and wherein if the detected level of BBAP is increased relative to the control level of BBAP, the cancer is characterized by BBAP overexpression.

10. The method of claim 1, further comprising administering doxorubicin to the subject.

11. A method of sensitizing a cancer characterized by BCR-ABL expression and BBAP overexpression to a chemotherapeutic agent in a subject in need thereof, the method comprising administering an agent that selectively inhibits HDAC1 and HDAC2 to the subject.

12. The method of claim 11, wherein the cancer is a B cell malignancy.

13. The method of claim 12, wherein the B cell malignancy is diffuse large B cell lymphoma or early Pre-B cell derived acute lymphoblastic leukemia (Pre-B-ALL).

14. The method of claim 13, wherein the diffuse large B cell lymphoma contains a gain-of-function mutation in Enhancer of Zeste Homologue 2 (EZH2), a gain-of-function mutation in a histone H3K27 methyltransferase, or a loss-of-function mutation in a H3K27 demethylase.

15. The method of claim 13, wherein the Pre-B-ALL contains a chromosomal translocation and wherein the chromosomal translocation is t(9;22).

16. The method of claim 11, wherein the cancer is further characterized as being dependent upon on a double-stranded break repair pathway.

17. The method of claim 16, wherein the double-stranded break repair pathway includes one or more of the group consisting of FEN1, EPC2, BAF180, and DNA Ligase I.

18. The method of claim 11, wherein the cancer is further characterized by increased H3K27me3.

19. The method of claim 11, further comprising determining if the cancer is characterized by BCR-ABL expression and BBAP overexpression, wherein determining comprises detecting a level of BCR-ABL and a level of BBAP in a sample obtained from the subject, and comparing the detected levels of BCR-ABL and BBAP to levels of BCR-ABL and BBAP in a control sample, wherein if the detected level of BCR-ABL is increased relative to the control level of BCR-ABL, the cancer is characterized by BCR-ABL expression, and wherein if the detected level of BBAP is increased relative to the control level of BBAP, the cancer is characterized by BBAP overexpression.

\* \* \* \* \*